(12) United States Patent
Pinho et al.

(10) Patent No.: US 10,118,941 B2
(45) Date of Patent: Nov. 6, 2018

(54) METHODS FOR THE PREPARATION OF DIASTEREOMERICALLY PURE PHOSPHORAMIDATE PRODRUGS

(71) Applicant: MEDIVIR AB, Stockholm (SE)

(72) Inventors: Pedro Pinho, Huddinge (SE); Staffan Torssell, Huddinge (SE)

(73) Assignee: MEDIVIR AB, Stockholm (SE)

( * ) Notice: Subject to any disclaimer, the term of this patent is extended or adjusted under 35 U.S.C. 154(b) by 51 days.

(21) Appl. No.: 15/511,096

(22) PCT Filed: Sep. 11, 2015

(86) PCT No.: PCT/EP2015/070876
§ 371 (c)(1),
(2) Date: Mar. 14, 2017

(87) PCT Pub. No.: WO2016/041877
PCT Pub. Date: Mar. 24, 2016

(65) Prior Publication Data
US 2017/0275322 A1    Sep. 28, 2017

(30) Foreign Application Priority Data

Sep. 15, 2014 (SE) ........................ 1451076
Sep. 16, 2014 (SE) ........................ 1451080
Mar. 9, 2015 (SE) ........................ 1550283

(51) Int. Cl.
C07H 21/00 (2006.01)
C07H 1/02 (2006.01)
C07H 1/04 (2006.01)
C07H 19/10 (2006.01)
C07H 19/20 (2006.01)

(52) U.S. Cl.
CPC ................. *C07H 1/02* (2013.01); *C07H 1/04* (2013.01); *C07H 19/10* (2013.01); *C07H 19/20* (2013.01)

(58) Field of Classification Search
None
See application file for complete search history.

(56) References Cited

FOREIGN PATENT DOCUMENTS

| JP | S54160344 A | 12/1979 |
| JP | S5793992 A | 6/1982 |
| WO | 2010135569 A1 | 11/2010 |
| WO | 2014164533 A1 | 10/2014 |
| WO | 2014169280 A2 | 10/2014 |

OTHER PUBLICATIONS

Kubota et al. JOC (2011), vol. 76, pp. 8710-8717.*
International Search Report dated Nov. 3, 2015.

* cited by examiner

*Primary Examiner* — Patrick T Lewis
(74) *Attorney, Agent, or Firm* — Gorman IP Law, APC

(57) ABSTRACT

Methods for the preparation of diastereomerically pure phosphoramidate prodrugs of nucleosides, and intermediates useful for the preparation are provided. The nucleosides are useful for the treatment of hepatitis C and cancer.

18 Claims, No Drawings

METHODS FOR THE PREPARATION OF DIASTEREOMERICALLY PURE PHOSPHORAMIDATE PRODRUGS

This application is the National Phase Under 35 USC § 371 of PCT International Application No. PCT/EP2015/070876 filed on Sep. 11, 2015, which claims priority under 35 U.S.C. § 119 on Patent Application No. 1451076-2 filed in Sweden on Sep. 15, 2014, and Patent Application No. 1451080-4 filed in Sweden on Sep. 16, 2014, and Patent Application No. 1550283-4 filed in Sweden on Mar. 9, 2015, the entire contents of each of which are hereby incorporated by reference.

FIELD OF THE INVENTION

The invention relates generally to methods for preparing prodrugs of nucleoside triphosphate inhibitors of cancer, or of viral infection, such as inhibitors of hepatitis C virus RNA-dependent RNA polymerase.

BACKGROUND OF THE INVENTION

Nucleoside inhibitors of viral polymerases and cancers are typically active as the nucleoside triphosphate (NTP). Conventional nucleoside drugs are phosphorylated by host cellular kinases to the triphopshate active form. The poor conversion of the nucleoside to NTP can often be attributed to the inability of nucleoside kinases to convert the nucleoside to the nucleoside 5'-monophosphate (NMP). NMP prodrugs have been used to bypass poor nucleoside kinase activity (Schultz, Bioorg. Med. Chem. 2003, 11, 885). Among these prodrugs, NMP phosphoramidates have been reported to increase intracellular concentrations of NTP compared to the nucleoside alone (McGuigan, J. Med. Chem. 1993, 36, 1048-1052). However, these NMP prodrugs are substrates for esterases and phosphodiesterases in the blood and other body tissues which can cleave the prodrug to a charged molecule or to the nucleoside, respectively. The charged molecule is then impermeable to the target organ or cell and the nucleoside is poorly phosphorylated intracellularly.

The development of a highly effective, non-toxic NMP prodrug is largely an unpredictable trial and error exercise requiring the balancing of the stability of the NMP prodrug in blood with the ability of the prodrug to reach a target organ or cell, be absorbed or actively taken up by the target cell, being efficiently cleaved to the NMP intracellularly and subsequently converted to a NTP that is selective for inhibiting the viral polymerase (Perrone, J. Med. Chem. 2007, 50, 1840-49; Gardelli, J. Med. Chem. 2009, 52, 5394-5407). For the case of an orally effective RdRp inhibitor for treating HCV infection, the NMP prodrug would need to be chemically stable to the conditions of the upper intestinal tract, be efficiently absorbed from the intestinal tract, survive the many esterases of the intestinal cells and blood, be efficiently extracted by the hepatocytes, and be cleaved to the NMP and subsequently converted to a NTP in hepatocytes that is specific for inhibiting the HCV NS5B polymerase.

The first generations of phosphoramidate prodrugs, such as AZT phosphoramidates (McGuigan 1993, J Med Chem 36 1048-1052) or BMS/Inhibitex INX-189 (WO2010/081082) were prepared as diasteroemeric mixtures at the phosphorous atom. Merck, Idenix and Achillion are believed to have clinical trials ongoing in relation to diverse phosphoramidate prodrugs of HCV-inhibitory nucleosides. Gemcitabine is an example of an anticancer nucleoside, which has been put into clinical trials by Nucana as a phosphoramidate prodrug (WO2005/01237). Nucana also works with phosphoramidate prodrugs of other anticancer nucleosides including clofarabine, fludarabin, cladribine (WO2006/100439) and FUDR (WO2012117246). Nucana's phosphoramidate prodrugs are typically a diastereomeric mixture at the phosphorous.

Subsequent generations of phosphoramidate prodrugs of an inhibitor of hepatitis C virus RNA-dependent RNA polymerase, such as Sofosbuvir (WO2008/121634) are diasteromerically pure at the phosphorous. Notably, the antiviral activity of phosphate prodrugs can markedly depend upon the chirality of the phosphorous in the prodrug (Gardelli, J. Med. Chem. 2009, 52, 5394-5407; Meppen, Abstracts of Papers, 236th ACS National Meeting, Philadelphia, Pa., United States, Aug. 17-21, 2008 (2008), MEDI-404.).

Pharmasset, later bought by Gilead, have described chiral phosphoramidate reagents in WO2010/135569, WO2011/123645 and WO2012/012465 useful in the preparation of sofosbuvir.

In view of the importance of anti-HCV therapeutics that are NMP prodrugs with chiral phosphorous atoms such as sofosbuvir or those described by Gardelli, et al., Perrone et al., and Meppen, et al., new efficient methods of producing chiral phosphates of these prodrugs are needed.

WO2012/012465 discloses methods and intermediates for preparing diasteromerically pure phosphoramidate prodrugs of nucleosides that are useful for the treatment of hepatitis C infection. The phosphorylating reagent disclosed therein is a phosphoramidate having an aryloxy or heteroaryloxy group, O—Ar, attached to the phosphorus atom as leaving group, i.e. a compound of formula Aa or Ab:

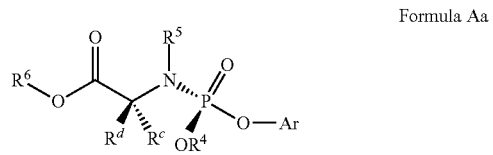

Formula Aa

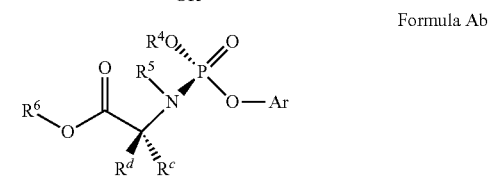

Formula Ab wherein Ar is a $(C_6-C_{20})$aryl or heteroaryl which is substituted with one or more halogen, $NO_2$, or $(C_1-C_8)$haloalkyl, and Ar is different from $R^4$.

SUMMARY OF THE INVENTION

Provided are methods for preparing prodrugs of nucleoside triphosphate inhibitors of cancer, or of viral infection, such as inhibitors of hepatitis C virus RNA-dependent RNA polymerase.

The compounds are prodrugs of nucleoside monophosphates that, when administered to animals, are intracellularly converted to nucleoside triphosphates. The chirality of the phosphorous atom determines the efficiency of the conversion to the nucleoside triphosphate in the animal. The method disclosed provides a convergent synthesis of these single diastereomeric prodrugs which is an improvement over the previously disclosed chromatographic methods of separating a single diastereomer from a mixture of diastereomers.

In one embodiment, a method for preparing a compound of Formula Ia or Ib is provided:

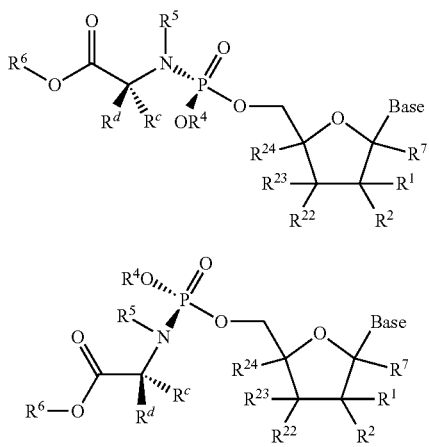

Formula Ia

Formula Ib or a pharmaceutically acceptable salt or acid thereof;
wherein:
each $R^1$, $R^2$, $R^7$, $R^{22}$, $R^{23}$ or $R^{24}$ is independently H, $OR^{11}$, $NR^{11}R^{12}$, $C(O)NR^{11}R^{12}$, $-OC(O)NR^{11}R^{12}$, $C(O)OR^{11}$, $OC(O)OR^{11}$, $S(O)_nR^a$, $S(O)_2NR^{11}R^{12}$, $N_3$, CN, halogen, $(C_1\text{-}C_8)$alkyl, $(C_3\text{-}C_8)$carbocyclyl, $(C_4\text{-}C_8)$carbocyclylalkyl, $(C_2\text{-}C_8)$alkenyl, $(C_2\text{-}C_8)$alkynyl or aryl$(C_1\text{-}C_8)$alkyl;
or any two $R^1$, $R^2$, $R^7$, $R^{22}$, $R^{23}$ or $R^{24}$ on adjacent carbon atoms when taken together are $-O(CO)O-$ or $-O(CR^{11}R^{12})O-$ or when taken together with the ring carbon atoms to which they are attached form a double bond;
each Base is independently a naturally occurring or modified purine or pyrimidine base linked to the furanose ring through a carbon or nitrogen atom;
each n is independently 0, 1, or 2;
each $R^a$, $R^4$ or $R^6$ is independently $(C_1\text{-}C_8)$alkyl, $(C_2\text{-}C_8)$alkenyl, $(C_2\text{-}C_8)$alkynyl, $(C_3\text{-}C_8)$carbocyclyl, $(C_4\text{-}C_8)$carbocyclylalkyl, aryl$(C_1\text{-}C_8)$alkyl, heterocyclyl$(C_1\text{-}C_8)$alkyl, $(C_6\text{-}C_{20})$aryl, heterocyclyl or heteroaryl;
each $R^c$ or $R^d$ is independently H, $(C_1\text{-}C_8)$alkyl, $(C_2\text{-}C_8)$alkenyl, $(C_2\text{-}C_8)$alkynyl, $(C_3\text{-}C_8)$carbocyclyl, $(C_4\text{-}C_8)$carbocyclylalkyl, aryl$(C_1\text{-}C_8)$alkyl, heterocyclyl$(C_1\text{-}C_8)$alkyl, $(C_6\text{-}C_{20})$aryl, heterocyclyl or heteroaryl provided that $R^c$ and $R^d$ are not the same;
each $R^5$ is independently H, $(C_1\text{-}C_8)$alkyl, $(C_2\text{-}C_8)$alkenyl, $(C_2\text{-}C_8)$alkynyl, $(C_3\text{-}C_8)$carbocyclyl, $(C_4\text{-}C_8)$carbocyclylalkyl, aryl$(C_1\text{-}C_8)$alkyl, heterocyclyl$(C_1\text{-}C_8)$alkyl, $(C_6\text{-}C_{20})$aryl, heterocyclyl or heteroaryl;
each $R^{11}$ or $R^{12}$ is independently H, $(C_1\text{-}C_8)$alkyl, $(C_2\text{-}C_8)$alkenyl, $(C_2\text{-}C_8)$alkynyl, $(C_3\text{-}C_8)$carbocyclyl, $(C_4\text{-}C_8)$carbocyclylalkyl, aryl$(C_1\text{-}C_8)$alkyl, heterocyclyl$(C_1\text{-}C_8)$alkyl, $(C_6\text{-}C_{20})$aryl, heterocyclyl, heteroaryl, $-C(=O)(C_1\text{-}C_8)$alkyl, $-S(O)_n(C_1\text{-}C_8)$alkyl or $R^{11}$ and $R^{12}$ taken together with a nitrogen to which they are both attached form a 3 to 7 membered heterocyclic ring wherein any one carbon atom of said heterocyclic ring can optionally be replaced with $-O-$, $-S(O)_n-$ or $-NR^a-$; and
wherein each $(C_1\text{-}C_8)$alkyl, $(C_2\text{-}C_8)$alkenyl, $(C_2\text{-}C_8)$alkynyl, $(C_3\text{-}C_8)$carbocyclyl, $(C_4\text{-}C_8)$carbocyclylalkyl, aryl$(C_1\text{-}C_8)$alkyl, heterocyclyl$(C_1\text{-}C_8)$alkyl, $(C_6\text{-}C_{20})$aryl, heterocyclyl or heteroaryl of each $R^c$, $R^d$, $R^1$, $R^2$, $R^{22}$, $R^{23}$, $R^{24}$, $R^4$, $R^5$, $R^6$, $R^7$, $R^{11}$ or $R^{12}$ is, independently, optionally substituted with one or more halo, hydroxy, CN, $N_3$, $N(R^a)_2$, $NH(R^a)$, $NH_2$, $NO_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $C(O)R^a$, $OC(O)R^a$, $S(O)_nR^a$ $S(O)_2N(R^a)_2$, $S(O)_2NH(R^a)$, $S(O)_2NH_2$, $OR^a$ or $R^a$;

said method comprising:
(a) providing a compound of Formula II

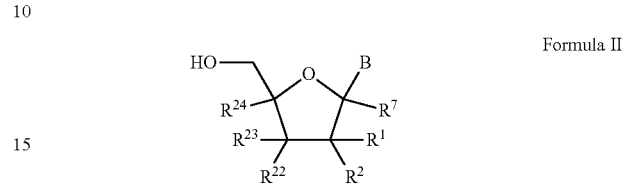

Formula II and
(b) treating the compound of Formula II with a compound of Formula IIIa and a base

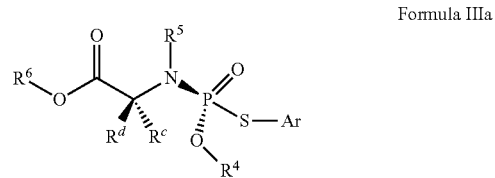

Formula IIIa thereby forming a compound of Formula Ia or
(c) treating the compound of Formula II with a compound of Formula IIIb and a base

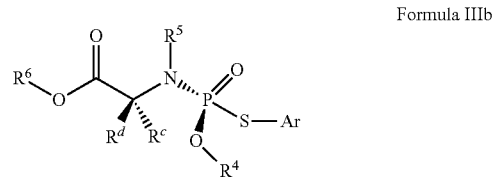

Formula IIIb thereby forming a compound of Formula Ib;
wherein:
each Ar is $(C_6\text{-}C_{20})$aryl or a 5 to 20 membered heteroaryl wherein said aryl or heteroaryl is substituted with one or more halogen, $NO_2$, or $(C_1\text{-}C_8)$haloalkyl and optionally substituted with one or more CN, $N_3$, $N(R^a)_2$, $C(O)N(R^a)_2$, $OC(O)N(R^a)_2$, $C(O)OR^a$, $OC(O)OR^a$, $C(O)R^a$, $OC(O)R^a$, $S(O)_nR^a$, $S(O)_2N(R^a)_2$, $OR^a$ or $R^a$ with the proviso that Ar is different from $R^4$.

In another aspect, the invention provides novel intermediates disclosed herein which are useful for preparing compounds of Formula Ia or Formula Ib.

In other aspects, methods for the synthesis, analysis, separation, isolation, purification, and characterization of the novel intermediates of this invention are provided.

DETAILED DESCRIPTION OF EXEMPLARY EMBODIMENTS

Reference will now be made in detail to certain embodiments of the invention, examples of which are illustrated in the accompanying description, structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention.

Typically, the method of for preparing a compound of Formula Ia from a compound of Formula II and a compound of Formula IIIa, or preparing a compound of Formula Ib from compound of Formula II and a compound of Formula IIIb is performed in a suitable solvent. The suitable solvent is preferably an anhydrous, non-acid, non-hydroxylic solvent. Non-limiting examples of suitable solvents are ethers, for example, diethyl ether, diisopropyl ether, di i-butyl ether, tetrahydrofuran, dioxane and various glyme solvents; dimethylformamide or dimethylacetamide.

A preferred solvent is tetrahydrofuran. The concentration of Formula II in the solvent is typically about 0.01 to about 1 mole per liter of solvent. The method is performed at a temperature of about −20° C. to about 90° C., more preferably about −10° C. to about 60° C.

The solution of Formula II is typically treated with a hindered base or a non-nucleophilic base. Typical, but non-limiting, examples of hindered bases are t-butyllithium, sec-isobutyllithium, lithium or sodium diisopropylamide and t-butylmagnesium halides. A preferred hindered base is i-butylmagnesium chloride. A further preferred base is t-butylmagnesium chloride. Typical, but non-limiting, examples of non-nucleophilic bases are sodium hydride, potassium hydride, lithium hydride and calcium hydride. The hindered bases or non-nucleophic bases may be used as solutions in or as undiluted bases. Preferably, the bases are used as solutions in anhydrous, non-hydroxylic solvents wherein the concentration of the base in the solvent is about 0.5 to about 3 moles per liter. The molar ratio of base to the compound of Formula II will depend on the Base attached to the furanose ring. The ratio is about 1:1 to about 3:1, preferably about 1.1:1 to about 2.1:1. The solution of the compound of Formula II is typically treated with the base for about 5 minutes to about two hours, preferably less than 30 minutes.

The mixture of the solution of the compound of Formula II and the base is treated with a compound of Formula IIIa or Formula IIIIb for about 30 minutes to about 24 hours, preferably about one to about four hours. The molar ratio of the compound of Formula II to the compound of Formula IIIa or Formula IIIb is typically about 1:1 to about 1:4. Preferably, the molar ratio is about 1:1.1 to about 1:2.

In another embodiment of the method for preparing a compound of Formula Ia or Ib or a pharmaceutically salt or ester thereof, Formula Ia is Formula IVa, Formula Ib is Formula IVb and Formula II is Formula V:

Formula IVa

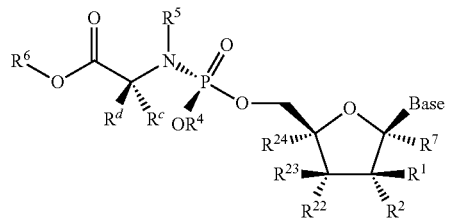

Formula IVb

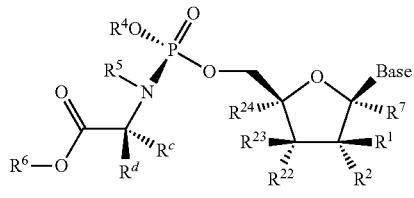

Formula V

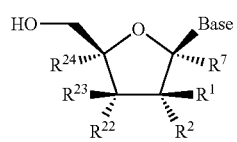

In one embodiment of the method for preparing a compound of Formula IVa or IVb from a compound of Formula V, $R^1$ is H, halogen, optionally substituted $(C_1-C_8)$alkyl, optionally substituted $(C_2-C_8)$alkenyl or optionally substituted $(C_2-C_8)$alkynyl. In another aspect of this embodiment, $R^1$ is H. In another aspect of this embodiment, $R^1$ is optionally substituted $(C_1-C_6)$alkyl. In another aspect of this embodiment, $R^1$ is methyl. In another aspect of this embodiment, $R^1$ is optionally substituted $(C_2-C_8)$alkenyl. In another aspect of this embodiment, $R^1$ is optionally substituted $(C_2-C_8)$alkynyl. In another aspect of this embodiment, $R^1$ is F. In another aspect of this embodiment, $R^1$ is optionally substituted $(C_2-C_8)$alkynyl. In another aspect of this embodiment, $R^1$ is Cl. In another aspect of this embodiment, $R^2$ is F. In another aspect of this embodiment, $R^2$ is $OR^{11}$. In another aspect of this embodiment, $R^2$ is Cl. In another aspect of this embodiment, $R^{22}$ is OH. In another aspect of this embodiment, $R^7$ is H. In another aspect of this embodiment, $R^7$ is optionally substituted $(C_1-C_8)$alkyl. In another aspect of this embodiment, $R^7$ is optionally substituted $(C_2-C_8)$alkynyl. In another aspect of this embodiment, $R^7$ is CN. In another aspect of this embodiment, $R^5$ is H. In another aspect of this embodiment, one of $R^c$ or $R^d$ is H. In another aspect of this embodiment, one of $R^c$ or $R^d$ is H and the other of $R^c$ or $R^d$ is optionally substituted $(C_1-C_8)$alkyl. In another aspect of this embodiment, $R^6$ is optionally substituted $(C_1-C_8)$alkyl or optionally substituted $(C_3-C_8)$carbocyclyl. In another aspect of this embodiment, $R^4$ is optionally substituted $(C_6-C_{20})$aryl. In another aspect of this embodiment, Ar is optionally substituted phenyl. In another aspect of this embodiment, $R^{23}$ is H. In another aspect of this embodiment, $R^{22}$ is $OR^1$. In another aspect of this embodiment, $R^{22}$ is OH. In another aspect of this embodiment, $R^{24}$ is $N_3$. In another aspect of this embodiment, $R^{24}$ is H. In another aspect of this embodiment, Base is selected from the group consisting of:

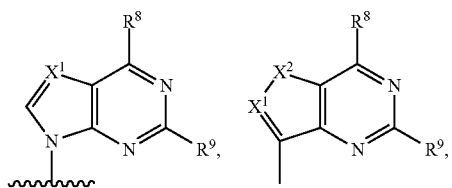

-continued

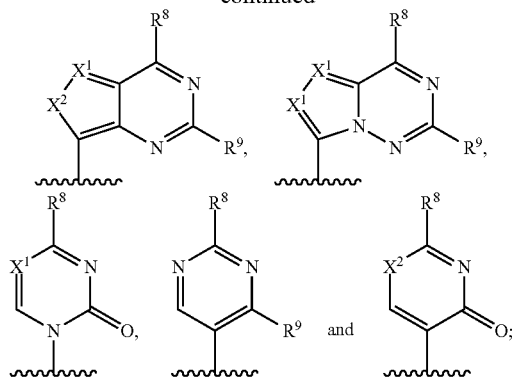

wherein:
each $X^1$ is independently N or $CR^{10}$;
each $X^2$ is independently $NR^1$, O, or $S(O)_n$;
each $R^8$ is independently halogen, $NR^{11}R^{12}$, $N(R^{11})OR^{11}$, $NR^{11}NR^{11}R^{12}$, $N_3$, NO, $NO_2$, CHO, CN, —CH(=$NR^{11}$), —CH=$NNHR^{11}$, —CH=N($OR^{11}$), —CH($OR^{11}$)$_2$, —C(=O)$NR^{11}R^{12}$, —C(=S)$NR^{11}R^{12}$, C(O)$OR^{11}$, ($C_1$-$C_8$)alkyl, ($C_2$-$C_8$)alkenyl, ($C_2$-$C_8$)alkynyl, ($C_4$-$C_8$)carbocyclylalkyl, ($C_6$-$C_{20}$)aryl, heterocyclyl, heteroaryl, —C(=O)($C_1$-$C_8$)alkyl, —S(O)$_n$($C_1$-$C_8$)alkyl, aryl($C_1$-$C_8$)alkyl, $OR^1$ or $SR^{11}$;
each n is independently 0, 1, or 2;
each $R^9$ or $R^{10}$ is independently H, halogen, $NR^{11}R^{12}$, $N(R^{11})OR^{11}$, $NR^{11}NR^{11}R^{12}$, $N_3$, NO, $N0_2$, CHO, CN, —CH(=$NR^{11}$), —CH=$NHNR^{11}$, —CH=N($OR^{11}$), —CH($OR^{11}$)$_2$, —C(=O)$NR^{11}R^{12}$, —C(=S)$NR^{11}R^{12}$, —C(=O)$OR^{11}$, $R^{11}$, $OR^{11}$ or $SR^{11}$; each $R^{11}$ or $R^{12}$ is independently H, ($C_1$-$C_8$)alkyl, ($C_2$-$C_8$)alkenyl, ($C_2$-$C_8$)alkynyl, ($C_3$-$C_8$)carbocyclyl, ($C_4$-$C_8$)carbocyclylalkyl, aryl($C_1$-$C_8$)alkyl, heterocyclyl($C_1$-$C_8$)alkyl, ($C_6$-$C_{20}$)aryl, heterocyclyl, heteroaryl, —C(=O)($C_1$-$C_8$)alkyl, —S(O)$_n$($C_1$-$C_8$)alkyl or $R^{11}$ and $R^{12}$ taken together with a nitrogen to which they are both attached form a 3 to 7 membered heterocyclic ring wherein any one carbon atom of said heterocyclic ring can optionally be replaced with —O—, —S(O)$_n$— or —$NR^a$—;
wherein each ($C_1$-$C_8$)alkyl, ($C_2$-$C_8$)alkenyl, ($C_2$-$C_8$)alkynyl, ($C_3$-$C_8$)carbocyclyl, ($C_4$-$C_8$)carbocyclylalkyl, aryl ($C_1$-$C_8$)alkyl, heterocyclyl($C_1$-$C_8$)alkyl, ($C_6$-$C_{20}$)aryl, heterocyclyl or heteroaryl of each $R^c$, $R^d$, $R^1$, $R^2$, $R^{22}$, $R^{23}$, $R^{24}$, $R^4$, $R^5$, $R^6$, $R^7$, $R^8$, $R^9$, $R^{10}$, $R^{11}$ or $R^{12}$ is, independently, optionally substituted with one or more halo, hydroxy, CN, $N_3$, N($R^a$)$_2$, NH($R^a$), $NH_2$, $NO_2$, C(O)N($R^a$)$_2$, C(O)NH($R^a$), C(O)$NH_2$, OC(O)N($R^a$)$_2$, OC(O)NH($R^a$), OC(O)$NH_2$, C(O)$OR^a$, OC(O)$OR^a$, C(O)$R^a$, OC(O)$R^a$, S(O)$_nR^a$, S(O)$_2$N($R^a$)$_2$, $S(O)_2$NH($R^a$), $S(O)_2NH_2$, $OR^a$ or $R^a$.
In another aspect of this embodiment, Base is selected from the group consisting of:

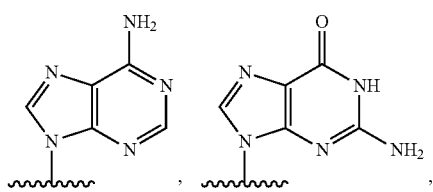

In another aspect of this embodiment, Base is selected from the group consisting of:

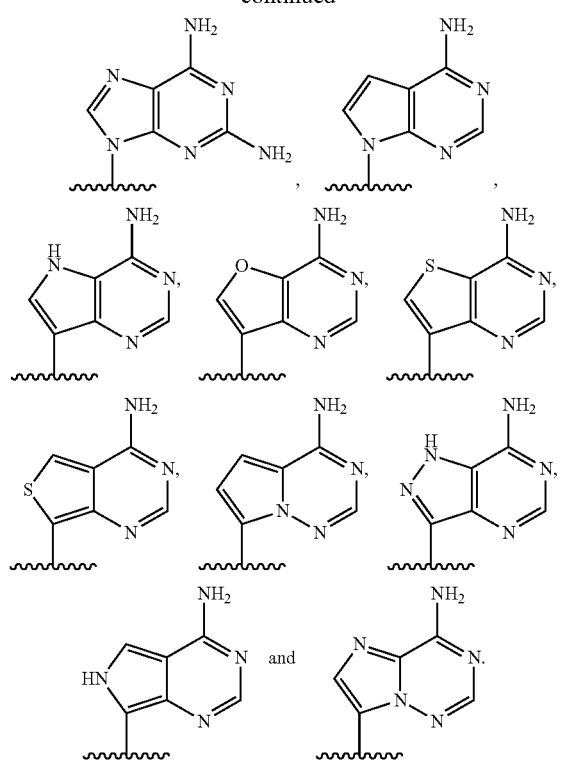

In another aspect of this embodiment, Base is selected from the group consisting of:

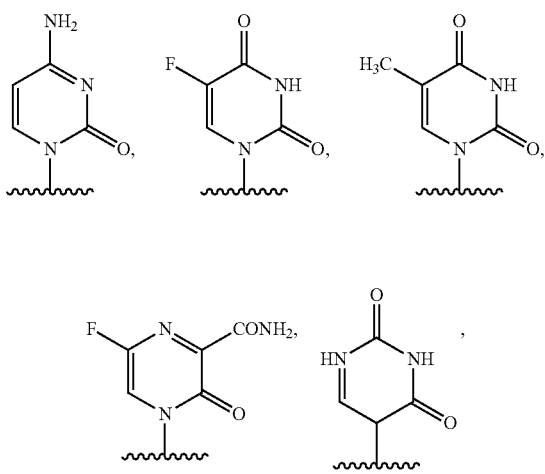

In another aspect of this embodiment, Base is selected from the group consisting of:

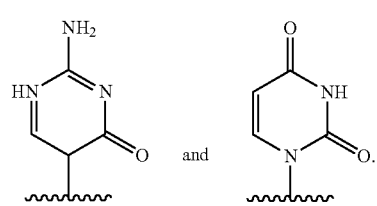

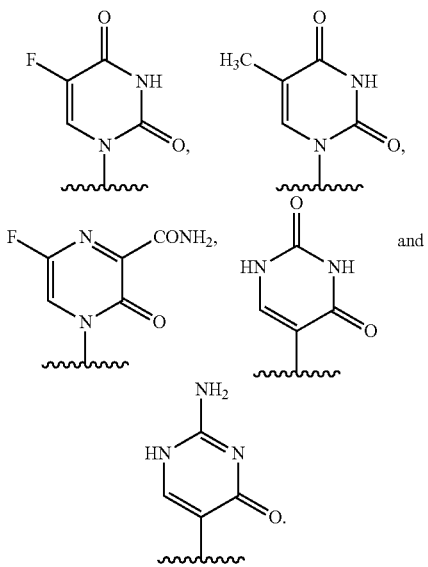

In another embodiment of the method for preparing a compound of Formula IVa or IVb from a compound of Formula V, $R^1$ is H, halogen, optionally substituted $(C_1-C_8)$ alkyl, optionally substituted $(C_2-C_8)$alkenyl or optionally substituted $(C_2-C_8)$alkynyl; $R^2$ is $OR^{11}$ or halogen; $R^{22}$ is $OR^{11}$ and each $R^5$, $R^{23}$ and $R^{24}$ is H. In another aspect of this embodiment, $R^1$ is H. In another aspect of this embodiment, $R^1$ is optionally substituted $(C_1-C_8)$alkyl. In another aspect of this embodiment, $R^1$ is methyl. In another aspect of this embodiment, $R^1$ is optionally substituted $(C_2-C_8)$alkenyl. In another aspect of this embodiment, $R^1$ is optionally substituted $(C_2-C_8)$alkynyl. In another aspect of this embodiment, $R^1$ is F. In another aspect of this embodiment, $R^1$ is Cl. In another aspect of this embodiment, $R^2$ is F. In another aspect of this embodiment, $R^2$ is OH. In another aspect of this embodiment, $R^2$ is Cl. In another aspect of this embodiment, $R^{22}$ is OH. In another aspect of this embodiment, each $R^2$ and $R^{22}$ is OH. In another aspect of this embodiment, $R^7$ is H. In another aspect of this embodiment, $R^7$ is optionally substituted $(C_1-C_8)$alkyl. In another aspect of this embodiment, $R^7$ is optionally substituted $(C_2-C_8)$alkynyl. In another aspect of this embodiment, $R^7$ is ON. In another aspect of this embodiment, one of $R^c$ or $R^d$ is H. In another aspect of this embodiment, one of $R^c$ or $R^d$ is H and the other of $R^c$ or $R^d$ is optionally substituted $(C_1-C_8)$alkyl. In another aspect of this embodiment, $R^6$ is optionally substituted $(C_1-C_8)$alkyl. In another aspect of this embodiment, $R^6$ is $(C_3-C_8)$carbocyclyl. In another aspect of this embodiment, $R^4$ is optionally substituted $(C_6-C_{20})$aryl. In another aspect of this embodiment, Ar is optionally substituted phenyl. In another aspect of this embodiment, Base is selected from the group consisting of:

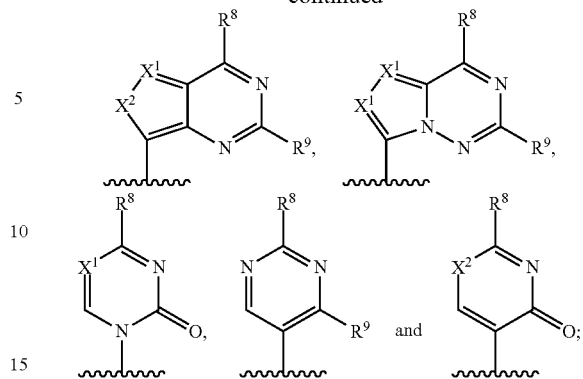

wherein:

each $X^1$ is independently N or $CR^{10}$;

each $X^2$ is independently $NR^1$, O, or $S(O)_n$;

each $R^8$ is independently halogen, $NR^{11}R^{12}$, $N(R^{11})OR^{11}$, $NR^{11}NR^{11}R^{12}$, $N_3$, NO, $NO_2$, CHO, ON, —CH(=$NR^{11}$), —CH=$NNHR^{11}$, —CH=N($OR^{11}$), —CH($OR^{11})_2$, —C(=O)$NR^{11}R^{12}$, —C(=S)$NR^{11}R^{12}$, —C(O)$OR^{11}$, $(C_1-C_8)$alkyl, $(C_2-C_8)$alkenyl, $(C_2-C_8)$alkynyl, $(C_4-C_8)$carbocyclylalkyl, $(C_6-C_{20})$aryl, heterocyclyl, heteroaryl, —C(=O)$(C_1-C_8)$alkyl, —S(O)$_n(C_1-C_8)$alkyl, aryl$(C_1-C_8)$alkyl, $OR^{11}$ or $SR^{11}$;

each n is independently 0, 1, or 2;

each $R^9$ or $R^{10}$ is independently H, halogen, $NR^{11}R^{12}$, $N(R^{11})OR^{11}$, $NR^{11}NR^{11}R^{12}$, $N_3$, NO, $NO_2$, CHO, CN, —CH(=$NR^{11}$), —CH=$NHNR^{11}$, —CH=N($OR^{11}$), —CH($OR^{11})_2$, —C(=O)$NR^{11}R^{12}$, —C(=S)$NR^{11}R^{12}$, —C(=O)$OR^1$, $OR^{11}$ or $SR^{11}$; each $R^{11}$ or $R^{12}$ is independently H, $(C_1-C_8)$ alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, heterocyclyl, heteroaryl, —C(=O)$(C_1-C_8)$alkyl, —S(O)$_n(C_1-C_8)$alkyl or $R^{11}$ and $R^{12}$ taken together with a nitrogen to which they are both attached form a 3 to 7 membered heterocyclic ring wherein any one carbon atom of said heterocyclic ring can optionally be replaced with —O—, —S(O)$_n$— or —$NR^a$—;

wherein each $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C20)$aryl, heterocyclyl or heteroaryl of each $R^c$, $R^d$, $R^1$, $R^2$, $R^{22}$, $R^{23}$, $R^{24}$, $R^4$, $R^5$, $R^6$, $R^7$, $R^8$, $R^9$, $R^{10}$, $R^{11}$ or $R^{12}$ is, independently, optionally substituted with one or more halo, hydroxy, CN, $N_3$, $N(R^a)_2$, $NH(R^a)$, $NH_2$, $NO_2$, C(O)$N(R^a)_2$, C(O)$NH(R^a)$, C(O)$NH_2$, OC(O)$N(R^a)_2$, OC(O)$NH(R^a)$, OC(O)$NH_2$, C(O)$OR^a$, OC(O)$OR^a$, C(O)$R^a$, OC(O)$R^a$, S(O)$_nR^a$, S(O)$_2N(R^a)_2$, S(O)$_2NH(R^a)$, S(O)$_2NH_2$, $OR^a$ or $R^a$.

In another aspect of this embodiment, Base is selected from the consisting of:

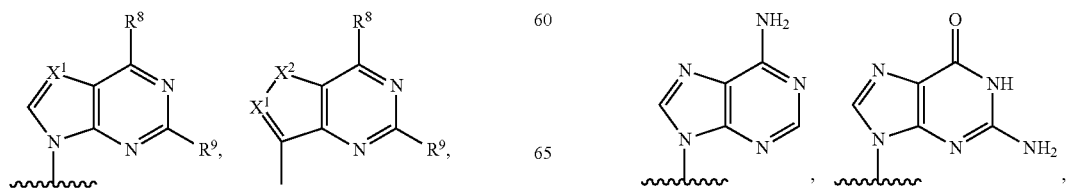

,

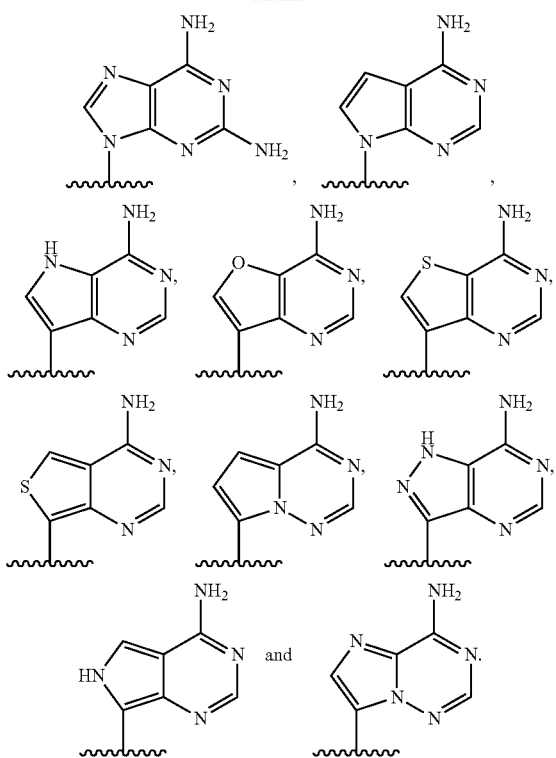

In another aspect of this embodiment, Base is selected from the group

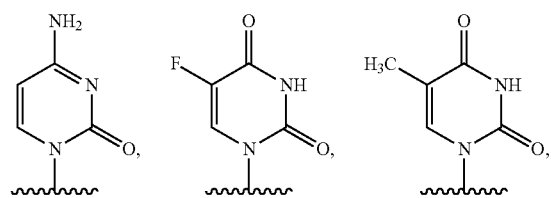

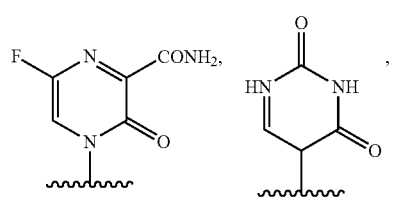

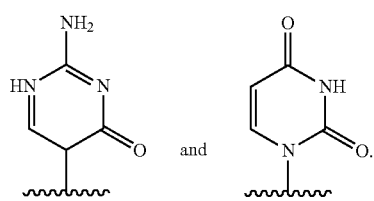

In another aspect of this embodiment, Base is selected from the group

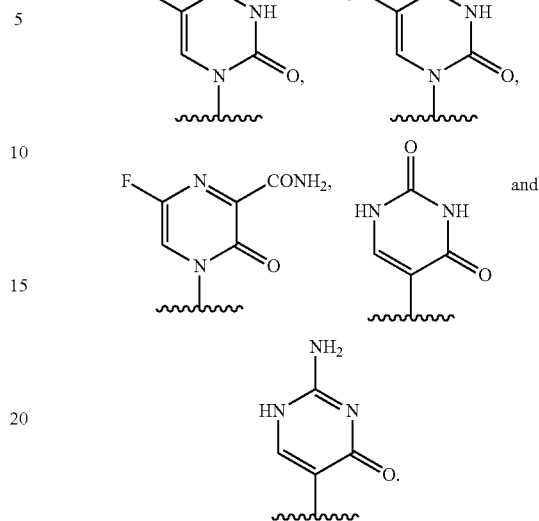

In another embodiment of the method for preparing a compound of Formula IVa or IVb from a compound of Formula V, $R^1$ is H, halogen or $CH_3$; $R^2$ is $OR^{11}$ or halogen; $R^6$ is optionally substituted $(C_1\text{-}C_8)$alkyl or $(C_3\text{-}C_8)$carbocyclyl; one of $R^c$ and $R^d$ is H and the other one is optionally substituted $(C_1\text{-}C_8)$alkyl; $R^{22}$ is $OR^{11}$, and each $R^5$, $R^{23}$ and $R^{24}$ is H. In another aspect of this embodiment, $R^1$ is H. In another aspect of this embodiment, $R^1$ is Cl. In another aspect of this embodiment, $R^1$ is $CH_3$. In another aspect of this embodiment, $R^2$ is F. In another aspect of this embodiment, $R^2$ is OH. In another aspect of this embodiment, $R^2$ is Cl. In another aspect of this embodiment, $R^{22}$ is OH. In another aspect of this embodiment, each $R^2$ and $R^{22}$ is OH. In another aspect of this embodiment, $R^7$ is H. In another aspect of this embodiment, $R^7$ is $CH_3$. In another aspect of this embodiment, $R^7$ is ethynyl. In another aspect of this embodiment, $R^7$ is CN. In another aspect of this embodiment, $R^4$ is optionally substituted $(C_6\text{-}C_{20})$aryl. In another aspect of embodiment, $R^4$ is optionally substituted phenyl. In another aspect of this embodiment, $R^4$ is optionally substituted napthyl. In another aspect of this embodiment, Ar is optionally substituted phenyl. In another aspect of this embodiment, Base is selected from the group consisting of:

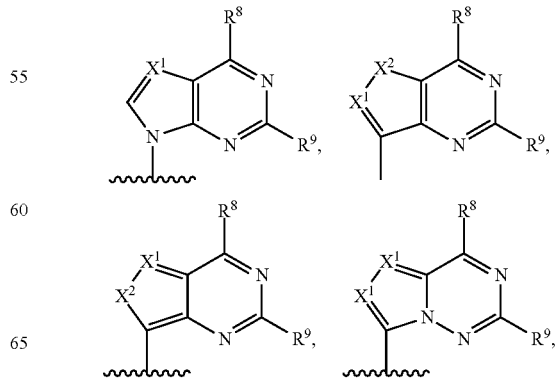

-continued

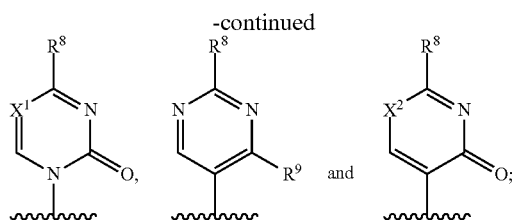

wherein: each $X^1$ is independently N or $CR^{10}$;

each $X^2$ is independently $NR^{11}$, O, or $S(O)_n$;

each $R^8$ is independently halogen, $NR^{11}R^{12}$, $N(R^{11})OR^{11}$, $NR^{11}NR^{11}R^{12}$, $N_3$, NO, $NO_2$, CHO, ON, —CH(=$NR^{11}$), —CH=$NNHR^{11}$, —CH=$N(OR^{11})$, —CH($OR^1$)$_2$, —C(=O)$NR^{11}R^{12}$, —C(=S)$NR^{11}R^{12}$, C(O)$OR^{11}$, ($C_1$-$C_8$) alkyl, ($C_2$-$C_8$)alkenyl, ($C_2$-$C_8$)alkynyl, ($C_4$-$C_8$)carbocyclyl-alkyl, ($C_6$-$C_{20}$)aryl, heterocyclyl, heteroaryl, —C(=O)($C_1$-$C_8$)alkyl, —S(O)$_n$($C_1$-$C_8$)alkyl, aryl($C_1$-$C_8$)alkyl, $OR^{11}$ or $SR^{11}$;

each n is independently 0, 1, or 2;

each $R^9$ or $R^{10}$ is independently H, halogen, $NR^{11}R^{12}$, $N(R^{11})OR^{11}$, $NR^{11}NR^{11}R^{12}$, $N_3$, NO, $NO_2$, CHO, CN, —CH(=$NR^{11}$), —CH=$NHNR^{11}$, —CH=$N(OR^{11})$, —CH($OR^{11}$)$_2$, —C(=O)$NR^{11}R^{12}$, —C(=S)$NR^{11}R^{12}$, —C(=O)$OR^{11}$, $R^{11}$, $OR^{11}$ or $SR^{11}$; each $R^{11}$ or $R^{12}$ is independently H, ($C_1$-$C_8$)alkyl, ($C_2$-$C_8$)alkenyl, ($C_2$-$C_8$)alkynyl, ($C_3$-$C_8$)car-bocyclyl, ($C_4$-$C_8$)carbocyclylalkyl, aryl($C_1$-$C_8$)alkyl, het-erocyclyl($C_1$-$C_8$)alkyl, ($C_6$-$C_{20}$)aryl, heterocyclyl, het-eroaryl, —C(=O)($C_1$-$C_8$)alkyl, —S(O)$_n$($C_1$-$C_8$)alkyl or $R^{11}$ and $R^{12}$ taken together with a nitrogen to which they are both attached form a 3 to 7 membered heterocyclic ring wherein any one carbon atom of said heterocyclic ring can optionally be replaced with —O—, —S(O)$_n$— or —$NR^a$—;

wherein each ($C_1$-$C_8$)alkyl, ($C_2$-$C_8$)alkenyl, ($C_2$-$C_8$)alkynyl, ($C_3$-$C_8$)carbocyclyl, ($C_4$-$C_8$)carbocyclylalkyl, aryl($C_1$-$C_8$) alkyl, heterocyclyl($C_1$-$C_8$)alkyl, ($C_6$-$C_{20}$)aryl, heterocyclyl or heteroaryl of each $R^c$, $R^d$, $R^1$, $R^2$, $R^{22}$, $R^{23}$, $R^{24}$, $R^4$, $R^5$, $R^6$, $R^7$, $R^8$, $R^9$, $R^{10}$, $R^{11}$ or $R^{12}$ is, independently, optionally substituted with one or more halo, hydroxy, CN, $N_3$, $N(R^a)_2$, $NH(R^a)$, $NH_2$, $NO_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $C(O)R^a$, $OC(O)R^a$, $S(O)_nR^a$, $S(O)_2N(R^a)_2$, $S(O)_2NH(R^a)$, $S(O)_2NH_2$, $OR^a$ or $R^a$.

In another aspect of this embodiment, Base is selected from the group consisting of:

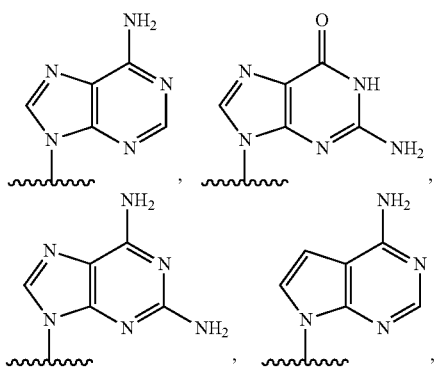

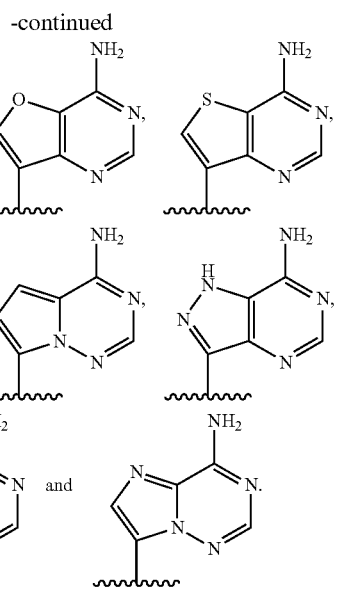

In another aspect of this embodiment, Base is selected from the group

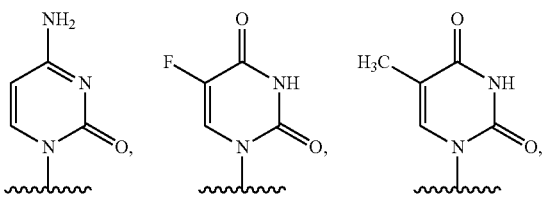

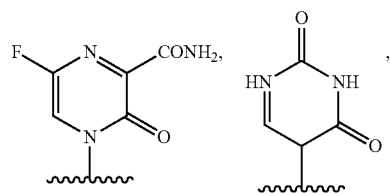

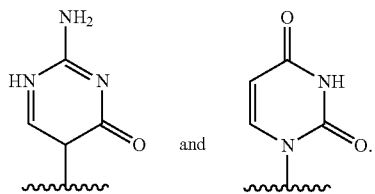

In another aspect of this embodiment, Base is selected from the group

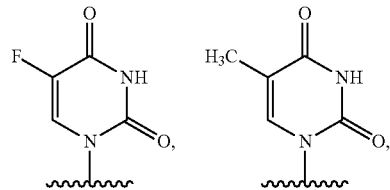

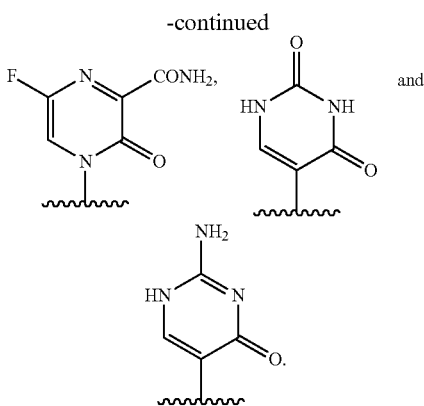

In another embodiment of the method for preparing a compound of Formula IVa or IVb from a compound of Formula V, $R^1$ is H, Cl or $CH_3$; $R^2$ is $OR^{11}$ or halogen; $R^6$ is optionally substituted $(C_1-C_8)$alkyl; one of $R^c$ or $R^d$ is H and the other of $R^c$ or $R^d$ is optionally substituted $(C_1-C_8)$alkyl; $R^{22}$ is $OR^{11}$, each $R^5$, $R^{23}$ and $R^{24}$ is H and Base is selected from the group consisting of:

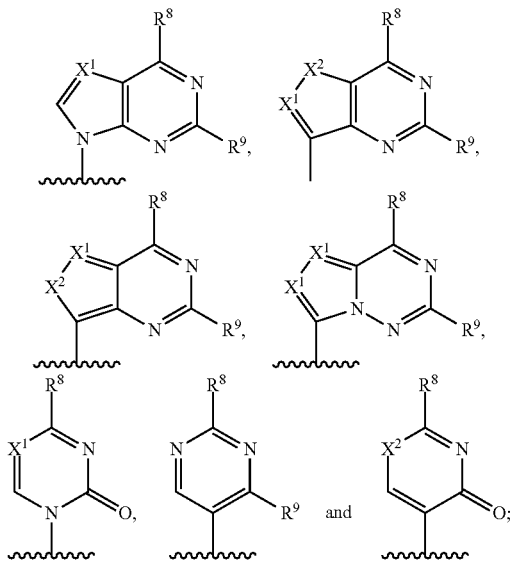

wherein:
each $X^1$ is independently N or $CR^{10}$;
each $X^2$ is independently $NR^{11}$, O, or $S(O)_n$;
each $R^8$ is independently halogen, $NR^{11}R^{12}$, $N(R^{11})OR^{11}$, $NR^{11}NR^{11}R^{12}$, $N_3$, NO, $NO_2$, CHO, CN, —CH(=$NR^{11}$), —CH=$NNHR^{11}$, —CH=$N(OR^{11})$, —$CH(OR^{11})_2$, —C(=O)$NR^{11}R^{12}$, —C(=S)$NR^{11}R^{12}$, —C(O)$OR^{11}$, $(C_1-C_8)$alkyl, $(C_2-C_8)$alkenyl, $(C_2-C_8)$alkynyl, $(C_4-C_8)$carbocyclylalkyl, $(C_6-C_{20})$aryl, heterocyclyl, heteroaryl, —C(=O)$(C_1-C_8)$alkyl, —S(O)$_n(C_1-C_8)$alkyl, aryl$(C_1-C_8)$alkyl, $OR^{11}$ or $SR^{11}$;
each n is independently 0, 1, or 2;
each $R^9$ or $R^{10}$ is independently H, halogen, $NR^{11}R^{12}$, $N(R^{11})OR^{11}$, $NR^{11}NR^{11}R^{12}$, $N_3$, NO, $NO_2$, CHO, CN, —CH(=$NR^{11}$), —CH=$NHNR^{11}$, —CH=$N(OR^{11})$, —$CH(OR^{11})_2$, —C(=O)$NR^{11}R^{12}$, —C(=S)$NR^{11}R^{12}$, —C(=O)$OR^{11}$, $R^{11}$, $OR^{11}$ or $SR^{11}$; each $R^{11}$ or $R^{12}$ is independently H, $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, heterocyclyl, heteroaryl, —C(=O)$(C_1-C_8)$alkyl, —S(O)$_n(C_1-C_8)$alkyl or $R^{11}$ and $R^{12}$ taken together with a nitrogen to which they are both attached form a 3 to 7 membered heterocyclic ring wherein any one carbon atom of said heterocyclic ring can optionally be replaced with —O—, —S(O)$_n$— or —$NR^a$—;
wherein each $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, heterocyclyl or heteroaryl of each $R^c$, $R^d$, $R^1$, $R^2$, $R^{22}$, $R^{23}$, $R^{24}$, $R^4$, $R^5$, $R^6$, $R^7$, $R^8$, $R^9$, $R^{10}$, $R^{11}$ or $R^{12}$ is, independently, optionally substituted with one or more halo, hydroxy, CN, $N_3$, $N(R^a)_2$, $NH(R^a)$, $NH_2$, $NO_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $C(O)R^a$, $OC(O)R^a$, $S(O)_nR^a$, $S(O)_2N(R^a)_2$, $S(O)_2NH(R^a)$, $S(O)_2NH_2$, $OR^a$ or $R^a$.

In another aspect of this embodiment, $R^1$ is H. In another aspect of this embodiment, $R^1$ is $CH_3$. In another aspect of this embodiment, $R^1$ is Cl. In another aspect of this embodiment, $R^2$ is F. In another aspect of this embodiment, $R^2$ is OH. In another aspect of this embodiment, $R^2$ is Cl. In another aspect of this embodiment, $R^1$ is F and $R^2$ is Cl. In another aspect of this embodiment, $R^1$ is $CH_3$ and $R^2$ is Cl. In another aspect of this embodiment, $R^1$ $R^2$ are both Cl. In another aspect of this embodiment, $R^{22}$ is OH. In another aspect of this embodiment, each $R^2$ and $R^{22}$ is OH. In another aspect of this embodiment, $R^7$ is H. In another aspect of this embodiment, $R^7$ is $CH_3$. In another aspect of this embodiment, $R^7$ is ethynyl. In another aspect of this embodiment, $R^7$ is CN. In another aspect of this embodiment, $R^4$ is optionally substituted $(C_6-C_{20})$aryl. In another aspect of this embodiment, $R^4$ is optionally substituted phenyl. In another aspect of this embodiment, $R^4$ is optionally substituted napthyl. In another aspect of this embodiment, one of $R^c$ or $R^d$ is H and the other of $R^c$ or $R^d$ is $CH_3$. In another aspect of this embodiment, Ar is optionally substituted phenyl. In another aspect of this embodiment, Ar is phenyl which is substituted with 1 to 5 halogen atoms. In another aspect of this embodiment, Ar is halo pentafluorophenyl. In another aspect of this embodiment, Ar is 3,5-dichlorophenyl. In another aspect of this embodiment, Base is adenine.

In another aspect of this embodiment, Base is guanine.

In another aspect of this embodiment, Base is 2,6-diaminopurine.

In another aspect of this embodiment, Base is 7-deazaadenine.

In another aspect of this embodiment, Base is

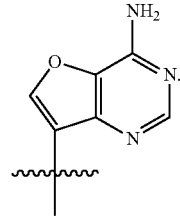

In another aspect of this embodiment, Base is

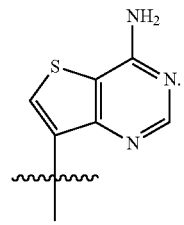

In another aspect of this embodiment, Base is

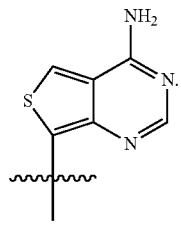 [SMILES: *c1scc2c(N)ncnc12]

In another aspect of this embodiment, Base is

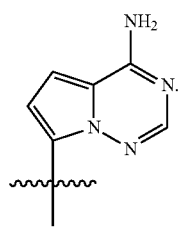 [SMILES: *c1ccc2c(N)ncnn12]

In another aspect of this embodiment, Base is

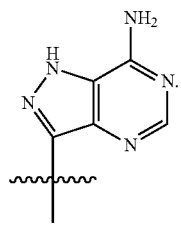 [SMILES: *c1n[nH]c2c(N)ncnc12]

In another aspect of this embodiment, Base is

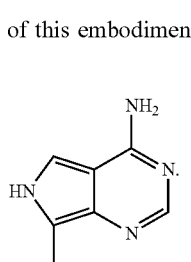

In another aspect of this embodiment, Base is

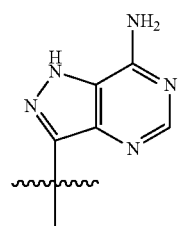 [SMILES: *c1n[nH]c2c(N)ncnc12]

In another aspect of this embodiment, Base is cytosine.
In another aspect of this embodiment, Base is 5-fluorouracil.
In another aspect of this embodiment, Base is thymine.

In another aspect of this embodiment, Base is

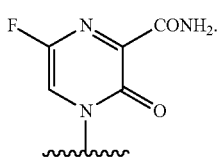

In another aspect of this embodiment, Base is

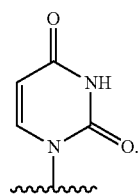 [SMILES: *n1ccc(=O)[nH]c1=O]

In another aspect of this embodiment, Base is

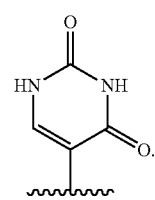 [SMILES: *c1c[nH]c(=O)[nH]c1=O]

In another aspect of this embodiment, Base is

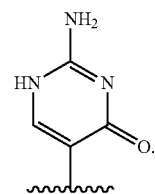 [SMILES: *c1c[nH]c(N)nc1=O]

In another embodiment of the method for preparing a compound of Formula Ia or Ib or a pharmaceutically acceptable salt or ester thereof, Formula Ia is Formula VIa, Formula Ib is Formula VIb and Formula II is Formula VII:

Formula VIa

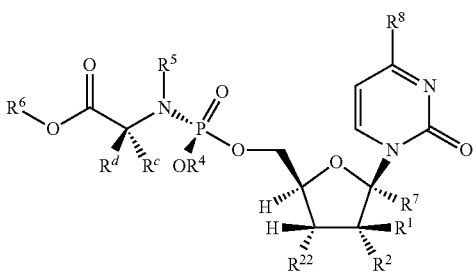

-continued

Formula VIb

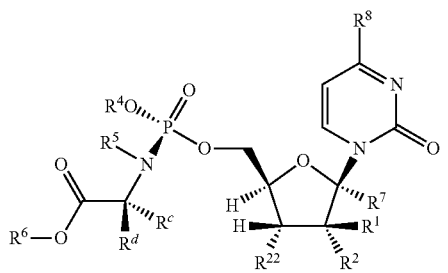

Formula VII

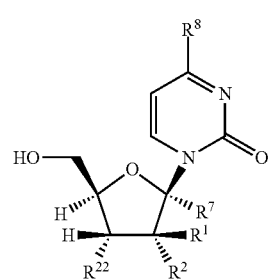

wherein each $R^1$ is independently H, halogen, optionally substituted $(C_1-C_8)$alkyl, optionally substituted $(C_2-C_8)$alkenyl or optionally substituted $(C_2-C_8)$alkynyl;
each $R^2$ is independently halogen or $OR^{11}$;
each $R^5$ is H;
each $R^{22}$ is $OR^{11}$ and
the remaining variables are defined as for Formulae Ia or Ib or II or IIIa or IIIb.

In one embodiment of the method for preparing a compound of Formula VIa or Formula VIb from a compound of Formula VII, $X^1$ is $CR^{10}$. In another aspect of this embodiment, $R^{10}$ is H. In another aspect of this embodiment, $R^1$ is H. In another aspect of this embodiment, $R^1$ is F. In another aspect of this embodiment, $R^1$ is Cl. In another aspect of this embodiment, $R^1$ is optionally substituted $(C_1-C_8)$alkyl. In another aspect of this embodiment, $R^1$ is methyl. In another aspect of this embodiment, $R^1$ is optionally substituted $(C_2-C_8)$alkenyl. In another aspect of this embodiment, $R^1$ is optionally substituted ethenyl. In another aspect of this embodiment, $R^1$ is optionally substituted $(C_2-C_8)$alkynyl. In another aspect of this embodiment, $R^1$ is optionally substituted ethynyl. In another aspect of this embodiment, $R^2$ is F. In another aspect of this embodiment, $R^2$ is Cl. In another aspect of this embodiment, $R^2$ is OH. In another aspect of this embodiment $R^{22}$ is OH. In another aspect of this embodiment, each $R^2$ and $R^{22}$ is OH. In another aspect of this embodiment, $R^7$ is H. In another aspect of this embodiment, $R^7$ is optionally substituted $(C_1-C_8)$alkyl. In another aspect of this embodiment, $R^7$ is optionally substituted $(C_2-C_8)$alkynyl. In another aspect of this embodiment, $R^7$ is CN. In another aspect of this embodiment, one of $R^c$ or $R^d$ is H. In another aspect of this embodiment, one of $R^c$ or $R^d$ is H and the other of $R^c$ or $R^d$ is optionally substituted $(C_1-C_8)$alkyl. In another aspect of this embodiment, $R^6$ is optionally substituted $(C_1-C_8)$alkyl. In another aspect of this embodiment, $R^6$ is $(C_3-C_8)$carbocyclyl. In another aspect of this embodiment, $R^4$ is optionally substituted $(C_6-C_{20})$aryl. In another aspect of this embodiment, Ar is optionally substituted phenyl.

In another embodiment of the method for preparing a compound of Formula VIa or Formula VIb from a compound of Formula VII, $X^1$ is CH, $R^1$ is H, Cl or $CH_3$ and one of $R^c$ or $R^d$ is H. In another aspect of this embodiment, $R^2$ is F. In another aspect of this embodiment, $R^2$ is Cl. In another aspect of this embodiment, $R^2$ is OH. In another aspect of this embodiment $R^{22}$ is OH. In another aspect of this embodiment, each $R^2$ and $R^{22}$ is OH. In another aspect of this embodiment, $R^7$ is H. In another aspect of this embodiment, $R^7$ is optionally substituted $(C_1-C_8)$alkyl. In another aspect of this embodiment, $R^7$ is $CH_3$. In another aspect of this embodiment, $R^7$ is optionally substituted $(C_2-C_8)$alkynyl. In another aspect of this embodiment, $R^7$ is ethynyl. In another aspect of this embodiment, $R^7$ is CN. In another aspect of this embodiment, one of $R^c$ or $R^d$ is H and the other of $R^c$ or $R^d$ is optionally substituted $(C_1-C_8)$alkyl. In another aspect of this embodiment, $R^6$ is optionally substituted $(C_1-C_8)$alkyl. In another aspect of this embodiment, $R^6$ is optionally substituted $(C_3-C_8)$cycloalkyl. In another aspect of this embodiment, $R^4$ is optionally substituted $(C_6-C_{20})$aryl. In another aspect of this embodiment, Ar is optionally substituted phenyl. In another aspect of this embodiment, $R^8$ is $NR^{11}R^{12}$. In another aspect of this embodiment, $R^8$ is $OR^{11}$. In another aspect of this embodiment, $R^8$ is $NH_2$. In another aspect of this embodiment, $R^8$ is OH.

In another embodiment of the method for preparing a compound of Formula VIa or Formula VIb from a compound of Formula VII, $X^1$ is CH, $R^1$ is H, Cl or $CH_3$ one of $R^c$ or $R^d$ is H and $R^7$ is H. In another aspect of this embodiment, $R^2$ is F. In another aspect of this embodiment, $R^2$ is Cl. In another aspect of this embodiment, $R^2$ is OH. In another aspect of this embodiment, $R^1$ is Cl and $R^2$ is F. In another aspect of this embodiment, $R^1$ is $CH_3$ and $R^2$ is Cl. In another aspect of this embodiment, $R^1$ and $R^2$ are both Cl. In another aspect of this embodiment, each $R^2$ and $R^{22}$ is OH. In another aspect of this embodiment, one of $R^c$ and $R^d$ is H and the other of $R^c$ and $R^d$ is optionally substituted $(C_1-C_8)$alkyl. In another aspect of this embodiment, one of $R^c$ and $R^d$ is H and the other of $R^c$ and $R^d$ is $CH_3$. In another aspect of this embodiment, $R^6$ is optionally substituted $(C_1-C_8)$alkyl. In another aspect of this embodiment, $R^6$ is optionally substituted $(C_c-C_8)$cycloalkyl. In another aspect of this embodiment, $R^4$ is optionally substituted $(C_6-C_{20})$aryl. In another aspect of this embodiment, $R^4$ is optionally substituted phenyl. In another aspect of this embodiment, Ar is optionally substituted phenyl. In another aspect of this embodiment, Ar is phenyl which is substituted with 1-5 halogen atoms. In another aspect of this embodiment, Ar is pentafluorophenyl. In another aspect of this embodiment, Ar is 3,5-dichlorophenyl. In another aspect of this embodiment, $R^8$ is $NR^{11}R^{12}$. In another aspect of this embodiment, $R^8$ is $NH_2$. In another aspect of this embodiment, $R^8$ is $OR^{11}$. In another aspect of this embodiment, $R^8$ is OH.

In another embodiment of the method for preparing a compound of Formula Ia or Ib or a pharmaceutically acceptable salt or ester thereof, Formula Ia is Formula VI, Formula Ib is Formula VIb and Formula II is Formula VII:

Formula VIa

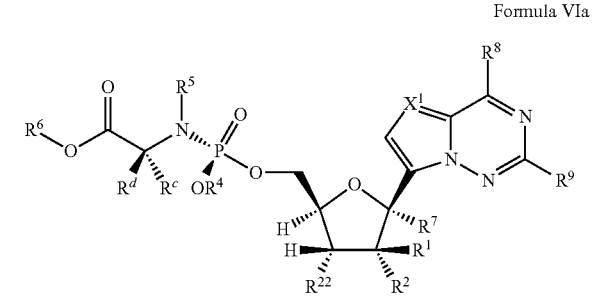

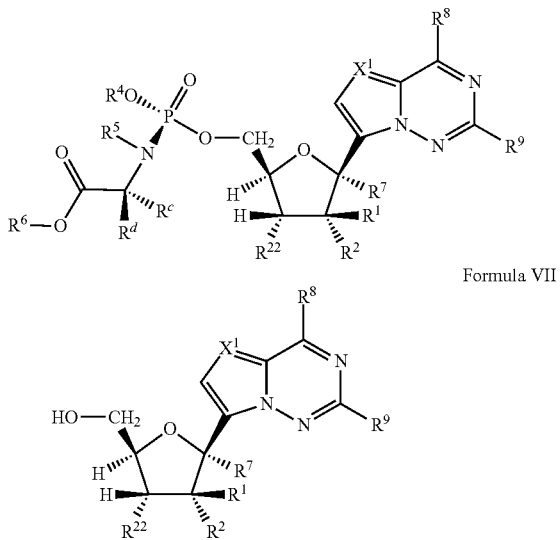

Formula VIb

Formula VII wherein each $R^1$ is independently H, halogen, optionally substituted $(C_1-C_8)$alkyl, optionally substituted $(C_2-C_8)$alkenyl or optionally substituted $(C_2-C_8)$alkynyl;
each $R^2$ is independently halogen or $OR^{11}$;
each $R^5$ is H;
each $R^{22}$ is $OR^{11}$ and
the remaining variables are defined as for Formulae Ia or Ib or II or IIIa or IIIb.

In one embodiment of the method for preparing a compound of Formula VIa or Formula VIb from a compound of Formula VII, $X^1$ is $CR^{10}$. In another aspect of this embodiment, $R^{10}$ is H. In another aspect of this embodiment, $R^1$ is H. In another aspect of this embodiment, $R^1$ is F. In another aspect of this embodiment, $R^1$ is Cl. In another aspect of this embodiment, $R^1$ is optionally substituted $(C_1-C_8)$alkyl. In another aspect of this embodiment, $R^1$ is methyl. In another aspect of this embodiment, $R^1$ is optionally substituted $(C_2-C_8)$alkenyl. In another aspect of this embodiment, $R^1$ is optionally substituted ethenyl. In another aspect of this embodiment, $R^1$ is optionally substituted $(C_2-C_8)$alkynyl. In another aspect of this embodiment, $R^1$ is optionally substituted ethynyl. In another aspect of this embodiment, $R^2$ is F. In another aspect of this embodiment, $R^2$ is Cl. In another aspect of this embodiment, $R^2$ is OH. In another aspect of this embodiment $R^{22}$ is OH. In another aspect of this embodiment, each $R^2$ and $R^{22}$ is OH. In another aspect of this embodiment, $R^7$ is H. In another aspect of this embodiment, $R^7$ is optionally substituted $(C_1-C_8)$alkyl. In another aspect of this embodiment, $R^7$ is optionally substituted $(C_2-C_8)$alkynyl. In another aspect of this embodiment, $R^7$ is CN. In another aspect of this embodiment, one of $R^c$ or $R^d$ is H. In another aspect of this embodiment, one of $R^c$ or $R^d$ is H and the other of $R^c$ or $R^d$ is optionally substituted $(C_1-C_8)$alkyl. In another aspect of this embodiment, $R^6$ is optionally substituted $(C_1-C_8)$alkyl. In another aspect of this embodiment, $R^6$ is optionally substituted optionally substituted $(C_3-C_8)$cycloalkyl. In another aspect of this embodiment, $R^4$ is optionally substituted $(C_6-C_{20})$aryl. In another aspect of this embodiment, Ar is optionally substituted phenyl.

In another embodiment of the method for preparing a compound of Formula VIa or Formula VIb from a compound of Formula VII, $X^1$ is CH, $R^1$ is H, Cl or $CH_3$ and one of $R^c$ or $R^d$ is H. In another aspect of this embodiment, $R^2$ is F. In another aspect of this embodiment, $R^2$ is Cl. In another aspect of this embodiment, $R^2$ is OH. In another aspect of this embodiment $R^{22}$ is OH. In another aspect of this embodiment, each $R^2$ and $R^{22}$ is OH. In another aspect of this embodiment, $R^7$ is H. In another aspect of this embodiment, $R^7$ is optionally substituted $(C_1-C_8)$alkyl. In another aspect of this embodiment, $R^7$ is $CH_3$. In another aspect of this embodiment, $R^7$ is optionally substituted $(C_2-C_8)$alkynyl. In another aspect of this embodiment, $R^7$ is ethynyl. In another aspect of this embodiment, $R^7$ is CN. In another aspect of this embodiment, one of $R^c$ or $R^d$ is H and the other of $R^c$ or $R^d$ is optionally substituted $(C_1-C_8)$alkyl. In another aspect of this embodiment, $R^6$ is optionally substituted $(C_1-C_8)$alkyl. In another aspect of this embodiment, $R^6$ is optionally substituted $(C_3-C_8)$cycloalkyl. In another aspect of this embodiment, $R^4$ is optionally substituted $(C_6-C_{20})$aryl. In another aspect of this embodiment, Ar is optionally substituted phenyl. In another aspect of this embodiment, $R^8$ is $NR^{11}R^{12}$. In another aspect of this embodiment, $R^8$ is $OR^{11}$. In another aspect of this embodiment, $R^8$ is $NH_2$. In another aspect of this embodiment, $R^8$ is OH. In another aspect of this embodiment, $R^9$ is H. In another aspect of this embodiment, $R^9$ is $NR^{11}R^{12}$. In another aspect of this embodiment, $R^9$ is $OR^{11}$. In another aspect of this embodiment, $R^8$ is $NR^{11}N^{12}$ and $R^9$ is H. In another aspect of this embodiment, $R^8$ is $NR^{11}R^{12}$ and $R^9$ is $NR^{11}R^{12}$.

In another embodiment of the method for preparing a compound of Formula VIa or Formula VIb from a compound of Formula VII, $X^1$ is CH, $R^1$ is H, Cl or $CH_3$ one of $R^c$ or $R^d$ is H and $R^7$ is ON. In another aspect of this embodiment, $R^2$ is F. In another aspect of this embodiment, $R^2$ is Cl. In another aspect of this embodiment, $R^2$ is OH. In another aspect of this embodiment, each $R^2$ and $R^{22}$ is OH. In another aspect of this embodiment, one of $R^c$ and $R^d$ is H and the other of $R^c$ and $R^d$ is optionally substituted $(C_1-C_8)$alkyl. In another aspect of this embodiment, one of $R^c$ and $R^d$ is H and the other of $R^c$ and $R^d$ is $CH_3$. In another aspect of this embodiment, $R^6$ is optionally substituted $(C_1-C_8)$alkyl. In another aspect of this embodiment, $R^6$ is optionally substituted $(C_3-C_8)$cycloalkyl. In another aspect of this embodiment, $R^4$ is optionally substituted $(C_6-C_{20})$aryl. In another aspect of this embodiment, $R^4$ is optionally substituted phenyl. In another aspect of this embodiment, Ar is optionally substituted phenyl. In another aspect of this embodiment, $R^8$ is $NR^{11}R^{12}$. In another aspect of this embodiment, $R^8$ is $OR^{11}$. In another aspect of this embodiment, $R^8$ is $NH_2$. In another aspect of this embodiment, $R^9$ is OH. In another aspect of this embodiment, $R^9$ is H. In another aspect of this embodiment, $R^9$ is $NR^{11}R^{12}$. In another aspect of this embodiment, $R^9$ is $OR^1$. In another aspect of this embodiment, $R^8$ is $NR^{11}R^{12}$ and $R^9$ is H. In another aspect of this embodiment, $R^8$ is $NH^2$ and $R^9$ is H. In another aspect of this embodiment, $R^8$ is $NR^{11}R^{12}$ and $R^9$ is $NR^{11}R^{12}$. In another aspect of this embodiment, $R^8$ is $NH_2$ and $R^9$ is $NH_2$. In another aspect of this embodiment, $R^8$ is OH and $R^9$ is $NH_2$.

In one embodiment of the method for preparing a compound of Formula Ia or Ib, Formula Ia is a compound of Formula C2

C2

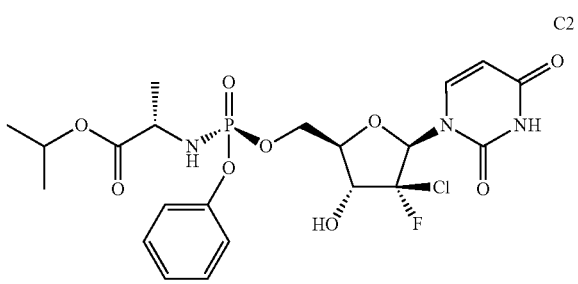 [SMILES: CC(C)OC(=O)[C@H](C)N[P@@](=O)(OC[C@H]1O[C@@H](n2ccc(=O)[nH]c2=O)[C@@](F)(Cl)[C@@H]1O)Oc1ccccc1]

and compound of formula II is

C2k

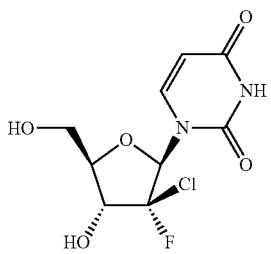

and the compound of formula IIIb is

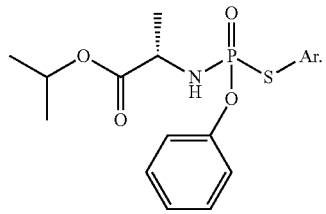

Typically according to this embodiment, Ar is pentafluorophenyl, 4-fluorophenyl, 4-chlorophenyl or 3,5-dichlorophenyl. Preferably, Ar is pentafluorophenyl or 3,5-dichlorophenyl.

In another embodiment of the invention, a method is provided for the preparation of a compound of Formula IIIa or Formula IIIb Formula IIIa

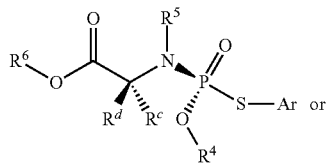

or

Formula IIIb

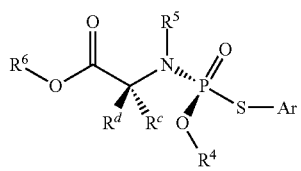

wherein:
each $R^a$, $R^4$ or $R^6$ is independently $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, heterocyclyl or heteroaryl;

each $R^c$ or $R^d$ is independently H, $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl provided that $R^c$ and $R^d$ are not the same;

each $R^5$ is independently H, $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, heterocyclyl or heteroaryl;

wherein each $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, heterocyclyl or heteroaryl of each $R^c$, $R^d$, $R^4$, $R^5$ or $R^6$ is, independently, optionally substituted with one or more halo, hydroxy, CN, $N_3$, $N(R^a)_2$; $NH(R^a)$, $NH_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $S(O)_nR^a$, $S(O)_2N(R^a)_2$, $S(O)_2NH(R^a)$, $S(O)_2NH_2$, $OR^a$ or $R^a$; and each Ar is $(C_6-C_{20})$aryl or a 5 to 20 membered heteroaryl wherein said aryl or heteroaryl is optionally substituted with one or more halogen, $NO_2$, $(C_1-C_8)$haloalkyl, CN, $N_3$, $N(R^a)_2$, $C(O)N(R^a)_2$, $OC(O)N(R^a)_2$, $C(O)OR^a$, $OC(O)OR^a$, $C(O)R^a$, $OC(O)R^a$, $S(O)_nR^a$ $S(O)_2N(R^a)_2$, $OR^a$ or $R^a$ with the proviso that Ar is different from $R^4$;

said method comprising:
(d) providing a diastereomeric compound of Formula VIII

Formula VIII

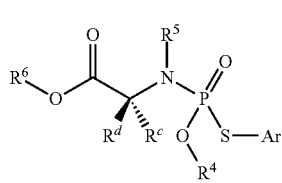

and (e) dissolving the compound of Formula VIII in a suitable solvent and inducing crystallization by cooling the solution; thereby forming a pure diasteromer of Formula IIa or Formula IIIb.

In one embodiment of the method of preparing a compound of Formula IIIa or Formula IIIb, $R^5$ is H and one of $R^c$ or $R^d$ is H. In another aspect of this embodiment, one of $R^c$ or $R^d$ is H and the other of $R^c$ or $R^d$ is optionally substituted $(C_1-C_8)$alkyl. In another aspect of this embodiment, one of $R^c$ or $R^d$ is H and the other of $R^c$ or $R^d$ is $CH_3$. In another aspect of this embodiment, $R^6$ is optionally substituted $(C_1-C_8)$alkyl. In another aspect of this embodiment, $R^6$ is optionally substituted $C_3-C_8$cycoalkyl. In another aspect of this embodiment, $R^6$ is optionally substituted $(C_1-C_8)$ secondary or tertiary alkyl. In another aspect of this embodiment, $R^4$ is optionally substituted $(C_6-C_{20})$ aryl. In another aspect of this embodiment, $R^4$ is optionally substituted phenyl. In another aspect of this embodiment, Ar is optionally substituted phenyl. In another aspect of this embodiment, Ar is phenyl which is substituted with 1 to 5 halogen atoms. In another aspect of this embodiment, Ar is pentafluorophenyl. In another aspect of this embodiment, Ar is 3,5-dichlorophenyl. In another aspect of this embodiment, the chirality at the carbon directly attached to $R^c$ and $R^d$ is S. In another aspect of this embodiment, the chirality at the carbon directly attached to $R^c$ and $R^d$ is R.

In another embodiment of the method of preparing a compound of Formula IIIa or Formula IIIb, $R^5$ is H, one of $R^c$ or $R^d$ is H, $R^6$ is optionally substituted $(C_1-C_8)$alkyl, and $R^4$ is optionally substituted $(C_6-C_{20})$aryl. In another aspect of this embodiment, one of $R^c$ or $R^d$ is H and the other of $R^c$ or $R^d$ is optionally substituted $(C_1-C_8)$alkyl. In another aspect of this embodiment, one of $R^c$ or $R^d$ is H and the other of $R^c$ or $R^d$ is $CH_3$. In another aspect of this embodiment, $R^6$ is optionally substituted $(C_1-C_8)$ secondary or tertiary alkyl. In another aspect of this embodiment, $R^6$ is optionally substituted 2-propyl. In another aspect of this embodiment, $R^4$ is optionally substituted phenyl. In another aspect of this embodiment, Ar is optionally substituted phenyl. In another aspect of this embodiment, Ar is phenyl which is substituted with 1-5 halogens. In another aspect of this embodiment, Ar is pentafluorophenyl. In another aspect of this embodiment, Ar is 3,5-dichlorophenyl. In another aspect of this embodiment, the chirality at the carbon directly attached to $R^c$ and $R^d$ is S. In another aspect of this embodiment, the chirality at the carbon directly attached to $R^c$ and $R^d$ is R.

In another embodiment of the method of preparing a compound of Formula IIIa or Formula IIIb, $R^5$ is H, one of $R^c$ or $R^d$ is H and the other of $R^c$ or $R^d$ is optionally substituted $(C_1-C_8)$alkyl, $R^6$ is optionally substituted $(C_1-C_8)$alkyl, and $R^4$ is optionally substituted phenyl. In another aspect of this embodiment, one of $R^c$ or $R^d$ is H and the other of $R^c$ or $R^d$ is $CH_3$. In another aspect of this embodiment, $R^6$ is optionally substituted $(C_1-C_8)$ secondary or tertiary alkyl. In another aspect of this embodiment, $R^6$ is optionally substituted 2-propyl. In another aspect of this embodiment, $R^4$ is phenyl. In another aspect of this embodiment, Ar is optionally substituted phenyl. In another aspect of this embodiment, Ar is phenyl which is substituted with 1-5 halogen atoms. In another aspect of this embodiment, Ar is pentafluorophenyl. In another aspect of this embodiment, Ar is 3,5-dichlorophenyl. In another aspect of this embodiment, the chirality at the carbon directly attached to $R^c$ and $R^d$ is S. In another aspect of this embodiment, the chirality at the carbon directly attached to $R^c$ and $R^d$ is R.

In another embodiment of the method of preparing a compound of Formula IIIa or Formula IIIb, $R^5$ is H, one of $R^e$ or $R^d$ is H and the other of $R^c$ or $R^d$ is $CH_3$, $R^6$ is optionally substituted $(C_1-C_8)$alkyl, and $R^4$ is optionally substituted phenyl. In another aspect of this embodiment, $R^6$ is optionally substituted $(C_1-C_8)$secondary or tertiary alkyl. In another aspect of this embodiment, $R^6$ is optionally substituted 2-propyl. In another aspect of this embodiment, $R^6$ is 2-propyl. In another aspect of this embodiment, $R^4$ is phenyl. In another aspect of this embodiment, Ar is optionally substituted phenyl. In another aspect of this embodiment, Ar is phenyl which is substituted with 1-5 halogen atoms. In another aspect of this embodiment, Ar is pentafluorophenyl. In another aspect of this embodiment, Ar is 3,5-dichlorophenyl. In another aspect of this embodiment, the chirality at the carbon directly attached to $R^c$ and $R^d$ is S. In another aspect of this embodiment, the chirality at the carbon directly attached to $R^c$ and $R^d$ is R.

The diastereomeric mixture of the compound of Formula VIII is typically resolved by crystallization of the compound of Formula VIII from a suitable solvent. Non-limiting examples of suitable solvents are diethyl ether, dipropyl ether, di i-butyl ether, methyl i-butyl ether, $C_1-C_6$halogenated alkanes, $C_5-C_8$hydrocarbons, tetrahydrofuran, toluene, xylene, dioxane and the like. In another embodiment, the compound of Formula VIII is dissolved in a suitable solvent and crystallization is induced by addition of a $C_5-C_8$hydrocarbon or $C_5-C_8$ cyclic hydrocarbon. In one embodiment, the compound of Formula VIII is dissolved in an ether solvent and crystallization is induced by addition of a $C_5-C_8$ hydrocarbon. In a typical embodiment, the compound of Formula VIII is dissolved in diethyl ether and crystallization is induced by the addition of hexane.

In a further embodiment, the compound of Formula VIII is dissolved in a $C_5-C_8$hydrocarbon and crystallization is induced by cooling the solution. In a preferred embodiment, the compound of Formula VIII is dissolved in hexane or heptane and crystallization is induced by cooling the solution.

The diastereomeric mixture of the compound of Formula VIII is typically resolved by crystallization of the compound of Formula VIII from a suitable solvent at a temperature of about 80° C. to about −20° C. Preferably, the temperature is about 30° C. to about −20° C., more preferably about ambient to −10° C.

The diastereomeric mixture of the compound of Formula VIII is typically resolved by crystallization of the compound of Formula VIII from a suitable solvent wherein the concentration of the compound of Formula VIII in solution is about 25 g to about 1000 g per liter of solvent. More typically, the concentration of the compound of Formula VIII is about 50 to 500 g per liter of solvent. The resolution of the diastereomeric mixture of the compound of Formula VIII by crystallization may be promoted by the addition of seed crystals of the pure diastereomer. Seed crystals of pure diastereomers may be obtained through purification of the diastereomeric mixture of the compound of Formula VIII by liquid chromatography, chiral liquid chromatography, high pressure liquid chromatography, or chiral high pressure liquid chromatography such as by the non-limiting methods described herein.

Typically, the crystallization of the diastereomeric mixture of the compound of Formula VIII produces a mixture of diastereomers containing at least 60% of a single diastereomer. More typically, the mixture produced contains at least 70% of a single diastereomer, most typically, at least 80% of a single diastereomer, preferably at least 90% of a single diastereomer, and more preferably at least 95% of a single diastereomer. Higher diastereomeric purity, for example at least 99% diastereomeric purity, may be obtained by one or more subsequent crystallizations. The yield of crystalline material from a single crystallization is typically about 10 to 45%, more typically about 20-35%.

In another embodiment, a compound of formula VIII

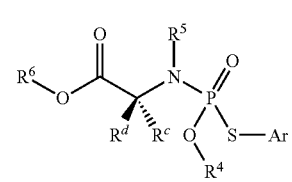

Formula VIII is prepared as illustrated in the scheme 1:

Scheme 1

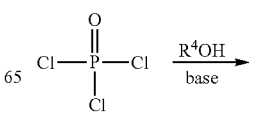

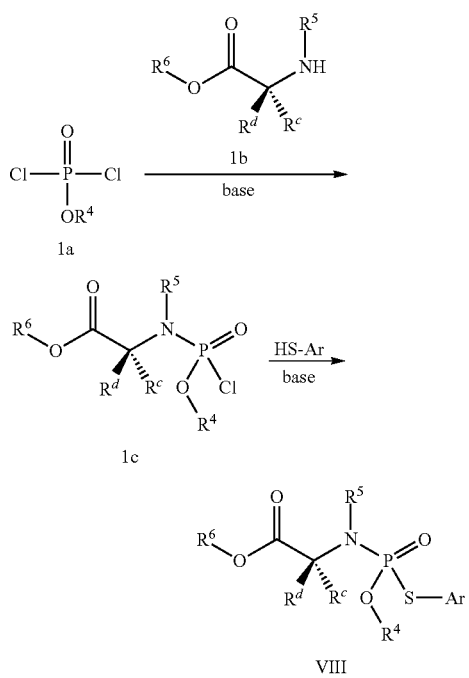

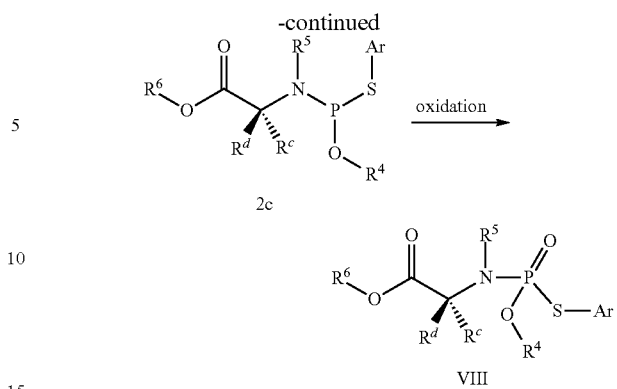

X is a halogen

Condensation of phosphoryl trichloride with a desired alcohol $R^4OH$ in the presence of a base such as $Et_3N$ or DIEA or similar in an inert solvent like dichloromethane, diethyl ether, tetrahydrofuran or the like, followed by reaction with an amino acid derivative (1b) in the presence of a base like $Et_3N$ or DIEA or similar provides the chlorophosphoramidate (1c). The obtained chlorophosphoramidate is then converted to the phosphorylating agent (VIII) by reaction with the desired thiophenol Ar—SH in the presence of a base like triethylamine or similar.

Alternatively, the synthesis of a compound of formula VIII can start from a phosphorus trihalide, and oxidation to the desired phosphate performed as the last step. This method is illustrated in Scheme 2.

Scheme 2

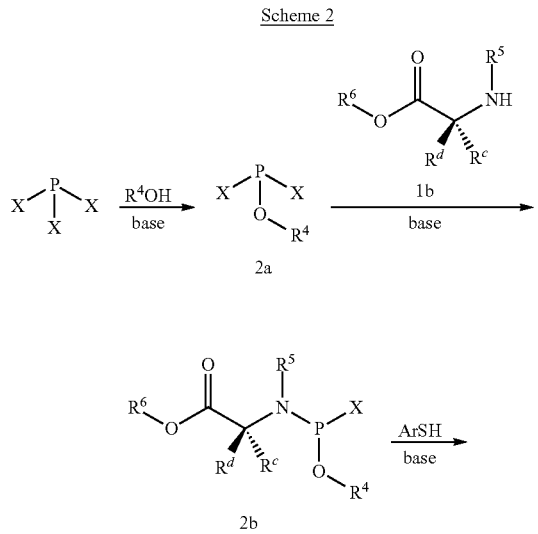

Reaction of phosphorus trihalide with the desired alcohol $R^4$—OH in an inert solvent such as dichloromethane, or an ether like diethyl ether or tetrahydrofuran or the like, in the presence of a base such as triethylamine or similar followed by reaction with an amino acid derivative (1b) in the presence of a base like $Et_3N$ or DIEA or similar provides the phosphinamine 2b. Displacement of the remaining halo atom with a thioaryl or thioheteroaryl derivative ArSH, carried out in a solvent like DCM or similar in the presence of a base such as $Et_3N$ or similar, provides the thio detivative (2d). Oxidation finally, effected for instance by treatment with mCPBA, tert-butylhydroperoxide or any other convenient oxidation agent, provides the phosphoramidate reagent (VIII).

In another embodiment, a compound of Formula IIIa or Formula IIIb is provided

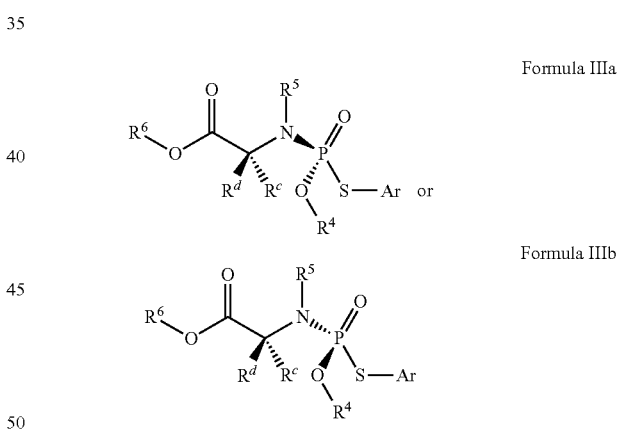

or a salt or ester thereof;
wherein:
each $R^a$, $R^4$ or $R^6$ is independently $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, heterocyclyl or heteroaryl;
each $R^c$ or $R^d$ is independently H, $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, heterocyclyl or heteroaryl;
each $R^5$ is independently H, $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, heterocyclyl or heteroaryl;
wherein each $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$ alkyl, heterocyclyl($C_1$-$C_8$)alkyl, ($C_6$-$C_{20}$)aryl, heterocyclyl or heteroaryl of each $R^c$, $R^d$, $R^4$, $R^5$ or $R^6$ is, independently, optionally substituted with one or more halo, hydroxy, CN, $N_3$, $N(R^a)_2$, $NH(R^a)$, $NH_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $S(O)_nR^a$, $S(O)_2N(R^a)_2$, $S(O)_2NH(R^a)$, $S(O)_2NH_2$, $OR^a$ or $R^a$; and each Ar is a ($C_6$-$C_{20}$)aryl or a 5 to 20 membered heteroaryl wherein said aryl or heteroaryl is optionally substituted with one or more halogen, $NO_2$, ($C_1$-$C_8$)haloalkyl, CN, $N_3$, $N(R^a)_2$; $C(O)N(R^a)_2$, $OC(O)N(R^a)_2$, $C(O)OR^a$, $OC(O)OR^a$, $C(O)R^a$, $OC(O)R^a$, $S(O)_nR^a$, $S(O)_2N(R^a)_2$, $OR^a$ or $R^a$ with the proviso that Ar is different from $R^4$.

In another embodiment of the compound of Formula IIIa or Formula IIIb, $R^5$ is H and one of $R^c$ or $R^d$ is H. In another aspect of this embodiment, one of $R^c$ or $R^d$ is H and the other of $R^c$ or $R^d$ is optionally substituted ($C_1$-$C_8$)alkyl. In another aspect of this embodiment, one of $R^c$ or $R^d$ is H and the other of $R^c$ or $R^d$ is $CH_3$. In another aspect of this embodiment, $R_6$ is optionally substituted ($C_1$-$C_8$)alkyl. In another aspect of this embodiment, $R_6$ is optionally substituted ($C_3$-$C_8$)cycloalkyl. In another aspect of this embodiment, $R^6$ is optionally substituted ($C_1$-$C_8$) secondary or tertiary alkyl. In another aspect of this embodiment, $R^4$ is optionally substituted ($C_6$-$C_{20}$)aryl. In another aspect of this embodiment, $R^4$ is optionally substituted phenyl. In another aspect of this embodiment, Ar is optionally substituted phenyl. In another aspect of this embodiment, Ar is phenyl which is substituted with 1-5 halogen atoms. In another aspect of this embodiment, Ar is pentafluorophenyl. In another aspect of this embodiment, Ar is 3,5-dichlorophenyl. In another aspect of this embodiment, the chirality at the carbon directly attached to $R^c$ and $R^d$ is S. In another aspect of this embodiment, the chirality at the carbon directly attached to $R^c$ and $R^d$ is R. In another aspect of this embodiment, the moiety

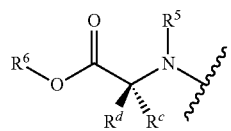

of Formula IIIa or Formula IIIb comprises a nitrogen-linked ester of a naturally occurring a-amino acid.

In another embodiment of the compound of Formula IIIa or Formula IIIb, $R^5$ is H, one of $R^c$ or $R^d$ is H, $R^6$ is optionally substituted ($C_1$-$C_8$)alkyl and $R^4$ is optionally substituted ($C_6$-$C_{20}$)aryl. In another aspect of this embodiment, one of $R^c$ or $R^d$ is H and the other of $R^c$ or $R^d$ is optionally substituted ($C_1$-$C_8$)alkyl. In another aspect of this embodiment, one of $R^c$ or $R^d$ is H and the other is $CH_3$. In another aspect of this embodiment, $R^6$ is optionally substituted ($C_1$-$C_8$) secondary or tertiary alkyl. In another aspect of this embodiment, $R^6$ is optionally substituted 2-propyl. In another aspect of this embodiment, $R^4$ is optionally substituted phenyl. In another aspect of this embodiment, Ar is optionally substituted phenyl. In another aspect of this embodiment, Ar is henyl which is substituted with 1-5 halogen atoms. In another aspect of this embodiment, Ar is pentafluorophenyl. In another aspect of this embodiment, Ar is 3,5-dichlorophenyl. In another aspect of this embodiment, the chirality at the carbon directly attached to $R^c$ and $R^d$ is S. In another aspect of this embodiment, the chirality at the carbon directly attached to $R^c$ and $R^d$ is R. In another aspect of this embodiment, the moiety

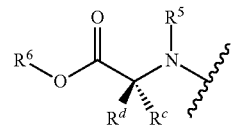

of Formula IIIa or Formula IIIIb comprises a nitrogen-linked ester of a naturally occurring α-amino acid.

In another embodiment of the compound of Formula IIIa or Formula IIIb, $R^5$ is H, one of $R^c$ or $R^d$ is H and the other of $R^c$ or $R^d$ is optionally substituted ($C_1$-$C_8$)alkyl, $R^6$ is optionally substituted ($C_1$-$C_8$)alkyl and $R^4$ is optionally substituted phenyl. In another aspect of this embodiment, one of $R^c$ or $R^d$ is H and the other is $CH_3$. In another aspect of this embodiment, $R^6$ is optionally substituted ($C_1$-$C_8$) secondary or tertiary alkyl. In another aspect of this embodiment, $R^6$ is optionally substituted 2-propyl. In another aspect of this embodiment, $R^4$ is phenyl. In another aspect of this embodiment, Ar is optionally substituted phenyl. In another aspect of this embodiment, Ar is phenyl which is substituted with 1-5 halogen atoms. In another aspect of this embodiment, Ar is pentafluorophenyl. In another aspect of this embodiment, Ar is 3,5-dichlorophenyl. In another aspect of this embodiment, the chirality at the carbon directly attached to $R^c$ and $R^d$ is S. In another aspect of this embodiment, the chirality at the carbon directly attached to $R^c$ and $R^d$ is R. In another aspect of this embodiment, the moiety

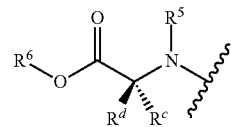

of Formula IIIa or Formula IIIb comprises a nitrogen-linked ester of a naturally occurring α-amino acid.

In another embodiment of the compound of Formula IIIa or Formula IIIb $R^5$ is H, one of $R^c$ or $R^d$ is H and the other of $R^c$ or $R^d$ is $CH_3$, $R^6$ is optionally substituted ($C_1$-$C_8$)alkyl, and $R^4$ is optionally substituted phenyl. In another aspect of this embodiment, $R^6$ is optionally substituted ($C_1$-$C_8$) secondary or tertiary alkyl. In another aspect of this embodiment, $R^6$ is optionally substituted 2-propyl. In another aspect of this embodiment, $R^6$ is 2-propyl. In another aspect of this embodiment, $R^4$ is phenyl. In another aspect of this embodiment, Ar is optionally substituted phenyl. In another aspect of this embodiment, Ar is phenyl which is substituted with 1-5 halogen atoms. In another aspect of this embodiment, Ar is pentafluorophenyl. In another aspect of this embodiment, Ar is 3,5-dichlorophenyl. In another aspect of this embodiment, the chirality at the carbon directly attached to $R^c$ and $R^d$ is S. In another aspect of this embodiment, the chirality at the carbon directly attached to $R^c$ and $R^d$ is R. In another aspect of this embodiment, the moiety

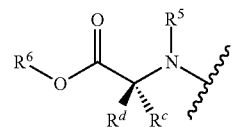

of Formula IIIa or Formula IIIb comprises a nitrogen-linked ester of a naturally occurring α-amino acid.

In one embodiment, a compound of Formula IIIa is provided

Formula IIIa

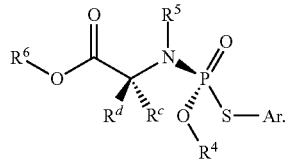

In another embodiment, a compound of Formula IIIb is provided

Formula IIIb

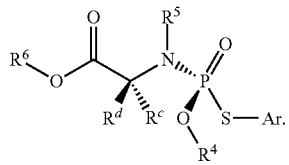

In one embodiment of the compound of formula VIII or diastereomer of formula IIIa or IIIb, $R^5$ is H and one of $R^c$ and $R^d$ is H.

In one embodiment of the compound of formula VIII or diastereomer of formula IIIa or IIIb, $R^6$ is optionally substituted $(C_1-C_8)$alkyl or $(C_3-C_8)$cycloalkyl. In one aspect of this embodiment, $R^6$ is methyl, ethyl, 1-methylbutyl, 2-ethylbutyl, cyclopentyl or preferably isopropyl.

In one embodiment of the compound of formula VIII or diastereomer of formula IIIa or IIIb, $R^4$ is phenyl.

In one embodiment of the compound of formula VIII or diastereomer of formula IIIa or IIIb, one of $R^c$ and $R^d$ is H and the other one is $CH_3$. In one aspect of this embodiment, the stereochemistry at the chiral center to which $R^c$ and $R^d$ are attached, is S, i.e. that of an L-amino acid.

In one embodiment of the compound of formula VIII or diastereomer of formula IIIa or IIIb, Ar is 3,5-dichlorophenyl or pentafluorophenyl.

In another embodiment, compounds of Formula IIIa or Formula IIIb are provided which compounds are selected from the group consisting of:

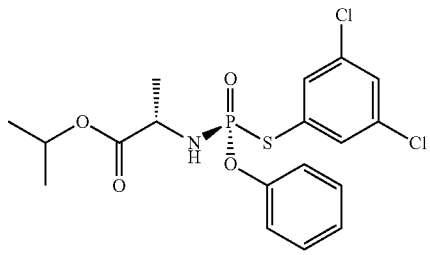

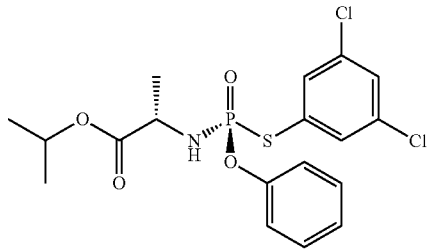

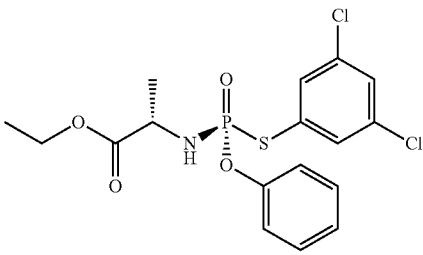

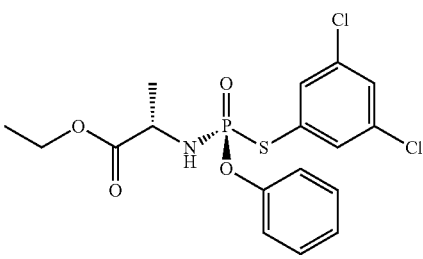

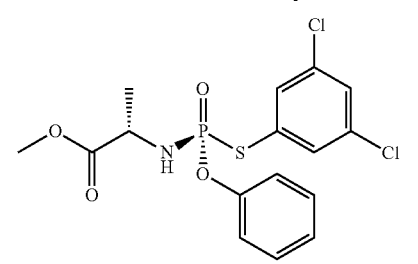

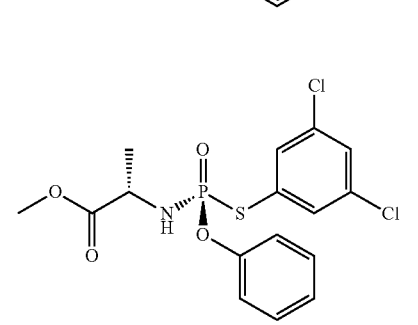

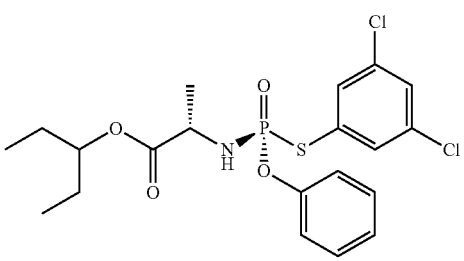

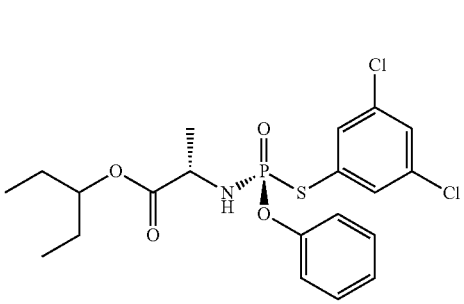

33
-continued
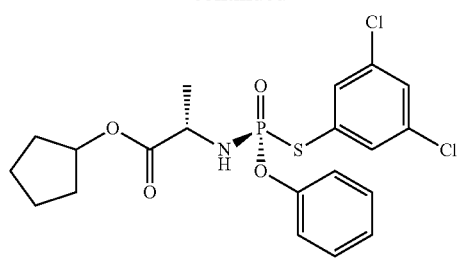
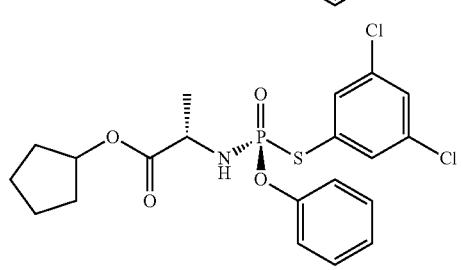
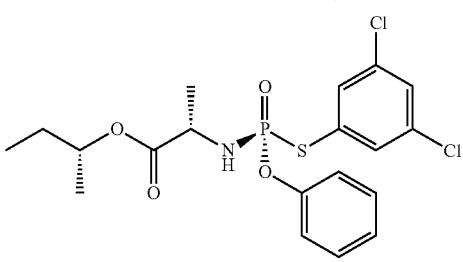
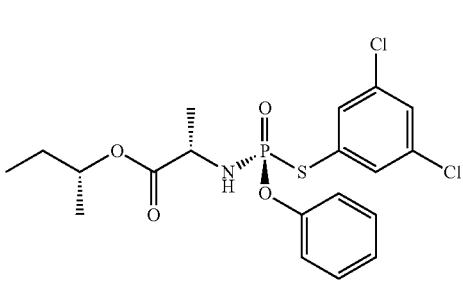
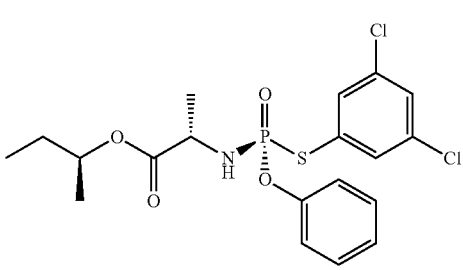
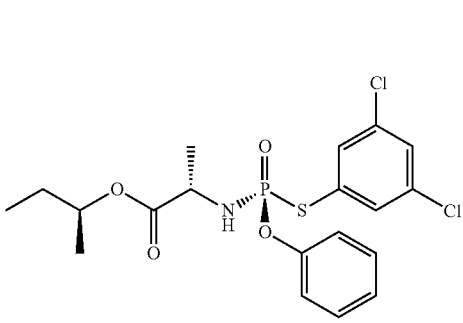
34
-continued
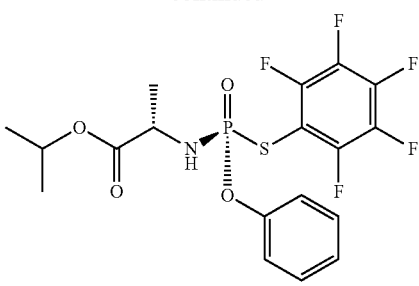
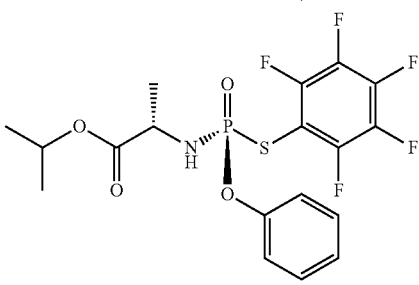
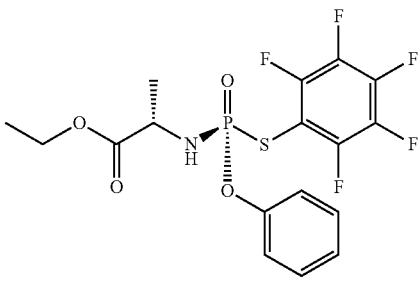
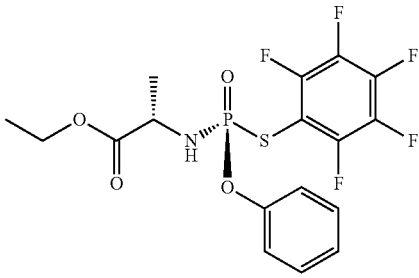
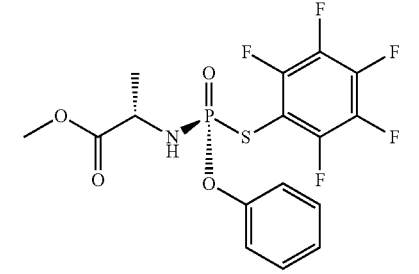
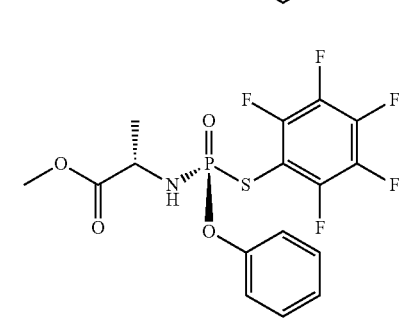

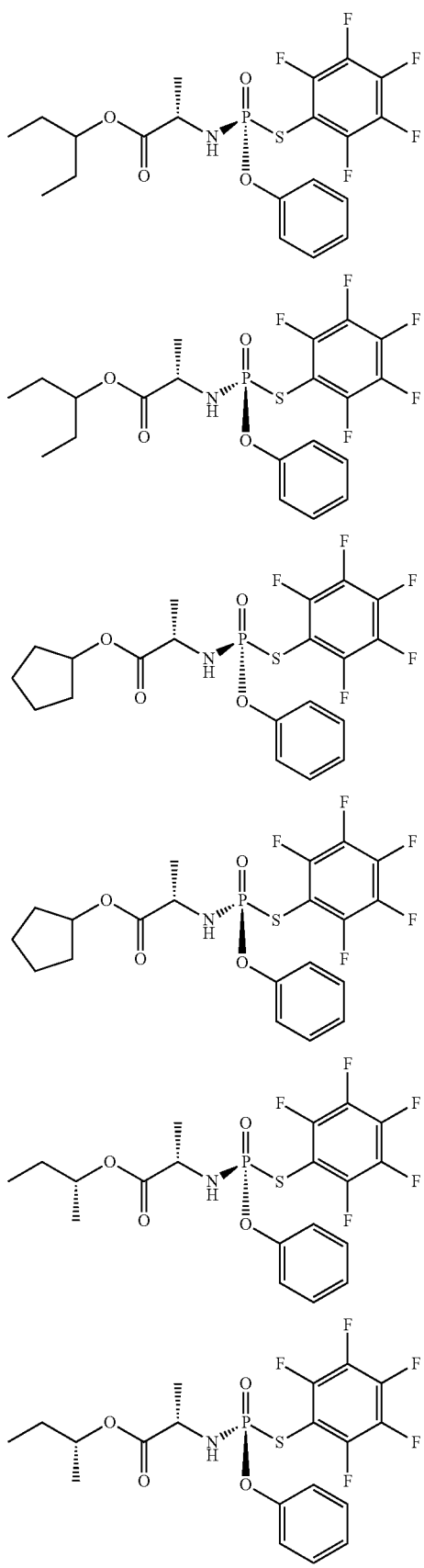

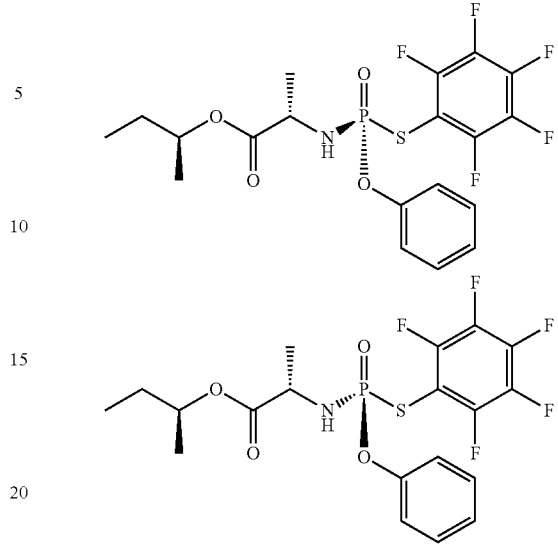

and or salts or esters thereof.

In another embodiment, a method is provided for the preparation of a compound of Formula VIII

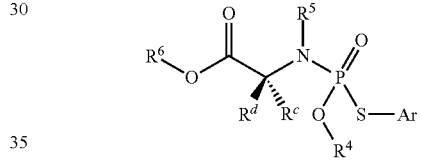

Formula VIII or a salt or ester thereof, wherein each $R^a$, $R^4$ or $R^6$ is independently $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, heterocyclyl or heteroaryl;

each $R^c$ or $R^d$ is independently H, $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, heterocyclyl or heteroaryl provided that $R^c$ and $R^d$ are not the same;

each $R^5$ is independently H, $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, heterocyclyl or heteroaryl;

wherein each $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, heterocyclyl or heteroaryl of each $R^c$, $R^d$, $R^4$, $R^5$ or $R^6$ is, independently, optionally substituted with one or more halo, hydroxy, CN, $N_3$, $N(R^a)_2$, $NH(R^a)$, $NH_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $S(O)_nR^a$ $S(O)_2N(R^a)_2$, $S(O)_2NH(R^a)$, $S(O)_2NH_2$, $OR^a$ or $R^a$; and each Ar is $(C_6-C_{20})$aryl or a 5 to 20 membered heteroaryl wherein said aryl or heteroaryl is optionally substituted with one or more halogen, $NO_2$, $(C_1-C_8)$haloalkyl, CN, $N_3$, $N(R^a)_2$) $C(O)N(R^a)_2$, $OC(O)N(R^a)_2$, $C(O)OR^a$, $OC(O)OR^a$, $C(O)R^a$, $OC(O)R^a$, $S(O)_nR^a$, $S(O)_2N(R^a)_2$, $OR^a$ or $R^a$ with the proviso that Ar is different from $R^4$;

said method comprising:
(f) providing a chirally pure amino acid ester of Formula IX or a salt thereof

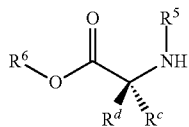

Formula IX (g) treating the compound of Formula IX with a compound of Formula X in the presence of a base

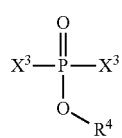

Formula X wherein each $X^3$ is halogen; and
(h) treating the resulting mixture with ArSH; thereby forming a compound of Formula VIII.

Typically, the chirally pure amino acid of Formula IX or a salt thereof is dissolved or suspended in a suitable non-nucleophilic solvent. Non-limiting non-nucleophilic solvents include haloalkanes, e.g. dichloromethane, dichloroethane and ethers, e.g. dioxane, tetrahydrofuran, diethyl ether and glymes. Typically, the suspension or solution contains about 0.1 to about 5 moles of the compound of Formula IX per liter of solvent.

The suspension or solution of the chirally pure amino acid of Formula IX is treated with a compound of Formula X. Typically, the reaction is conducted at about −20 to about 60° C. The mole ratio of the compound of Formula IX to the compound of Formula X is about 1:2 to about 2:1, preferably about 1:1. The reaction is generally conducted in the presence of a non-nucleophilic base. Non-limiting examples of non-nucleophilic bases are tertiary amines, e.g. diisopropylethylamine and triethylamine; metal hydrides, e.g. LiH, NaH and $CaH_2$; and nitrogen containing heterocycles, e.g. pyridine and dimethylaminopyridine. In a preferred embodiment, the base is a tertiary amine such as triethylamine. When the compound of Formula IX is a salt of a monoprotic acid, the molar ratio of base to the compound of Formula IX is typically about 2:1. If the compound of Formula IX is a free base, the molar ratio of base to the compound of Formula IX is about 1:1.

The reaction of the compound of Formula IX with the compound of Formula X may be followed by many conventional means known to those skilled in the art. Such means include thin-layer chromatography and hplc. When the reaction between the compound Formula IX and the compound of Formula X is complete, the reaction is treated with a thiophenolic compound ArSH where Ar is defined as herein. The mole ratio of the compound of Formula X to ArSH is typically about 1.1:1 to about 1:1.1, preferably about 1:1. After the addition of ArSH, additional base is required, typically enough base to neutralize the acid generated in the reaction. Typically, the additional base is a non-nucleophilic base such as described above.

The compound of Formula VIII is isolated by conventional means known to those skilled in the art. For example, the salt formed in the reaction may be precipitated from the reaction mixture and the compound of Formula VIII isolated by evaporation of the solvent followed by crystallization or chromatography.

In one embodiment of the method of preparing a compound of Formula VIII, $R^5$ is H and one of $R^c$ or $R^d$ is H. In another aspect of this embodiment, one of $R^c$ or $R^d$ is H and the other is optionally substituted $(C_1-C_8)$alkyl. In another aspect of this embodiment, one of $R^c$ or $R^d$ is H and the other of $R^c$ or $R^d$ is $CH_3$. In another aspect of this embodiment, $R^6$ is optionally substituted $(C_1-C_8)$alkyl. In another aspect of this embodiment, $R^6$ is optionally substituted $(C_1-C_8)$ secondary or tertiary alkyl. In another aspect of this embodiment, $R^6$ is $(C_3-C_8)$ cycloalkyl. In another aspect of this embodiment, $R^4$ is optionally substituted $(C_6-C_{20})$aryl. In another aspect of this embodiment, $R^4$ is optionally substituted phenyl. In another aspect of this embodiment, Ar is optionally substituted phenyl. In another aspect of this embodiment, Ar is phenyl which is substituted with 1-5 halogen atoms. In another aspect of this embodiment, Ar is pentafluorophenyl. In another aspect of this embodiment, Ar is 3,5-dichlorophenyl. In another aspect of this embodiment, the chirality at the carbon directly attached to $R^c$ and $R^d$ is S. In another aspect of this embodiment, the chirality at the carbon directly attached to $R^c$ and $R^d$ is R. In another aspect of this embodiment, the compound of Formula IX or salt thereof, is an ester of a naturally occurring α-amino acid.

In another embodiment of the method of preparing a compound of Formula VIII, $R^5$ is H, one of $R^c$ or Rd is H, $R^6$ is optionally substituted $(C_1-C_8)$alkyl, and $R^4$ is optionally substituted $(C_6-C_{20})$aryl. In another aspect of this embodiment, one of $R_c$ or $R_d$ is H and the other is optionally substituted $(C_1-C_8)$alkyl. In another aspect of this embodiment, one of $R^c$ or $R^d$ is H and the other is $CH_3$. In another aspect of this embodiment, $R^6$ is optionally substituted $(C_1-C_8)$ secondary or tertiary alkyl. In another aspect of this embodiment, $R^6$ is optionally substituted 2-propyl. In another aspect of this embodiment, $R^4$ is optionally substituted phenyl. In another aspect of this embodiment, Ar is optionally substituted phenyl. In another aspect of this embodiment, Ar is phenyl which is substituted with 1-5 halogen atoms. In another aspect of this embodiment, Ar is pentafluorophenyl. In another aspect of this embodiment, Ar is 3,5-dichlorophenyl. In another aspect of this embodiment, the chirality at the carbon directly attached to $R^c$ and $R^d$ is S. In another aspect of this embodiment, the chirality at the carbon directly attached to $R^c$ and $R^d$ is R. In another aspect of this embodiment, the compound of Formula IX or salt thereof, is an ester of a naturally occurring α-amino acid.

In another embodiment of the method of preparing a compound of Formula VIII, $R^5$ is H, one of $R^c$ or $R^d$ is H and the other one is optionally substituted $(C_1-C_8)$alkyl, $R^6$ is optionally substituted $(C_1-C_8)$alkyl, and $R^4$ is optionally substituted phenyl. In another aspect of this embodiment, one of $R^c$ or $R^d$ is H and the other one is $CH_3$. In another aspect of this embodiment, $R^6$ is optionally substituted $(C_1-C_8)$ secondary or tertiary alkyl. In another aspect of this embodiment, $R^6$ is optionally substituted 2-propyl. In another aspect of this embodiment, $R^4$ is phenyl. In another aspect of this embodiment, Ar is optionally substituted phenyl. In another aspect of this embodiment, Ar is phenyl which is substituted with 1-5 halogen atoms. In another aspect of this embodiment, Ar is pentafluorophenyl. In another aspect of this embodiment, Ar is 3,5-dichlorophenyl. In another aspect of this embodiment, the chirality at the carbon directly attached to $R^c$ and $R^d$ is S. In another aspect of this embodiment, the chirality at the carbon directly attached to $R^c$ and $R^d$ is R. In another aspect of this embodiment, the compound of Formula IX or salt thereof, is an ester of a naturally occurring alpha-amino acid.

In another embodiment of the method of preparing a compound of Formula VIII, $R^5$ is H, one of $R^c$ or $R^d$ is H and the other of $R^c$ or $R^d$ is CH$_3$, $R^6$ is optionally substituted (C$_1$-C$_8$)alkyl, and $R^4$ is optionally substituted phenyl. In another aspect of this embodiment, $R^6$ is optionally substituted (C$_1$-C$_8$) secondary or tertiary alkyl. In another aspect of this embodiment, $R^6$ is optionally substituted 2-propyl. In another aspect of this embodiment, $R^6$ is 2-propyl. In another aspect of this embodiment, $R^6$ is (C$_3$-C$_8$)carbocyclyl In another aspect of this embodiment, $R^4$ is phenyl. In another aspect of this embodiment, Ar is optionally substituted phenyl. In another aspect of this embodiment, Ar is phenyl which is substituted with 1-5 halogen atoms. In another aspect of this embodiment, Ar is pentafluorophenyl. In another aspect of this embodiment, Ar is 3,5-dichlorophenyl. In another aspect of this embodiment, the chirality at the carbon directly attached to $R^c$ and $R^d$ is S. In another aspect of this embodiment, the chirality at the carbon directly attached to $R^c$ and $R^d$ is R. In another aspect of this embodiment, the compound of Formula IX or salt thereof, is an ester of a naturally occurring α-amino acid.

In another embodiment of the method for preparing a compound of Formula Ia or Ib or a pharmaceutically acceptable salt or ester thereof, Formula Ia is Formula XIa, Formula Ib is Formula XIb and Formula II is Formula XII:

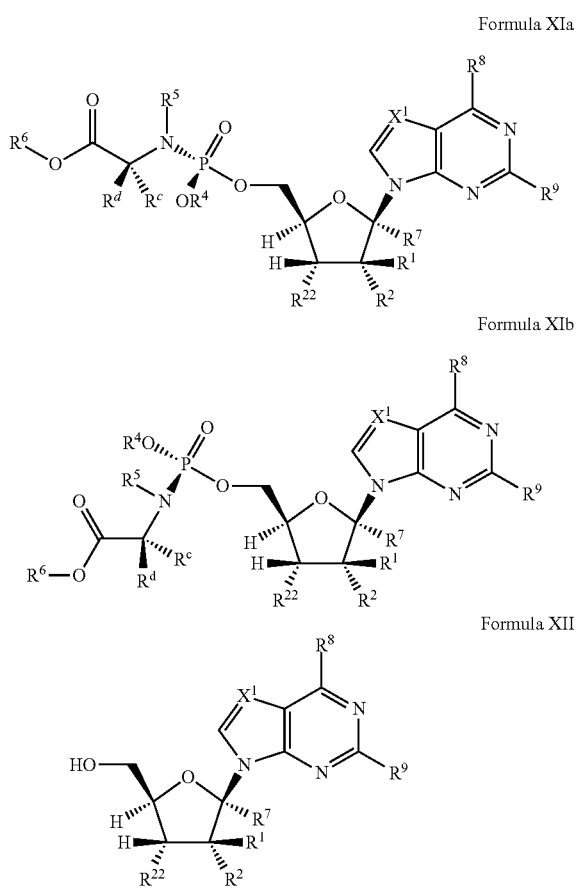

Formula XIa

Formula XIb

Formula XII wherein:
each $R^1$ is independently H, halogen, optionally substituted (C$_1$-C$_8$)alkyl, optionally substituted (C$_2$-C$_8$)alkenyl or optionally substituted (C$_2$-C$_8$)alkynyl; each $R^2$ is independently halogen or OR$^{11}$;

each $R^5$ is H;
each $R^{22}$ is OR$^{11}$; and
the remaining variables are defined as for Formulae Ia or Ib or II or IIIa or IIIb.

In one embodiment of the method for preparing a compound of Formula XIa or Formula XIb from a compound of Formula XII, $X^1$ is CR$^{10}$. In another aspect of this embodiment, $R^{10}$ is H. In another aspect of this embodiment, $R^1$ is H. In another aspect of this embodiment, $R^1$ is F. In another aspect of this embodiment, $R^1$ is Cl. In another aspect of this embodiment, $R^1$ is optionally substituted (C$_1$-C$_8$)alkyl. In another aspect of this embodiment, $R^1$ is methyl. In another aspect of this embodiment, $R^1$ is optionally substituted (C$_2$-C$_8$)alkenyl. In another aspect of this embodiment, $R^1$ is optionally substituted ethenyl. In another aspect of this embodiment, $R^1$ is optionally substituted (C$_2$-C$_8$)alkynyl. In another aspect of this embodiment, $R^1$ is optionally substituted ethynyl. In another aspect of this embodiment, $R^2$ is F. In another aspect of this embodiment, $R^2$ is Cl. In another aspect of this embodiment, $R^2$ is OH. In another aspect of this embodiment $R^{22}$ is OH. In another aspect of this embodiment, each $R^2$ and $R^{22}$ is OH. In another aspect of this embodiment, each $R^2$ is F and $R^{22}$ is OH. In another aspect of this embodiment, each $R^2$ is Cl and $R^{22}$ is OH. In another aspect of this embodiment, $R^7$ is H. In another aspect of this embodiment, $R^7$ is optionally substituted (C$_1$-C$_8$)alkyl. In another aspect of this embodiment, $R^7$ is optionally substituted (C$_2$-C$_8$)alkynyl. In another aspect of this embodiment, $R^7$ is CN. In another aspect of this embodiment, one of $R^c$ or $R^d$ is H. In another aspect of this embodiment, one of $R^c$ or $R^d$ is H and the other of $R^c$ or $R^d$ is optionally substituted (C$_1$-C$_8$)alkyl. In another aspect of this embodiment, $R^6$ is optionally substituted (C$_1$-C$_8$)alkyl. In another aspect of this embodiment, $R^6$ is optionally substituted (C$_3$-C$_8$)cycloalkyl. In another aspect of this embodiment, $R^4$ is optionally substituted (C$_6$-C$_{20}$)aryl. In another aspect of this embodiment, Ar is optionally substituted phenyl.

In another embodiment of the method for preparing a compound of Formula XIa or Formula XIb from a compound of Formula XII, $X^1$ is CH, $R^1$ is H, Cl or CH$_3$ and one of $R^c$ or $R^d$ is H. In another aspect of this embodiment, $R_2$ is F. In another aspect of this embodiment, $R^2$ is OH. In another aspect of this embodiment, $R^2$ is Cl. In another aspect of this embodiment $R^{22}$ is OH. In another aspect of this embodiment, each $R^2$ and $R^{22}$ is OH. In another aspect of this embodiment, each $R^2$ is F and $R^{22}$ is OH. In another aspect of this embodiment, each $R^2$ is Cl and $R^{22}$ is OH. In another aspect of this embodiment, $R^7$ is H. In another aspect of this embodiment, $R^7$ is optionally substituted (C$_1$-C$_8$) alkyl. In another aspect of this embodiment, $R^7$ is CH$_3$. In another aspect of this embodiment, $R^7$ is optionally substituted (C$_2$-C$_8$)alkynyl. In another aspect of this embodiment, $R^7$ is ethynyl. In another aspect of this embodiment, $R^7$ is CN. In another aspect of this embodiment, one of $R^c$ or $R^d$ is H and the other of $R^c$ or $R^d$ is optionally substituted (C$_1$-C$_8$)alkyl. In another aspect of this embodiment, $R^6$ is optionally substituted (C$_1$-C$_8$)alkyl. In another aspect of this embodiment, $R^6$ is optionally substituted (C$_3$-C$_8$)cycloalkyl. In another aspect of this embodiment, $R^4$ is optionally substituted (C$_6$-C$_{20}$)aryl. In another aspect of this embodiment, Ar is optionally substituted phenyl. In another aspect of this embodiment, $R^8$ is NR$^{11}$R$^{12}$. In another aspect of this embodiment, $R^8$ is OR$^{11}$. In another aspect of this embodiment, $R^8$ is NH$_2$. In another aspect of this embodiment, $R^9$ is OH. In another aspect of this embodiment, $R^9$ is H. In another aspect of this embodiment, $R^9$ is NR$^{11}$R$^{12}$. In another aspect of this embodiment, $R^9$ is $OR^{11}$. In another aspect of this embodiment, $R^8$ is $NR^{11}R^{12}$ and $R^9$ is H. In another aspect of this embodiment, $R^8$ is $NR^{11}R^{12}$ and $R_9$ is $NR^{11}R^{12}$.

In another embodiment of the method for preparing a compound of Formula XIa or Formula XIb from a compound of Formula XII, $X^1$ is CH, $R^1$ is H, Cl or $CH_3$, one of $R^c$ or $R^d$ is H and $R^7$ is H. In another aspect of this embodiment, $R^2$ is F. In another aspect of this embodiment, $R^2$ is Cl. In another aspect of this embodiment, $R^2$ is OH. In another aspect of this embodiment $R^{22}$ is OH. In another aspect of this embodiment, each $R^2$ and $R^{22}$ is OH. In another aspect of this embodiment, each $R^2$ is F and $R^{22}$ is OH. In another aspect of this embodiment, each $R^2$ is Cl and $R^{22}$ is OH. In another aspect of this embodiment, one of $R^c$ or $R^d$ is H and the other of $R^c$ or $R^d$ is optionally substituted ($C_1$-$C_8$)alkyl. In another aspect of this embodiment, one of $R^c$ or $R^d$ is H and the other of $R^c$ or $R^d$ is $CH_3$. In another aspect of this embodiment, $R^6$ is optionally substituted ($C_1$-$C_8$)alkyl. In another aspect of this embodiment, $R^6$ is optionally substituted ($C_3$-$C_8$) cycloalkyl. In another aspect of this embodiment, $R^4$ is optionally substituted ($C_6$-$C_{20}$) aryl. In another aspect of this embodiment, $R^4$ is optionally substituted phenyl. In another aspect of this embodiment, Ar is optionally substituted phenyl. In another aspect of this embodiment, $R^8$ is $NR^{11}R^{12}$. In another aspect of this embodiment, $R^8$ is $OR^{11}$. In another aspect of this embodiment, $R^8$ is $NH_2$. In another aspect of this embodiment, $R^8$ is OH. In another aspect of this embodiment, $R^9$ is H. In another aspect of this embodiment, $R^9$ is $NR^{11}R^{12}$. In another aspect of this embodiment, $R^9$ is $OR^{11}$. In another aspect of this embodiment, $R^8$ is $NR^{11}R^{12}$ and $R^9$ is H. In another aspect of this embodiment, $R^8$ is $NH_2$ and $R^9$ is H. In another aspect of this embodiment, $R^8$ is $NR^{11}R^{12}$ and $R^9$ is $NR^{11}R^{12}$. In another aspect of this embodiment, $R^8$ is $NH_2$ and $R^9$ is $NH_2$. In another aspect of this embodiment, $R^8$ is $OR^{11}$ and $R^9$ is $NH_2$. In another aspect of this embodiment, $R^8$ is OH and $R^9$ is $NH_2$.

In one embodiment of the method for preparing a compound of Formula XIa or Formula XIb from a compound of Formula XII, $X^1$ is N. In another aspect of this embodiment, $R^1$ is H. In another aspect of this embodiment, $R^1$ is F. In another aspect of this embodiment, $R^1$ is Cl. In another aspect of this embodiment, $R^1$ is optionally substituted ($C_1$-$C_8$)alkyl. In another aspect of this embodiment, $R_1$ is methyl. In another aspect of this embodiment, $R^1$ is optionally substituted ($C_2$-$C_8$)alkenyl. In another aspect of this embodiment, $R^1$ is optionally substituted ethenyl. In another aspect of this embodiment, $R^1$ is optionally substituted ($C_2$-$C_8$)alkynyl. In another aspect of this embodiment, $R^1$ is optionally substituted ethynyl. In another aspect of this embodiment, $R^2$ is F. In another aspect of this embodiment, $R^2$ is Cl. In another aspect of this embodiment, $R^2$ is OH. In another aspect of this embodiment $R^{22}$ is OH. In another aspect of this embodiment, each $R^2$ and $R^{22}$ is OH. In another aspect of this embodiment, each $R^2$ is F and $R^{22}$ is OH. In another aspect of this embodiment, each $R^2$ is Cl and $R^{22}$ is OH. In another aspect of this embodiment, each $R^1$ is Cl and each $R^2$ is F. In another aspect of this embodiment, each $R^1$ is $CH_3$ and each $R^2$ is Cl. In another aspect of this embodiment, each $R^1$ and $R^2$ is Cl. In another aspect of this embodiment, $R^7$ is H. In another aspect of this embodiment, $R^7$ is optionally substituted ($C_1$-$C_8$)alkyl. In another aspect of this embodiment, $R^7$ is optionally substituted ($C_2$-$C_8$)alkynyl. In another aspect of this embodiment, $R^7$ is CN. In another aspect of this embodiment, one of $R_c$ or $R_d$ is H. In another aspect of this embodiment, one of $R^c$ or $R^d$ is H and the other of $R^c$ or $R^d$ is optionally substituted ($C_1$-$C_8$)alkyl. In another aspect of this embodiment, $R^6$ is optionally substituted ($C_1$-$C_8$)alkyl. In another aspect of this embodiment, $R^6$ is optionally substituted ($C_3$-$C_8$)cycloalkyl. In another aspect of this embodiment, $R^4$ is optionally substituted ($C_6$-$C_{20}$)aryl. In another aspect of this embodiment, Ar is optionally substituted phenyl.

In another embodiment of the method for preparing a compound of Formula XIa or Formula XIb from a compound of Formula XII, $X^1$ is N, $R^1$ is H, Cl or $CH_3$ and one of $R^c$ or $R^d$ is H. In another aspect of this embodiment, $R^2$ is F. In another aspect of this embodiment, $R^2$ is Cl. In another aspect of this embodiment, $R^2$ is OH. In another aspect of this embodiment $R^{22}$ is OH. In another aspect of this embodiment, each $R^2$ and $R^{22}$ is OH. In another aspect of this embodiment, each $R^2$ is F and $R^{22}$ is OH. In another aspect of this embodiment, each $R^2$ is Cl and $R^{22}$ is OH. In another aspect of this embodiment, each $R^1$ is Cl and each $R^2$ is F. In another aspect of this embodiment, each $R^1$ is $CH_3$ and each $R^2$ is Cl. In another aspect of this embodiment, each $R^1$ and $R^2$ is Cl. In another aspect of this embodiment, $R^7$ is H. In another aspect of this embodiment, $R^7$ is optionally substituted ($C_1$-$C_8$)alkyl. In another aspect of this embodiment, $R^7$ is $CH_3$. In another aspect of this embodiment, $R^7$ is optionally substituted ($C_2$-$C_8$)alkynyl. In another aspect of this embodiment, $R^7$ is ethynyl. In another aspect of this embodiment, $R^7$ is CN. In another aspect of this embodiment, one of $R^c$ or $R^d$ is H and the other of $R^c$ or $R^d$ is optionally substituted ($C_1$-$C_8$)alkyl. In another aspect of this embodiment, $R^6$ is optionally substituted ($C_1$-$C_8$)alkyl. In another aspect of this embodiment, $R^4$ is optionally substituted ($C_6$-$C_{20}$)aryl. In another aspect of this embodiment, Ar is optionally substituted phenyl. In another aspect of this embodiment, $R^8$ is $NR^{11}R^{12}$. In another aspect of this embodiment, $R^9$ is $OR^{11}$. In another aspect of this embodiment, $R^8$ is $NH_2$. In another aspect of this embodiment, $R^8$ is OH. In another aspect of this embodiment, $R^9$ is H. In another aspect of this embodiment, $R^9$ is $NR^{11}R^{12}$. In another aspect of this embodiment, $R^9$ is $OR^{11}$. In another aspect of this embodiment, $R^8$ is $NR^{11}NR^{12}$ and $R^9$ is H. In another aspect of this embodiment, $R^8$ is $NR^{11}R^{12}$ and $R^9$ is $NR^{11}R^{12}$.

In another embodiment of the method for preparing a compound of Formula XIa or Formula XIb from a compound of Formula XII, $X^1$ is N, $R^1$ is H, Cl or $CH_3$, one of $R^c$ or $R^d$ is H and $R^7$ is H. In another aspect of this embodiment, $R^2$ is F. In another aspect of this embodiment, $R^2$ is Cl. In another aspect of this embodiment, $R^2$ is OH. In another aspect of this embodiment, $R^{22}$ is OH. In another aspect of this embodiment, each $R^2$ and $R^{22}$ is OH. In another aspect of this embodiment, each $R^2$ is F and $R^{22}$ is OH. In another aspect of this embodiment, each $R^2$ is Cl and $R^{22}$ is OH. In another aspect of this embodiment, each $R^1$ is Cl and each $R^2$ is F. In another aspect of this embodiment, each $R^1$ is $CH_3$ and each $R^2$ is Cl. In another aspect of this embodiment, each $R^1$ and $R^2$ is Cl. In another aspect of this embodiment, one of $R^c$ or $R^d$ is H and the other of $R^c$ or $R^d$ is optionally substituted ($C_1$-$C_8$)alkyl. In another aspect of this embodiment, one of $R^c$ or $R^d$ is H and the other of $R^c$ or $R^d$ is $CH_3$. In another aspect of this embodiment, $R^6$ is optionally substituted ($C_1$-$C_8$)alkyl. In another aspect of this embodiment, $R^6$ is optionally substituted ($C_3$-$C_8$)cycloalkyl. In another aspect of this embodiment, $R^4$ is optionally substituted ($C_6$-$C_{20}$)aryl. In another aspect of this embodiment, $R^4$ is optionally substituted phenyl. In another aspect of this embodiment, Ar is optionally substituted phenyl. In another aspect of this embodiment, $R^8$ is $NR^{11}R^{12}$. In another aspect of this embodiment, $R^8$ is $OR^{11}$. In another aspect of this embodiment, $R^8$ is $NH_2$. In another aspect of this embodiment, $R^8$ is OH. In another aspect of this embodiment, $R^9$ is H. In another aspect of this embodiment, $R^9$ is $NR^{11}R^{12}$. In another aspect of this embodiment, $R^9$ is $OR^{11}$. In another aspect of this embodiment, $R^8$ is $NR^{11}R^{12}$ and $R^9$ is H. In another aspect of this embodiment, $R^8$ is $NH_2$ and $R^9$ is H. In another aspect of this embodiment, $R_8$ is $NR^{11}R^{12}$ and $R^9$ is $NR^{11}R^{12}$. In another aspect of this embodiment, $R^8$ is $NH_2$ and $R^9$ is $NH_2$. In another aspect of this embodiment, $R^8$ is $OR^{11}$ and $R^9$ is $NH_2$. In another aspect of this embodiment, $R^8$ is OH and $R^9$ is $NH_2$.

In another embodiment of the method for preparing a compound of Formula Ia or Ib or a pharmaceutically acceptable salt or ester thereof, Formula Ia is Formula XIIIa, Formula Ib is Formula XIIIb and Formula II is Formula XIV:

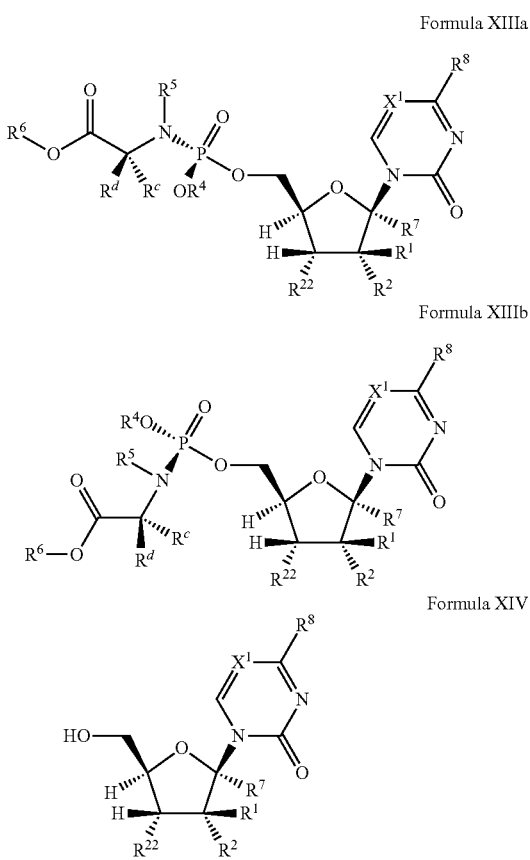

Formula XIIIa

Formula XIIIb

Formula XIV wherein: each $R^1$ is independently H, halogen, optionally substituted $(C_1-C_8)$alkyl, optionally substituted $(C_2-C_8)$alkenyl or optionally substituted $(C_2-C_8)$alkynyl;
each $R^2$ is independently halogen or $OR^{11}$;
each $R^5$ is H;
each $R^{22}$ is $OR^{11}$ and
the remaining variables are defined as for Formulae Ia or Ib or II or IIIa or IIIb.

In one embodiment of the method for preparing a compound of Formula XIIIa or Formula XIIIb from a compound of Formula XIV, $X^1$ is $CR^{10}$. In another aspect of this embodiment, $R^{10}$ is H. In another aspect of this embodiment, $R^{10}$ is $CH_3$. In another aspect of this embodiment, $R^1$ is H. In another aspect of this embodiment, $R^1$ is F. In another aspect of this embodiment, $R^1$ is Cl. In another aspect of this embodiment, $R^1$ is optionally substituted $(C_1-C_8)$alkyl. In another aspect of this embodiment, $R^1$ is methyl. In another aspect of this embodiment, $R^1$ is optionally substituted $(C_2-C_8)$alkenyl. In another aspect of this embodiment, $R^1$ is optionally substituted ethenyl. In another aspect of this embodiment, $R^1$ is optionally substituted $(C_2-C_8)$alkynyl. In another aspect of this embodiment, $R^1$ is optionally substituted ethynyl. In another aspect of this embodiment, $R^2$ is F. In another aspect of this embodiment, $R^2$ is Cl. In another aspect of this embodiment, $R^2$ is OH. In another aspect of this embodiment $R^{22}$ is OH. In another aspect of this embodiment, each $R^2$ and $R^{22}$ is OH. In another aspect of this embodiment, each $R^2$ is F and $R^{22}$ is OH. In another aspect of this embodiment, each $R^2$ is Cl and $R^{22}$ is OH. In another aspect of this embodiment, each $R^1$ is Cl and each $R^2$ is F. In another aspect of this embodiment, each $R^1$ is $CH_3$ and each $R^2$ is Cl. In another aspect of this embodiment, each $R^1$ and $R^2$ is Cl. In another aspect of this embodiment, $R^7$ is H. In another aspect of this embodiment, $R^7$ is optionally substituted $(C_1-C_8)$alkyl. In another aspect of this embodiment, $R^7$ is optionally substituted $(C_2-C_8)$alkynyl. In another aspect of this embodiment, $R^7$ is ON. In another aspect of this embodiment, one of $R^c$ or Rd is H. In another aspect of this embodiment, one of $R^c$ or $R^d$ is H and the other of $R^c$ or $R^d$ is optionally substituted $(C_1-C_8)$alkyl. In another aspect of this embodiment, $R^6$ is optionally substituted $(C_1-C_8)$alkyl. In another aspect of this embodiment, $R^6$ is optionally substituted $(C_3-C_8)$cycloalkyl. In another aspect of this embodiment, $R^4$ is optionally substituted $(C_6-C_{20})$aryl. In another aspect of this embodiment, Ar is optionally substituted phenyl.

In another embodiment of the method for preparing a compound of Formula XIIIa or Formula XIIIb from a compound of Formula XIV, $X^1$ is CH, $R^1$ is H, Cl or $CH_3$ and one of $R^c$ or $R^d$ is H. In another aspect of this embodiment, $R^2$ is F. In another aspect of this embodiment, $R^2$ is Cl. In another aspect of this embodiment, $R_2$ is OH. In another aspect of this embodiment $R^{22}$ is OH. In another aspect of this embodiment, each $R_2$ and $R_{22}$ is OH. In another aspect of this embodiment, each $R_2$ is F and $R_{22}$ is OH. In another aspect of this embodiment, each $R_2$ is Cl and $R_{22}$ is OH. In another aspect of this embodiment, each $R^1$ is Cl and each $R^2$ is F. In another aspect of this embodiment, each $R^1$ is $CH_3$ and each $R^2$ is Cl. In another aspect of this embodiment, each $R^1$ and $R^2$ is Cl. In another aspect of this embodiment, $R^7$ is H. In another aspect of this embodiment, $R^7$ is optionally substituted $(C_1-C_8)$alkyl. In another aspect of this embodiment, $R_7$ is $CH_3$. In another aspect of this embodiment, $R^7$ is optionally substituted $(C_2-C_8)$alkynyl. In another aspect of this embodiment, $R^7$ is ethynyl. In another aspect of this embodiment, $R^7$ is ON. In another aspect of this embodiment, one of $R^c$ or $R^d$ is H and the other of $R^c$ or $R^d$ is optionally substituted $(C_1-C_8)$alkyl. In another aspect of this embodiment, $R^6$ is optionally substituted $(C_1-C_8)$alkyl. In another aspect of this embodiment, $R^4$ is optionally substituted $(C_6-C_{20})$aryl. In another aspect of this embodiment, Ar is optionally substituted phenyl. In another aspect of this embodiment, $R^8$ is $NR^{11}R^{12}$. In another aspect of this embodiment, $R^8$ is $OR^{11}$. In another aspect of this embodiment, $R^8$ is $NH_2$. In another aspect of this embodiment, $R^8$ is OH.

In another embodiment of the method for preparing a compound of Formula XIIIa or Formula XIIIb from a compound of Formula XIV, $X^1$ is CH, $R^1$ is H, Cl or $CH_3$, one of $R^c$ or $R^d$ is H and $R^7$ is H. In another aspect of this embodiment, $R^2$ is F. In another aspect of this embodiment, $R^2$ is Cl. In another aspect of this embodiment, $R^2$ is OH. In another aspect of this embodiment $R^{22}$ is OH. In another aspect of this embodiment, each $R^2$ and $R^{22}$ is OH. In another aspect of this embodiment, each $R^2$ is F and $R^{22}$ is OH. In another aspect of this embodiment, each $R^2$ is Cl and $R^{22}$ is OH. In another aspect of this embodiment, one of $R^c$ or $R^d$ is H and the other of $R^c$ or $R^d$ is optionally substituted $(C_1-C_8)$alkyl. In another aspect of this embodiment, one of $R^c$ or $R^d$ is H and the other of $R^c$ or $R^d$ is $CH_3$. In another aspect of this embodiment, $R^6$ is optionally substituted $(C_1-C_8)$alkyl. In another aspect of this embodiment, $R^4$ is optionally substituted $(C_6-C_{20})$aryl. In another aspect of this embodiment, $R^4$ is optionally substituted phenyl. In another aspect of this embodiment, Ar is optionally substituted phenyl. In another aspect of this embodiment, $R^8$ is $NR^{11}R^{12}$. In another aspect of this embodiment, $R^8$ is $OR^{11}$. In another aspect of this embodiment, $R^8$ is $NH_2$. In another aspect of this embodiment, $R^8$ is OH.

In one embodiment of the method for preparing a compound of Formula XIIIa or Formula XIIIb from a compound of Formula XIV, $X^1$ is CF. In another aspect of this embodiment, $R^1$ is H. In another aspect of this embodiment, $R^1$ is F. In another aspect of this embodiment, $R^1$ is Cl. In another aspect of this embodiment, $R^1$ is optionally substituted $(C_1-C_8)$alkyl. In another aspect of this embodiment, $R^1$ is methyl. In another aspect of this embodiment, $R_1$ is optionally substituted $(C_2-C_8)$alkenyl. In another aspect of this embodiment, $R^1$ is optionally substituted ethenyl. In another aspect of this embodiment, $R^1$ is optionally substituted $(C_2-C_8)$alkynyl. In another aspect of this embodiment, $R^1$ is optionally substituted ethynyl. In another aspect of this embodiment, $R^2$ is F. In another aspect of this embodiment, $R^2$ is Cl. In another aspect of this embodiment, $R^2$ is OH. In another aspect of this embodiment $R^{22}$ is OH. In another aspect of this embodiment, each $R_2$ and $R_{22}$ is OH. In another aspect of this embodiment, each $R^2$ is F and $R^{22}$ is OH. In another aspect of this embodiment, each $R^2$ is Cl and $R^{22}$ is OH. In another aspect of this embodiment, $R^7$ is H. In another aspect of this embodiment, $R^7$ is optionally substituted $(C_1-C_8)$alkyl. In another aspect of this embodiment, $R^7$ is optionally substituted $(C_2-C_8)$alkynyl. In another aspect of this embodiment, $R^7$ is ON. In another aspect of this embodiment, one of $R^c$ or $R^d$ is H. In another aspect of this embodiment, one of $R^c$ or $R^d$ is H and the other of $R^c$ or $R^d$ is optionally substituted $(C_1-C_8)$alkyl. In another aspect of this embodiment, $R^6$ is optionally substituted $(C_1-C_8)$alkyl. In another aspect of this embodiment, $R^6$ is optionally substituted $(C_3-C_8)$cycloalkyl. In another aspect of this embodiment, $R^4$ is optionally substituted $(C_6-C_{20})$aryl. In another aspect of this embodiment, Ar is optionally substituted phenyl.

In another embodiment of the method for preparing a compound of Formula XIa or Formula XIb from a compound of Formula XII, $X^1$ is CF, $R^1$ is H, Cl or $CH_3$ and one of $R^c$ or $R^d$ is H. In another aspect of this embodiment, $R_2$ is F. In another aspect of this embodiment, $R_2$ is Cl. In another aspect of this embodiment, $R_2$ is OH. In another aspect of this embodiment $R^{22}$ is OH. In another aspect of this embodiment, each $R^2$ and $R^{22}$ is OH. In another aspect of this embodiment, each $R_2$ is F and $R^{22}$ is OH. In another aspect of this embodiment, each $R_2$ is Cl and $R^{22}$ is OH. In another aspect of this embodiment, $R^7$ is H. In another aspect of this embodiment, $R^7$ is optionally substituted $(C_1-C_8)$ alkyl. In another aspect of this embodiment, $R^7$ is $CH_3$. In another aspect of this embodiment, $R^7$ is optionally substituted $(C_2-C_8)$alkynyl. In another aspect of this embodiment, $R^7$ is ethynyl. In another aspect of this embodiment, $R^7$ is CN. In another aspect of this embodiment, one of $R^c$ or $R^d$ is H and the other of $R^c$ or $R^d$ is optionally substituted $(C_1-C_8)$alkyl. In another aspect of this embodiment, $R^6$ is optionally substituted $(C_1-C_8)$alkyl. In another aspect of this embodiment, $R^4$ is optionally substituted $(C_6-C_{20})$aryl. In another aspect of this embodiment, Ar is optionally substituted phenyl. In another aspect of this embodiment, $R^8$ is $NR^{11}R^{12}$. In another aspect of this embodiment, $R^8$ is $OR^{11}$. In another aspect of this embodiment, $R^8$ is $NH_2$. In another aspect of this embodiment, $R^8$ is OH.

In another embodiment of the method for preparing a compound of Formula XIIIa or Formula XIIIb from a compound of Formula XIV, $X^1$ is CF, $R^1$ is H, Cl or $CH_3$, one of $R^c$ or $R^d$ is H and $R^7$ is H. In another aspect of this embodiment, $R^2$ is F. In another aspect of this embodiment, $R^2$ is Cl. In another aspect of this embodiment, $R^2$ is OH. In another aspect of this embodiment $R^{22}$ is OH. In another aspect of this embodiment, each $R^2$ and $R^{22}$ is OH. In another aspect of this embodiment, each $R^2$ is F and $R^{22}$ is OH. In another aspect of this embodiment, each $R^2$ is Cl and $R^{22}$ is OH. In another aspect of this embodiment, one of $R^c$ or $R^d$ is H and the other of $R^c$ or $R^d$ is optionally substituted $(C_1-C_8)$alkyl. In another aspect of this embodiment, one of $R^c$ or $R^d$ is H and the other of $R^c$ or $R^d$ is $CH_3$. In another aspect of this embodiment, $R^6$ is optionally substituted $(C_1-C_8)$alkyl. In another aspect of this embodiment, $R^6$ is optionally substituted $(C_3-C_8)$cycloalkyl. In another aspect of this embodiment, $R^4$ is optionally substituted $(C_6-C_{20})$aryl. In another aspect of this embodiment, $R^4$ is optionally substituted phenyl. In another aspect of this embodiment, Ar is optionally substituted phenyl. In another aspect of this embodiment, $R^8$ is $NR^{11}R^{12}$. In another aspect of this embodiment, $R^8$ is $OR^{11}$. In another aspect of this embodiment, $R^8$ is $NH_2$. In another aspect of this embodiment, $R^8$ is OH.

Definitions

Unless stated otherwise, the following terms and phrases as used herein are intended to have the following meanings: When trade names are used herein, applicants intend to independently include the tradename product and the active pharmaceutical ingredient(s) of the tradename product.

As used herein, "a compound of the invention" or "a compound of Formula I" means a compound of Formula I or a pharmaceutically acceptable salt, thereof. Similarly, with respect to isolatable intermediates, the phrase "a compound of Formula (number)" means a compound of that formula and pharmaceutically acceptable salts, thereof.

"Alkyl" is hydrocarbon containing normal, secondary, tertiary or cyclic carbon atoms. For example, an alkyl group can have 1 to 20 carbon atoms (i.e, $C_1-C_{20}$alkyl), 1 to 8 carbon atoms (i.e. $C_1-C_8$alkyl), or 1 to 6 carbon atoms (i.e. $C_1-C_6$alkyl). Examples of suitable alkyl groups include, but are not limited to, methyl (Me, $-CH_3$), ethyl (Et, $-CH_2CH_3$), 1-propyl (n-Pr, n-propyl, $-CH_2CH_2CH_3$), 2-propyl (i-Pr, i-propyl, $-CH(CH_3)_2$), 1-butyl (n-Bu, n-butyl, $-CH_2CH_2CH_2CH_3$), 2-methyl-1-propyl (i-Bu, i-butyl, $-CH_2CH(CH_3)_2$), 2-butyl (s-Bu, s-butyl, $-CH(CH_3)CH_2CH_3$), 2-methyl-2-propyl (t-Bu, t-butyl, $-C(CH_3)_3$), 1-pentyl (n-pentyl, $-CH_2CH_2CH_2CH_2CH_3$), 2-pentyl ($-CH(CH_3)CH_2CH_2CH_3$), 3-pentyl ($-CH(CH_2CH_3)_2$), 2-methyl-2-butyl ($-C(CH_3)_2CH_2CH_3$), 3-methyl-2-butyl ($-CH(CH_3)CH(CH_3)_2$), 3-methyl-1-butyl ($-CH_2CH_2CH(CH_3)_2$), 2-methyl-1-butyl ($-CH_2CH(CH_3)CH_2CH_3$), 1-hexyl ($-CH_2CH_2CH_2CH_2CH_2CH_3$), 2-hexyl ($-CH(CH_3)CH_2CH_2CH_2CH_3$), 3-hexyl ($-CH(CH_2CH_3)$ ($CH_2CH_2CH_3$)), 2-methyl-2-pentyl (—$C(CH_3)_2$ $CH_2CH_2CH_3$), 3-methyl-2-pentyl (—$CH(CH_3)CH(CH_3)$ $CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, and octyl (—$(CH_2)_7CH_3$).

"Alkoxy" means a group having the formula —O-alkyl, in which an alkyl group, as defined above, is attached to the parent molecule via an oxygen atom. The alkyl portion of an alkoxy group can have 1 to 20 carbon atoms (i.e. $C_1$-$C_{20}$alkoxy), 1 to 12 carbon atoms (i.e. $C_1$-$C_{12}$ alkoxy), or 1 to 6 carbon atoms (i.e. $C_1$-$C_6$alkoxy). Examples of suitable alkoxy groups include, but are not limited to, methoxy (—O—$CH_3$ or —OMe), ethoxy (—$OCH_2CH_3$ or —OEt), t-butoxy (—O—$C(CH_3)_3$ or —OtBu) and the like.

"Haloalkyl" is an alkyl group, as defined above, in which one or more hydrogen atoms of the alkyl group is replaced with a halogen atom. The alkyl portion of a haloalkyl group can have 1 to 20 carbon atoms (i.e. $C_1$-$C_{20}$ haloalkyl), 1 to 12 carbon atoms (i.e. $C_1$-$C_{12}$haloalkyl), or 1 to 6 carbon atoms (i.e. $C_1$-$C_6$alkyl). Examples of suitable haloalkyl groups include, but are not limited to, —$CF_3$, —$CHF_2$, —$CFH_2$, —$CH_2CF_3$, and the like.

"Alkenyl" is a hydrocarbon containing normal, secondary, tertiary or cyclic carbon atoms with at least one site of unsaturation, i.e. a carbon-carbon, sp2 double bond. For example, an alkenyl group can have 2 to 20 carbon atoms (i.e. $C_2$-$C_{20}$ alkenyl), 2 to 8 carbon atoms (i.e. $C_2$-$C_8$ alkenyl), or 2 to 6 carbon atoms (i.e. $C_2$-$C_6$alkenyl). Examples of suitable alkenyl groups include, but are not limited to, ethylene or vinyl (—$CH=CH_2$), allyl (—$CH_2CH=CH_2$), cyclopentenyl (—$C_5H_7$), and 5-hexenyl (—$CH_2CH_2CH_2CH_2CH=CH_2$).

"Alkynyl" is a hydrocarbon containing normal, secondary, tertiary or cyclic carbon atoms with at least one site of unsaturation, i.e. a carbon-carbon, sp triple bond. For example, an alkynyl group can have 2 to 20 carbon atoms (i.e. $C_2$-$C_{20}$ alkynyl), 2 to 8 carbon atoms (i.e. $C_2$-$C_8$ alkynyl), or 2 to 6 carbon atoms (i.e. $C_2$-$C_6$ alkynyl). Examples of suitable alkynyl groups include, but are not limited to, acetylenic (—C≡CH), propargyl (—$CH_2$C≡CH), and the like.

"Alkylene" refers to a saturated, branched or straight chain or cyclic hydrocarbon radical having two monovalent radical centers derived by the removal of two hydrogen atoms from the same or two different carbon atoms of a parent alkane. For example, an alkylene group can have 1 to 20 carbon atoms, 1 to 10 carbon atoms, or 1 to 6 carbon atoms. Typical alkylene radicals include, but are not limited to, methylene (—$CH_2$—), 1,1-ethyl (—$CH(CH_3)$—), 1,2-ethyl (—$CH_2CH_2$—), 1,1-propyl (—$CH(CH_2CH_3)$—), 1,2-propyl (—$CH_2CH(CH_3)$—), 1,3-propyl (—$CH_2CH_2CH_2$—), 1,4-butyl (—$CH_2CH_2CH_2CH_2$—), and the like.

"Alkenylene" refers to an unsaturated, branched or straight chain or cyclic hydrocarbon radical having two monovalent radical centers derived by the removal of two hydrogen atoms from the same or two different carbon atoms of a parent alkene. For example, an alkenylene group can have 1 to 20 carbon atoms, 1 to 10 carbon atoms, or 1 to 6 carbon atoms. Typical alkenylene radicals include, but are not limited to, 1,2-ethylene (—CH=CH—).

"Alkynylene" refers to an unsaturated, branched or straight chain or cyclic hydrocarbon radical having two monovalent radical centers derived by the removal of two hydrogen atoms from the same or two different carbon atoms of a parent alkyne. For example, an alkynylene group can have 1 to 20 carbon atoms, 1 to 10 carbon atoms, or 1 to 6 carbon atoms. Typical alkynylene radicals include, but are not limited to, acetylene (—C≡C—), propargyl (—$CH_2$C≡C—), and 4-pentynyl (—$CH_2CH_2CH_2$C≡C—).

"Amino" refers generally to a nitrogen radical which can be considered a derivative of ammonia, having the formula —$N(X)_2$, where each "X" is independently H, substituted or unsubstituted alkyl, substituted or unsubstituted carbocyclyl, substituted or unsubstituted heterocyclyl, etc. The hybridization of the nitrogen is approximately $sp^3$. Nonlimiting types of amino include —$NH_2$, —$N(alkyl)_2$, —NH(alkyl), —$N(carbocyclyl)_2$, —NH(carbocyclyl), —$N(heterocyclyl)_2$, —NH(heterocyclyl), —$N(aryl)_2$, —NH(aryl), —N(alkyl)(aryl), —N(alkyl)(heterocyclyl), —N(carbocyclyl)(heterocyclyl), —N(aryl)(heteroaryl), —N(alkyl)(heteroaryl), etc. The term "alkylamino" refers to an amino group substituted with at least one alkyl group. Nonlimiting examples of amino groups include —$NH_2$—NH($CH_3$), —$N(CH_3)_2$, —NH($CH_2CH_3$), —$N(CH_2CH_3)_2$, —NH(phenyl), —$N(phenyl)_2$, —NH(benzyl), —$N(benzyl)_2$, etc. Substituted alkylamino refers generally to alkylamino groups, as defined above, in which at least one substituted alkyl, as defined herein, is attached to the amino nitrogen atom. Non-limiting examples of substituted alkylamino includes —NH(alkylene-C(O)—OH), —NH(alkylene-C(O)—O-alkyl), —$N(alkylene-C(O)—OH)_2$, —N(alkylene-C(O)—O-alkyl)$_2$, etc.

"Aryl" means an aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 10 carbon atoms. Typical aryl groups include, but are not limited to, radicals derived from benzene (e.g., phenyl), substituted benzene, naphthalene, anthracene, biphenyl, and the like.

"Arylalkyl" refers to an acyclic alkyl radical in which one of the hydrogen atoms bonded to a carbon atom, typically a terminal or sp3 carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group can comprise 7 to 20 carbon atoms, e.g., the alkyl moiety is 1 to 6 carbon atoms and the aryl moiety is 6 to 14 carbon atoms.

"Arylalkenyl" refers to an acyclic alkenyl radical in which one of the hydrogen atoms bonded to a carbon atom, typically a terminal or $sp^3$ carbon atom, but also an sp2 carbon atom, is replaced with an aryl radical. The aryl portion of the arylalkenyl can include, for example, any of the aryl groups disclosed herein, and the alkenyl portion of the arylalkenyl can include, for example, any of the alkenyl groups disclosed herein. The arylalkenyl group can comprise 8 to 20 carbon atoms, e.g., the alkenyl moiety is 2 to 6 carbon atoms and the aryl moiety is 6 to 14 carbon atoms.

"Arylalkynyl" refers to an acyclic alkynyl radical in which one of the hydrogen atoms bonded to a carbon atom, typically a terminal or $sp^3$ carbon atom, but also an sp2 carbon atom, is replaced with an aryl radical. The aryl portion of the arylalkynyl can include, for example, any of the aryl groups disclosed herein, and the alkynyl portion of the arylalkynyl can include, for example, any of the alkynyl groups disclosed herein. The arylalkynyl group can comprise 8 to 20 carbon atoms, e.g., the alkynyl moiety is 2 to 6 carbon atoms and the aryl moiety is 6 to 14 carbon atoms.

The term "substituted" in reference to alkyl, alkylene, aryl, arylalkyl, alkoxy, heterocyclyl, heteroaryl, carbocyclyl, etc., for example, "substituted alkyl", "substituted alkylene", "substituted aryl", "substituted arylalkyl", "substituted heterocyclyl", and "substituted carbocyclyl" means, unless otherwise stated, alkyl, alkylene, aryl, arylalkyl, heterocyclyl, carbocyclyl respectively, in which one or more hydrogen atoms are each independently replaced with a non-hydrogen substituent. Typical substituents include, but are not limited to, —X, —$R^b$, —$O^-$, =O, —$OR^b$, —$SR^b$, —$S^-$, —$NR^b{}_2$, —$N^+R^b{}_3$, =$NR^b$, —$CX_3$, —CN, —OCN, —SCN, —N=C=O, —NCS, —NO, —$NO_2$, =$N_2$, —$N_3$, —NHC(=O)$R^b$, —OC(=O)$R^b$, —NHC(=O)$NR^b{}_2$, —S(=O)$_2$—, —S(=O)$_2$OH, —S(=O)$_2R^b$, —OS(=O)$_2OR^b$, —S(=O)$_2NR^b{}_2$, —S(=O)$R^b$, —OP(=O)(O$R^b$)$_2$, —P(=O)(O$R^b$)$_2$, —P(=O)(O$R^-$)$_2$, —P(=O)(OH)$_2$, —P(O)(O$R^b$)($O^-$), —C(=O)$R^b$, —C(=O)X, —C(S)$R^b$, —C(O)$OR^b$, —C(O)$O^-$, —C(S)$OR^b$, —C(O)$SR^b$, —C(S)$SR^b$, —C(O)$NR^b{}_2$, —C(S)$NR^b{}_2$, —C(=$NR^b$)$NR^b{}_2$, where each X is independently a halogen: F, Cl, Br, or I; and each $R^b$ is independently H, alkyl, aryl, arylalkyl, a heterocycle, or a protecting group or prodrug moiety. Alkylene, alkenylene, and alkynylene groups may also be similarly substituted. Unless otherwise indicated, when the term "substituted" is used in conjunction with groups such as arylalkyl, which have two or more moieties capable of substitution, the substituents can be attached to the aryl moiety, the alkyl moiety, or both.

The term "prodrug" as used herein refers to any compound that when administered to a biological system generates the drug substance, i.e. active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound.

One skilled in the art will recognize that substituents and other moieties of the compounds of Formula I-XIV should be selected in order to provide a compound which is sufficiently stable to provide a pharmaceutically useful compound which can be formulated into an acceptably stable pharmaceutical composition. Compounds of Formula I-XIV which have such stability are contemplated as falling within the scope of the present invention.

"Heteroalkyl" refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, or S) the resulting heteroalkyl groups are, respectively, an alkoxy group (e.g., —$OCH_3$, etc.), an amine (e.g. —$NHCH_3$, —N($CH_3$)$_2$, etc.), or a thioalkyl group (e.g. —$SCH_3$). If a non-terminal carbon atom of the alkyl group which is not attached to the parent molecule is replaced with a heteroatom (e.g., O, N, or S) the resulting heteroalkyl groups are, respectively, an alkyl ether (e.g., —$CH_2CH_2$—O—$CH_3$, etc.), an alkyl amine (e.g., —$CH_2NHCH_3$, —$CH_2$N($CH_3$)$_2$, etc.), or a thioalkyl ether (e.g., —$CH_2$—S—$CH_3$). If a terminal carbon atom of the alkyl group is replaced with a heteroatom (e.g., O, N, or S), the resulting heteroalkyl groups are, respectively, a hydroxyalkyl group (e.g., —$CH_2CH_2$—OH), an aminoalkyl group (e.g., —$CH_2NH_2$), or an alkyl thiol group (e.g. —$CH_2CH_2$—SH). A heteroalkyl group can have, for example, 1 to 20 carbon atoms, 1 to 10 carbon atoms, or 1 to 6 carbon atoms. A $C_1$-$C_6$ heteroalkyl group means a heteroalkyl group having 1 to 6 carbon atoms.

"Heterocycle" or "heterocyclyl" as used herein includes by way of example and not limitation those heterocycles described in Paquette, Leo A.; Principles of Modern Heterocyclic Chemistry (W. A. Benjamin, New York, 1968), particularly Chapters 1, 3, 4, 6, 7, and 9; The Chemistry of Heterocyclic Compounds, A Series of Monographs" (John Wiley & Sons, New York, 1950 to present), in particular Volumes 13, 14, 16, 19, and 28; and J. Am. Chem. Soc. (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, or S). The terms "heterocycle" or "heterocyclyl" includes saturated rings, partially unsaturated rings, and aromatic rings (i.e. heteroaromatic rings). Substituted heterocyclyls include, for example, heterocyclic rings substituted with any of the substituents disclosed herein including carbonyl groups. A non-limiting example of a carbonyl substituted heterocyclyl is:

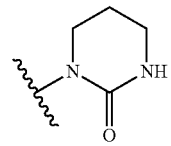 [SMILES: *N1CCCNC1=O]

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl:

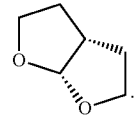

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Heterocyclylalkyl" refers to an acyclic alkyl radical in which one of the hydrogen atoms bonded to a carbon atom, typically a terminal or $sp^3$ carbon atom, is replaced with a heterocyclyl radical (i.e. a heterocyclyl-alkylene-moiety). Typical heterocyclylalkyl groups include, but are not limited to heterocyclyl-$CH_2$—, 2-(heterocyclyl)ethan-1-yl, and the like, wherein the "heterocyclyl" portion includes any of the heterocyclyl groups described above, including those described in Principles of Modem Heterocyclic Chemistry. One skilled in the art will also understand that the heterocyclyl group can be attached to the alkyl portion of the heterocyclyl alkyl by means of a carbon-carbon bond or a carbon-heteroatom bond, with the proviso that the resulting group is chemically stable. The heterocyclyl alkyl group comprises 3 to 20 carbon atoms, e.g., the alkyl portion of the arylalkyl group is 1 to 6 carbon atoms and the heterocyclyl moiety is 2 to 14 carbon atoms. Examples of heterocyclylalkyls include by way of example and not limitation 5-membered sulfur, oxygen, and/or nitrogen containing heterocycles such as thiazolylmethyl, 2-thiazolylethan-1-yl, imidazolylmethyl, oxazolylmethyl, thiadiazolylmethyl, etc., 6-membered sulfur, oxygen, and/or nitrogen containing heterocycles such as piperidinylm ethyl, piperazinylmethyl, morpholinylmethyl, pyridinylmethyl, pyridizylmethyl, pyrimidylmethyl, pyrazinylmethyl, etc.

"Heterocyclylalkenyl" refers to an acyclic alkenyl radical in which one of the hydrogen atoms bonded to a carbon atom, typically a terminal or $sp^3$ carbon atom, but also a sp2 carbon atom, is replaced with a heterocyclyl radical (i.e. a heterocyclyl-alkenylene-moiety). The heterocyclyl portion of the heterocyclylalkenyl group includes any of the heterocyclyl groups described herein, including those described in Principles of Modern Heterocyclic Chemistry, and the alkenyl portion of the heterocyclylalkenyl group includes any of the alkenyl groups disclosed herein. One skilled in the art will also understand that the heterocyclyl group can be attached to the alkenyl portion of the heterocyclylalkenyl by means of a carbon-carbon bond or a carbon-heteroatom bond, with the proviso that the resulting group is chemically stable. The heterocyclylalkenyl group comprises 4 to 20 carbon atoms, e.g., the alkenyl portion of the heterocyclyl-alkenyl group is 2 to 6 carbon atoms and the heterocyclyl moiety is 2 to 14 carbon atoms.

"Heterocyclylalkynyl" refers to an acyclic alkynyl radical in which one of the hydrogen atoms bonded to a carbon atom, typically a terminal or $sp^3$ carbon atom, but also an sp2 carbon atom, is replaced with a heterocyclyl radical (i.e. a heterocyclylalkynylene-moiety). The heterocyclyl portion of the heterocyclylalkynyl group includes any of the heterocyclyl groups described herein, including those described in Principles of Modern Heterocyclic Chemistry, and the alkynyl portion of the heterocyclylalkynyl group includes any of the alkynyl groups disclosed herein. One skilled in the art will also understand that the heterocyclyl group can be attached to the alkynyl portion of the heterocyclylalkynyl by means of a carbon-carbon bond or a carbon-heteroatom bond, with the proviso that the resulting group is chemically stable. The heterocyclylalkynyl group comprises 4 to 20 carbon atoms, e.g., the alkynyl portion of the heterocyclyl alkynyl group is 2 to 6 carbon atoms and the heterocyclyl moiety is 2 to 14 carbon atoms.

"Heteroaryl" refers to an aromatic heterocyclyl having at least one heteroatom in the ring. Non-limiting examples of suitable heteroatoms which can be included in the aromatic ring include oxygen, sulfur, and nitrogen. Non-limiting examples of heteroaryl rings include all of those aromatic rings listed in the definition of "heterocyclyl", including pyridinyl, pyrrolyl, oxazolyl, indolyl, isoindolyl, purinyl, furanyl, thienyl, benzofuranyl, benzothiophenyl, carbazolyl, imidazolyl, thiazolyl, isoxazolyl, pyrazolyl, isothiazolyl, quinolyl, isoquinolyl, pyridazyl, pyrimidyl, pyrazyl, etc.

The term "purine" or "pyrimidine" base comprises, but is not limited to, adenine, $N^6$-alkylpurines, $N^6$-acylpurines (wherein acyl is C(O)(alkyl, aryl, alkylaryl, or arylalkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-allylaminopurine, $N^6$-thioallyl purine, $N^2$-alkylpurines, $N$-alkyl-6-thiopurines, thymine, cytosine, 5-fluorocytosine, 5-methylcytosine, 6-azapyrimidine, including 6-azacytosine, 2- and/or 4-mercaptopyrmidine, uracil, 5-halouracil, including 5-fluorouracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-5-iodopyrimidine, $C^6$-iodo-pyrimidine, $C^5$—Br-vinyl pyrimidine, $C^6$—Br-vinyl pyrimidine, $C^5$-nitropyrimidine, $C_5$-amino-pyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, and pyrazolopyrimidinyl. Purine bases include, but are not limited to, guanine, adenine, hypoxanthine, 2,6-diaminopurine, and 6-chloropurine. Additional non-classical purine bases include pyrrolo [1,2-f][1,2,4] triazines, imidazo[1,5-f][1,2,4]triazines, imidazo[1,2-f][1,2,4]triazines, and [12,4]triazolo[4,3-f][1,2,4] triazines, all of which are optionally substituted. The purine and pyrimidine bases of Formula II are linked to the ribose sugar, or analog thereof, through a nitrogen atom or carbon atom of the base. Functional oxygen and nitrogen groups on the base can be protected as necessary or desired. Suitable protecting groups are well known to those skilled in the art, and include, but are not limited to, trimethylsilyl, dimethylhexylsilyl, t-butyldimethylsilyl, and t-butyldiphenylsilyl, trityl, alkyl groups, and acyl groups such as acetyl and propionyl, methanesulfonyl, and p-toluenesulfonyl.

"Carbocycle" or "carbocyclyl" refers to a saturated (i.e. cycloalkyl), partially unsaturated (e.g., cycloakenyl, cycloalkadienyl, etc.) or aromatic ring having 3 to 7 carbon atoms as a monocycle, 7 to 12 carbon atoms as a bicycle, and up to about 20 carbon atoms as a polycycle. Monocyclic carbocycles have 3 to 7 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system, or spiro-fused rings. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and phenyl. Non-limiting examples of bicyclocarbocycles includes naphthyl, tetrahydronapthalene, and decaline.

"Carbocyclylalkyl" refers to an acyclic alkyl radical in which one of the hydrogen atoms bonded to a carbon atom is replaced with a carbocyclyl radical as described herein. Typical, but non-limiting, examples of carbocyclylalkyl groups include cyclopropylmethyl, cyclopropylethyl, cyclobutylmethyl, cyclopentylmethyl and cyclohexylmethyl.

"Arylheteroalkyl" refers to a heteroalkyl as defined herein, in which a hydrogen atom (which may be attached either to a carbon atom or a heteroatom) has been replaced with an aryl group as defined herein. The aryl groups may be bonded to a carbon atom of the heteroalkyl group, or to a heteroatom of the heteroalkyl group, provided that the resulting arylheteroalkyl group provides a chemically stable moiety. For example, an arylheteroalkyl group can have the general formulae -alkylene-O-aryl, -alkylene-O-alkylene-aryl, -alkylene-NH-aryl, -alkylene-NH-alkylene-aryl, -alkylene-S-aryl, -alkylene-S-alkylene-aryl, etc. In addition, any of the alkylene moieties in the general formulae above can be further substituted with any of the substituents defined or exemplified herein.

"Heteroarylalkyl" refers to an alkyl group, as defined herein, in which a hydrogen atom has been replaced with a heteroaryl group as defined herein. Non-limiting examples of heteroaryl alkyl include —$CH_2$-pyridinyl, —$CH_2$-pyrrolyl, —$CH_2$-oxazolyl, —$CH_2$-indolyl, —$CH_2$-isoindolyl, —$CH_2$-purinyl, —$CH_2$-furanyl, —$CH_2$-thienyl, —$CH_2$-benzofuranyl, —$CH_2$-benzothiophenyl, —$CH_2$-earbazolyl, —$CH_2$-imidazolyl, —$CH_2$-thiazolyl, —$CH_2$-isoxazolyl, —$CH_2$-pyrazolyl, —$CH_2$-isothiazolyl, —$CH_2$-quinolyl, —$CH_2$-isoquinolyl, —$CH_2$-pyridazyl, —$CH_2$-pyrimidyl, —$CH_2$-pyrazyl, —$CH(CH_3)$-pyridinyl, —$CH(CH_3)$-pyrrolyl, —$CH(CH_3)$-oxazolyl, —$CH(CH_3)$-indolyl, —$CH(CH_3)$-isoindolyl, —$CH(CH_3)$-purinyl, —$CH(CH_3)$-furanyl, —$CH(CH_3)$-thienyl, —$CH(CH_3)$-benzofuranyl, —$CH(CH_3)$-benzothiophenyl, —$CH(CH_3)$-carbazolyl, —$CH(CH_3)$-imidazolyl, —$CH(CH_3)$-thiazolyl, —$CH(CH_3)$-isoxazolyl, —$CH(CH_3)$-pyrazolyl, —$CH(CH_3)$-isothiazolyl, —$CH(CH_3)$-quinolyl, —$CH(CH_3)$-isoquinolyl, —$CH(CH_3)$-pyridazyl, —$CH(CH_3)$-pyrimidyl, —$CH(CH_3)$-pyrazyl, etc.

The term "optionally substituted" in reference to a particular moiety of the compound of Formula I-XIV (e.g., an optionally substituted aryl group) refers to a moiety wherein all substituents are hydrogen or wherein one or more of the hydrogens of the moiety may be replaced by substituents such as those listed under the definition of "substituted".

The term "optionally replaced" in reference to a particular moiety of the compound of Formula I-XIV (e.g., the carbon atoms of said ($C_1$-$C_8$)alkyl may be optionally replaced by —O—, —S—, or —$NR^a$—) means that one or more of the methylene groups of the ($C_1$-$C_8$)alkyl may be replaced by 0, 1, 2, or more of the groups specified (e.g., —O—, —S—, or —$NR^a$—).

The term "non-terminal carbon atom(s)" in reference to an alkyl, alkenyl, alkynyl, alkylene, alkenylene, or alkynylene moiety refers to the carbon atoms in the moiety that intervene between the first carbon atom of the moiety and the last carbon atom in the moiety. Therefore, by way of example and not limitation, in the alkyl moiety —$CH_2$(C*)$H_2$(C*)$H_2CH_3$ or alkylene moiety —$CH_2$(C*)$H_2$(C*)$H_2CH_2$— the C* atoms would be considered to be the non-terminal carbon atoms.

"Linker" or "link" means a chemical moiety comprising a covalent bond or a chain of atoms.

Linkers include repeating units of alkyloxy (e.g. polyethyleneoxy, PEG, polymethyleneoxy) and alkylamino (e.g. polyethyleneamino, Jeffamine™); and diacid ester and amides including succinate, succinamide, diglycolate, malonate, and caproamide.

The terms such as "oxygen-linked", "nitrogen-linked", "carbon-linked", "sulfur-linked", or "phosphorous-linked" mean that if a bond between two moieties can be formed by using more than one type of atom in a moiety, then the bond formed between the moieties is through the atom specified. For example, a nitrogen-linked amino acid would be bonded through a nitrogen atom of the amino acid rather than through an oxygen or carbon atom of the amino acid.

Some embodiments of the compounds of Formula I-XIV comprise the moiety

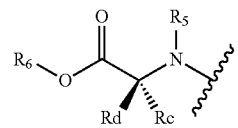

which may comprise a radical of a nitrogen-linked ester of a naturally occurring alpha amino acid. Examples of naturally occurring amino acids include isoleucine, leucine, lysine, methionine, phenylalanine, threonine, tryptophan, valine, alanine, asparagine, aspartic acid, cysteine, glutamic acid, glutamine, glycine, proline, selenocysteine, serine, tyrosine, arginine, histidine, ornithine and taurine. The esters of these amino acids comprise any of those described for the substitutent $R^6$, particularly those in which $R^6$ is optionally substituted ($C_1$-$C_8$)alkyl.

Unless otherwise specified, the carbon atoms of the compounds of Formula I-XIV are intended to have a valence of four. In some chemical structure representations where carbon atoms do not have a sufficient number of variables attached to produce a valence of four, the remaining carbon substituents needed to provide a valence of four should be assumed to be hydrogen. For example,

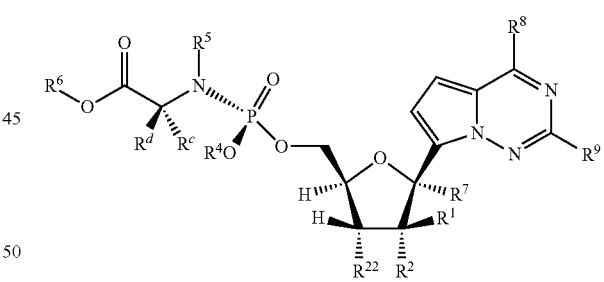

has the same meaning as

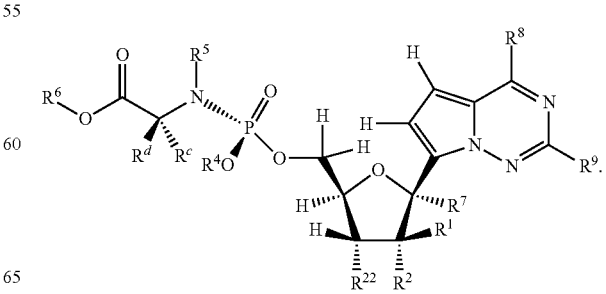

"Protecting group" refers to a moiety of a compound that masks or alters the properties of a functional group or the properties of the compound as a whole. The chemical substructure of a protecting group varies widely. One function of a protecting group is to serve as an intermediate in the synthesis of the parental drug substance. Chemical protecting groups and strategies for protection/deprotection are well known in the art. See: "Protective Groups in Organic Chemistry", Theodora W. Greene (John Wiley & Sons, Inc., New York, 1991. Protecting groups are often utilized to mask the reactivity of certain functional groups, to assist in the efficiency of desired chemical reactions, e.g. making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g. alcohols, be physiologically acceptable, although in general it is more desirable if the products are pharmacologically innocuous.

"Prodrug moiety" means a labile functional group which separates from the active inhibitory compound during metabolism, systemically, inside a cell, by hydrolysis, enzymatic cleavage, or by some other process (Bundgaard, Hans, "Design and Application of Prodrugs" in Textbook of Drug Design and Development (1991), P. Krogsgaard-Larsen and H. Bundgaard, Eds. Harwood Academic Publishers, pp. 113-191). Enzymes which are capable of an enzymatic activation mechanism with the prodrug compounds of the invention include, but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy.

A prodrug moiety may include an active metabolite or drug itself.

It is to be noted that all enantiomers, diastereomers, and racemic mixtures, tautomers, polymorphs, pseudopolymorphs of compounds within the scope of Formula I-IV and pharmaceutically acceptable salts thereof are embraced by the present invention. All mixtures of such enantiomers and diastereomers are within the scope of the present invention.

A compound of Formula I-XIV and its pharmaceutically acceptable salts may exist as different polymorphs or pseudopolymorphs. As used herein, crystalline polymorphism means the ability of a crystalline compound to exist in different crystal structures. The crystalline polymorphism may result from differences in crystal packing (packing polymorphism) or differences in packing between different conformers of the same molecule (conformational polymorphism). As used herein, crystalline pseudopolymorphism means the ability of a hydrate or solvate of a compound to exist in different crystal structures. The pseudopolymorphs of the instant invention may exist due to differences in crystal packing (packing pseudopolymorphism) or due to differences in packing between different conformers of the same molecule (conformational pseudopolymorphism). The instant invention comprises all polymorphs and pseudopolymorphs of the compounds of Formula I-IV and their pharmaceutically acceptable salts.

A compound of Formula I-XIV and its pharmaceutically acceptable salts may also exist as an amorphous solid. As used herein, an amorphous solid is a solid in which there is no long-range order of the positions of the atoms in the solid. This definition applies as well when the crystal size is two nanometers or less. Additives, including solvents, may be used to create the amorphous forms of the instant invention. The instant invention comprises all amorphous forms of the compounds of Formula I-IV and their pharmaceutically acceptable salts.

Selected substituents comprising the compounds of Formula I-XIV are present to a recursive degree. In this context, "recursive substituent" means that a substituent may recite another instance of itself. Because of the recursive nature of such substituents, theoretically, a large number of compounds may be present in any given embodiment. One of ordinary skill in the art of medicinal chemistry understands that the total number of such substituents is reasonably limited by the desired properties of the compound intended. Such properties include, by way of example and not limitation, physical properties such as molecular weight, solubility or log P, application properties such as activity against the intended target, and practical properties such as ease of synthesis. Recursive substituents are an intended aspect of the invention. One of ordinary skill in the art of medicinal chemistry understands the versatility of such substituents. To the degree that recursive substituents are present in an embodiment of the invention, they may recite another instance of themselves, 0, 1, 2, 3, or 4 times. The modifier "about" used in connection with a quantity is inclusive of the stated value and has the meaning dictated by the context (e.g., includes the degree of error associated with measurement of the particular quantity).

Any reference to the compounds of the invention described herein also includes a reference to a physiologically acceptable salt thereof. Examples of physiologically acceptable salts of the compounds of the invention include salts derived from an appropriate base, such as an alkali metal or an alkaline earth (for example, $Na^+$, $Li^+$, $K+$, $Ca^{+2}$ and $Mg^{+2}$, ammonium and $NR^a_4{}^+$ (wherein $R^a$ is defined herein). Physiologically acceptable salts of a nitrogen atom or an amino group include (a) acid addition salts formed with inorganic acids, for example, hydrochloric acid, hydrobromic acid, sulfuric acid, sulfamic acids, phosphoric acid, nitric acid and the like; (b) salts formed with organic acids such as, for example, acetic acid, oxalic acid, tartaric acid, succinic acid, maleic acid, fumaric acid, gluconic acid, citric acid, malic acid, ascorbic acid, benzoic acid, isethionic acid, lactobionic acid, tannic acid, palmitic acid, alginic acid, polyglutamic acid, naphthalenesulfonic acid, methanesulfonic acid, p-toluenesulfonic acid, benzenesulfonic acid, naphthalenedisulfonic acid, polygalacturonic acid, malonic acid, sulfosalicylic acid, glycolic acid, 2-hydroxy-3-naphthoate, pamoate, salicylic acid, stearic acid, phthalic acid, mandelic acid, lactic acid, ethanesulfonic acid, lysine, arginine, glutamic acid, glycine, serine, threonine, alanine, isoleucine, leucine and the like; and (c) salts formed from elemental anions for example, chlorine, bromine, and iodine.

Physiologically acceptable salts of a compound of a hydroxy group include the anion of said compound in combination with a suitable cation such as Na⁺ and NR$^a_4$⁺.

For therapeutic use, salts of active ingredients of the compounds of the invention will be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived form a physiologically acceptable acid or base, are within the scope of the present invention. Finally, it is to be understood that the compositions herein comprise compounds of the invention in their un-ionized, as well as zwitterionic form, and combinations with stoichiometric amounts of water as in hydrates.

The compounds of the invention, exemplified by Formula I-XIV have chiral centers, e.g. chiral carbon or phosphorus atoms. For example, the phosphorous atoms of Formula I-XIV may be chiral because they have four different substituents. The compounds of the invention thus include racemic mixtures of all stereoisomers, including enantiomers, diastereomers, and atropisomers. In addition, the compounds of the invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures are separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, reactivities and biological properties. For example, the compounds of Formula I-XIV may have a chiral phosphorus atom when phosphorus has four different substitutents, e.g., Formula XIV, where the chirality is R or S. When R$^c$ and R$^d$ of the amino acid of the phosphoramidate of Formula IV are different, there are two centers of chirality in the molecule leading to potential diastereomeric mixtures of compounds, e.g. R,S; S,R; S,S and R,R isomers. Mixtures of diastereomers may be separate under high resolution analytical procedures such as electrophoresis, crystallization and/or chromatography. Diastereomers may have different physical attributes such as, but not limited to, solubility, chemical stabilities and crystallinity and may also have different biological properties sue as, but not limited to, enzymatic stability, absorption and metabolic stability.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., Stereochemistry of Organic Compounds (1994) John Wiley & Sons, Inc., New York. Many organic compounds exist in optically active forms, i.e. they have the ability to rotate the plane of plane-polarized light. In describing an optically active compound, the prefixes D and L or R and S are used to denote the absolute configuration of the molecule about its chiral center(s). The prefixes d and I, D and L, or (+) and (−) are employed to designate the sign of rotation of plane-polarized light by the compound, with S, (−), or I meaning that the compound is levorotatory while a compound prefixed with R, (+), or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Whenever a compound described herein is substituted with more than one of the same designated group, e.g., "R$^a$" or "R$^1$", then it will be understood that the groups may be the same or different, i.e. each group is independently selected. Wavy lines, 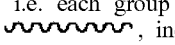, indicate the site of covalent bond attachments to the adjoining substructures, groups, moieties, or atoms.

The compounds of the invention can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

One skilled in the art will recognize that nucleoside bases such as the pyrrolo[1,2-f][1,2,4]triazine nucleosides can exist in tautomeric forms. For example, but not by way of limitation, structures (a) and (b) can have equivalent tautomeric forms as shown below:

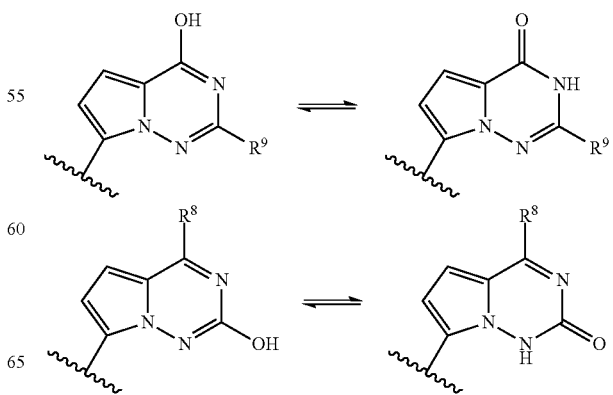

-continued

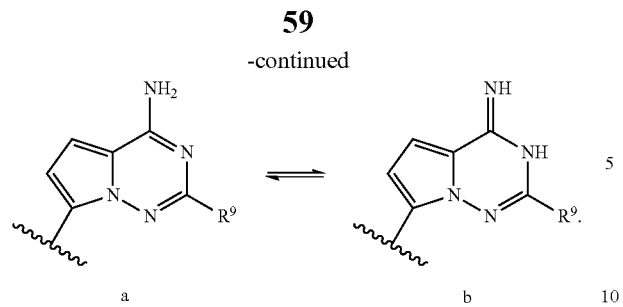

a            b

All possible tautomeric forms of the heterocycles and nucleobases in all of the embodiments disclosed herein are within the scope of the invention.

The compounds of Formula I-XIV also include molecules that incorporate isotopes of the atoms specified in the particular molecules. Non-limiting examples of these isotopes include D, T, $^{14}C$, 13C and $^{15}N$. All such isotopic variations of these molecules are provided by the instant invention.

Suitably isotopes of the atoms will be present in line with their natural abundance (i.e. there is no isotopic entrichment).

Suitably $R^5$ is H.

Suitably the methods, compounds and diasteremoners of the present invention do not encompass matter disclosed on WO2014/169278 (unpublished at the priority date of the present application and incorporated herein by reference for the specific purpose of disclaimer).

For example, the compound of Formula VIII is suitably not:

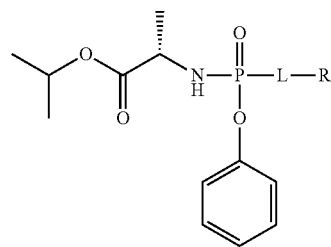

wherein L is S or O and R-LH is:

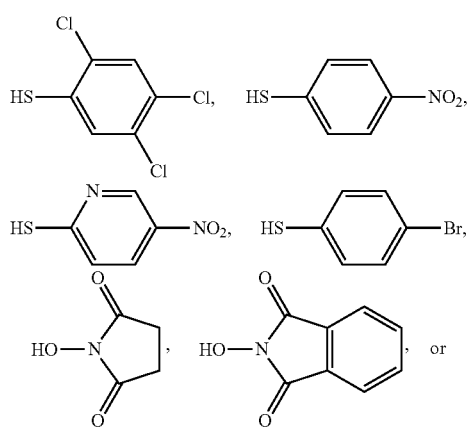

-continued

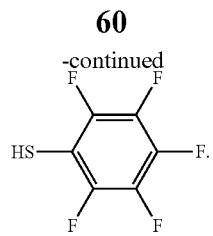

The compound of Formula VIII is also suitably not:

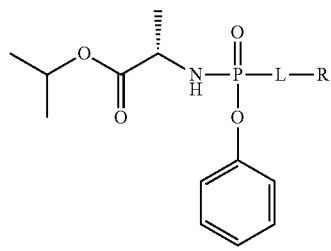

wherein R-LH is trichlorothiophenol, nitrothiophenol or bromothiophenol.

Alternatively, the compound of Formula VIII is suitably not:

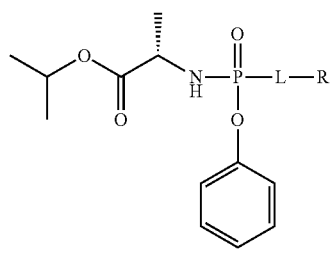

wherein L is S or O and R is an optionally substituted aryl, heteroaryl, or heterocycloalkyl group such as phenyl, pyrrole, pyridyl, pyridinyl, or indole;
wherein the term aryl indicates aromatic groups containing only carbon in the aromatic ring or rings. Aryl groups include, for example, phenyl and napthyl, including 1-napthyl and 2-napthyl; wherein the term heteroaryl indicates a stable monocyclic aromatic ring having the indicated number of ring atoms which contains from 1 to 3, or in some embodiments from 1 to 2, heteroatoms chosen from N, O, and S, with remaining ring atoms being carbon, or a stable bicyclic or tricyclic system containing at least one 5- to 7-membered aromatic ring which contains from 1 to 3, or in some embodiments from 1 to 2, heteroatoms chosen from N, O, and S, with remaining ring atoms being carbon. Monocyclic heteroaryl groups typically have from 5 to 7 ring atoms. In some embodiments bicyclic heteroaryl groups are 9- to 10-membered heteroaryl groups. It is preferred that the total number of S and O atoms in the heteroaryl group is not more than 2. Examples of heteroaryl groups include, thienyl pyridyl, pyrimidinyl, and pyrrolyl;
wherein the term heterocycloalkyl means a saturated ring group, having 1, 2, 3, or 4 heteroatoms independently chosen from N, S, and O, with remaining ring atoms being carbon. Monocyclic heterocycloalkyl groups typically have 4 to 6 ring atoms. Examples of heterocycloalkyl groups include morpholinyl, piperazinyl, piperidinyl, and pyrrolinyl;

wherein the term "substituted", means that any one or more hydrogens on the designated atom or group is replaced with a selection from the indicated group, provided that the designated atom's normal valence is not exceeded.

For example, the compound of Formula VIII or diastereomer of Formula III is suitably not:

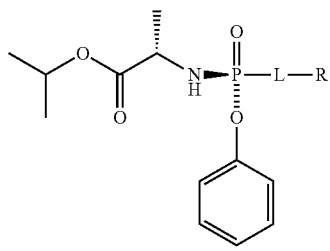

wherein L is S or O and R-LH is:

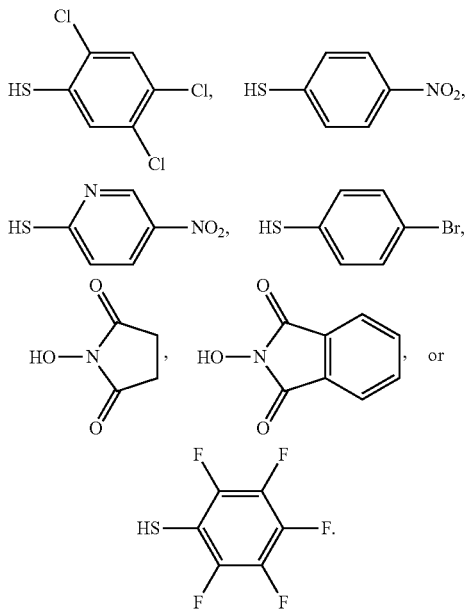

The compound of Formula VIII or diastereomer of Formula III is also suitably not:

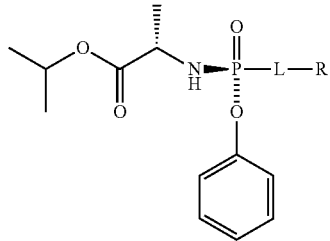

wherein R-LH is trichlorothiophenol, nitrothiophenol or bromothiophenol.

Alternatively, the compound of Formula VIII or diastereomer of Formula III is suitably not:

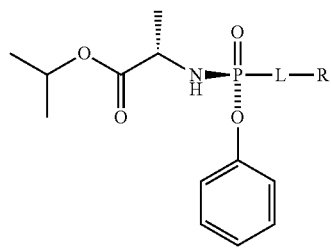

wherein L is S or O and R is an optionally substituted aryl, heteroaryl, or heterocycloalkyl group such as phenyl, pyrrole, pyridyl, pyridinyl, or indole;

wherein the term aryl indicates aromatic groups containing only carbon in the aromatic ring or rings. Aryl groups include, for example, phenyl and napthyl, including 1-napthyl and 2-napthyl; wherein the term heteroaryl indicates a stable monocyclic aromatic ring having the indicated number of ring atoms which contains from 1 to 3, or in some embodiments from 1 to 2, heteroatoms chosen from N, O, and S, with remaining ring atoms being carbon, or a stable bicyclic or tricyclic system containing at least one 5- to 7-membered aromatic ring which contains from 1 to 3, or in some embodiments from 1 to 2, heteroatoms chosen from N, O, and S, with remaining ring atoms being carbon. Monocyclic heteroaryl groups typically have from 5 to 7 ring atoms. In some embodiments bicyclic heteroaryl groups are 9- to 10-membered heteroaryl groups. It is preferred that the total number of S and O atoms in the heteroaryl group is not more than 2. Examples of heteroaryl groups include, thienyl pyridyl, pyrimidinyl, and pyrrolyl;

wherein the term heterocycloalkyl means a saturated ring group, having 1, 2, 3, or 4 heteroatoms independently chosen from N, S, and O, with remaining ring atoms being carbon. Monocyclic heterocycloalkyl groups typically have 4 to 6 ring atoms. Examples of heterocycloalkyl groups include morpholinyl, piperazinyl, piperidinyl, and pyrrolinyl;

wherein the term "substituted", means that any one or more hydrogens on the designated atom or group is replaced with a selection from the indicated group, provided that the designated atom's normal valence is not exceeded.

The compound of Formula VIII or diastereomer of Formula III is also suitably not:

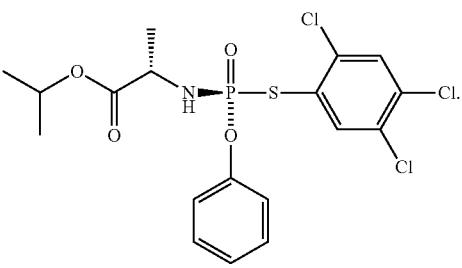

Suitably the methods, compounds and diasteremoners of the present invention do not encompass matter disclosed on WO2014/169280 (unpublished at the priority date of the present application and incorporated herein by reference for the specific purpose of disclaimer).

For example, the compound of Formula VIII is suitably not:

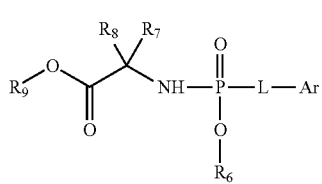

wherein L is S or O and Ar-LH is:

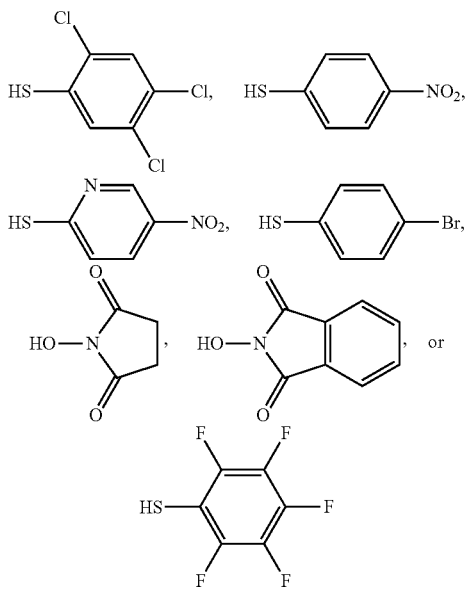

and wherein:

$R^6$ is $C_1$-$C_6$alkyl, allenyl, $C_2$-$C_6$alkenyl, $C_2$-$C_6$alkynyl, (aryl)$C_0$-$C_2$alkyl, or 5- to 6-membered monocyclic heteroaryl containing 1 to 3 heteroatoms independently chosen from N, O, and S, or 8- to 10-membered bicyclic heteroaryl containing 1 to 4 heteroatoms independently chosen from N, O, and S; each of which $R_6$ is optionally substituted;

$R^7$ is hydrogen, halogen, $C_1$-$C_2$haloalkyl, or $C_1$-$C_2$haloalkoxy; or $R^7$ is $C_1$-$C_6$alkyl, allenyl, $C_2$-$C_6$alkenyl, $C_2$-$C_6$alkynyl, $C_1$-$C_6$alkoxy, ($C_3$-$C_6$cycloalkyl)$C_0$-$C_4$alkyl, or (aryl)$C_0$-$C_2$alkyl; each of which is optionally substituted; and $R^8$ is hydrogen, halogen, $C_1$-$C_2$haloalkyl, or $C_1$-$C_2$haloalkoxy;

or $R^8$ is $C_1$-$C_6$alkyl, allenyl, $C_2$-$C_6$alkenyl, $C_2$-$C_6$alkynyl, or $C_1$-$C_6$alkoxy, each of which is optionally substituted;

or, $R_7$ and $R_8$ are taken together to form a 3- to 6-membered cycloalkyl ring or 3- to 6-membered heterocycloalkyl ring containing one heteroatom chosen from N, O, and S; each of which is optionally substituted;

$R_9$ is $C_1$-$C_6$alkyl, allenyl, $C_2$-$C_6$alkenyl, $C_2$-$C_6$alkynyl, ($C_3$-$C_7$cycloalkyl)$C_0$-$C_4$carbhydryl, (aryl)$C_0$-$C_4$carbhydryl, (3- to 6-membered heterocycloalkyl)$C_0$-$C_4$carbhydryl, or (heteroaryl)$C_0$-$C_4$carbhydryl, each of which is optionally substituted;

wherein:

a dash ("-") that is not between two letters or symbols is used to indicate a point of attachment for a substituent. For example, —(C═O)NH$_2$ is attached through carbon of the keto (C═O) group;

"Alkyl" is a branched or straight chain saturated aliphatic hydrocarbon group, having the specified number of carbon atoms, generally from 1 to about 12 carbon atoms. The term $C_1$-$C_6$alkyl as used herein indicates an alkyl group having from 1, 2, 3, 4, 5, or 6 carbon atoms. Other embodiments include alkyl groups having from 1 to 8 carbon atoms, 1 to 4 carbon atoms or 1 or 2 carbon atoms, e.g. $C_1$-$C_8$alkyl, $C_1$-$C_4$alkyl, and $C_1$-$C_2$alkyl. When $C_0$-$C_n$ alkyl is used herein in conjunction with another group, for example, ($C_3$-$C_7$cycloalkyl)$C_0$-$C_4$ alkyl, the indicated group, in this case cycloalkyl, is either directly bound by a single covalent bond ($C_0$alkyl), or attached by an alkyl chain having the specified number of carbon atoms, in this case 1, 2, 3, or 4 carbon atoms. Examples of alkyl include, but are not limited to, methyl, ethyl, n-propyl, isopropyl, n-butyl, 3-methylbutyl, t-butyl, n-pentyl, and sec-pentyl;

"Alkenyl" is a branched or straight chain aliphatic hydrocarbon group having one or more double carbon-carbon bonds that may occur at any stable point along the chain, having the specified number of carbon atoms. Examples of alkenyl include, but are not limited to, ethenyl and propenyl;

"Alkynyl" is a branched or straight chain aliphatic hydrocarbon group having one or more triple carbon-carbon bonds that may occur at any stable point along the chain, having the specified number of carbon atoms. Examples of alkynyl include, but are not limited to, ethynyl and propynyl;

"Allenyl" is an alkenyl group having two consecutive double bonds, i.e., a group of formula —C═C═CH$_2$;

"Alkoxy" is an alkyl group as defined above with the indicated number of carbon atoms covalently bound to the group it substitutes by an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy;

"Alkanoyl" is an alkyl group as defined above with the indicated number of carbon atoms covalently bound to the group is substitutes through a carbonyl (C═O) bridge. The carbonyl carbon is included in the number of carbons, that is $C_2$alkanoyl is a CH$_3$(C═O)— group;

"Alkylester" is an alkyl group as defined herein covalently bound to the group it substitutes by an ester linkage. The ester linkage may be in either orientation, e.g., a group of the formula —O(C═O)alkyl or a group of the formula —(C═O)Oalkyl;

"Cycloalkyl" is a saturated hydrocarbon ring group, having the specified number of carbon atoms. Monocyclic cycloalkyl groups typically have from 3 to about 8 carbon ring atoms or from 3 to 7 (3, 4, 5, 6, or 7) carbon ring atoms. Cycloalkyl substituents may be pendant from a substituted nitrogen or carbon atom, or a substituted carbon atom that may have two substituents may have a cycloalkyl group, which is attached as a spiro group. Examples of cycloalkyl groups include cyclopropyl, cyclobutyl, cyclopentyl, and cyclohexyl;

"Haloalkyl" indicates both branched and straight-chain alkyl groups having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, and penta-fluoroethyl;

"Haloalkoxy" indicates a haloalkyl group as defined herein attached through an oxygen bridge (oxygen of an alcohol radical);

"Halo" or "halogen" indicates any of fluoro, chloro, bromo, and iodo;

"Aryl" indicates aromatic groups containing only carbon in the aromatic ring or rings. Typical aryl groups contain 1 to 3 separate, fused, or pendant rings and from 6 to about 18 ring atoms, without heteroatoms as ring members. When indicated, such aryl groups may be further substituted with carbon or non-carbon atoms or groups. Such substitution may include fusion to a 5 to 7-membered saturated cyclic group that optionally contains 1 or 2 heteroatoms independently chosen from N, O, and S, to form, for example, a 3,4-methylenedioxy-phenyl group. Aryl groups include, for example, phenyl, naphthyl, including 1-naphthyl and 2-naphthyl, and bi-phenyl;

"Heteroaryl" indicates a stable monocyclic aromatic ring having the indicated number of ring atoms which contains from 1 to 3, or in some embodiments from 1 to 2, heteroatoms chosen from N, O, and S, with remaining ring atoms being carbon, or a stable bicyclic or tricyclic system containing at least one 5- to 7-membered aromatic ring which contains from 1 to 3, or in some embodiments from 1 to 2, heteroatoms chosen from N, O, and S, with remaining ring atoms being carbon. Monocyclic heteroaryl groups typically have from 5 to 7 ring atoms. In some embodiments bicyclic heteroaryl groups are 9- to 10-membered heteroaryl groups, that is, groups containing 9 or 10 ring atoms in which one 5- to 7-member aromatic ring is fused to a second aromatic or non-aromatic ring. When the total number of S and O atoms in the heteroaryl group exceeds 1, these heteroatoms are not adjacent to one another. It is preferred that the total number of S and O atoms in the heteroaryl group is not more than 2. It is particularly preferred that the total number of S and O atoms in the aromatic heterocycle is not more than 1. Examples of heteroaryl groups include, but are not limited to, oxazolyl, pyranyl, pyrazinyl, pyrazolopyrimidinyl, pyrazolyl, pyridizinyl, pyridyl, pyrimidinyl, pyrrolyl, quinolinyl, tetrazolyl, thiazolyl, thienylpyrazolyl, thiophenyl, triazolyl, benzo[i] oxazolyl, benzofuranyl, benzothiazolyl, benzothiophenyl, benzoxadiazolyl, dihydrobenzodioxynyl, furanyl, imidazolyl, indolyl, and isoxazolyl. "Heteroaryloxy" is a heteroaryl group as described bound to the group it substituted via an oxygen bridge;

"Heterocycloalkyl" is a saturated ring group, having 1, 2, 3, or 4 heteroatoms independently chosen from N, S, and O, with remaining ring atoms being carbon. Monocyclic heterocycloalkyl groups typically have from 3 to about 8 ring atoms or from 4 to 6 ring atoms. Examples of heterocycloalkyl groups include morpholinyl, piperazinyl, piperidinyl, and pyrrolinyl;

"Carbhydryl" is a saturated or unsaturated aliphatic group containing the indicated number of carbon atoms, "carbhydryl" may be used in conjunction with other groups, such as aryl, as in "(aryl)carbhydryl.";

the term "mono- and/or di-alkylamino" indicates secondary or tertiary alkyl amino groups, wherein the alkyl groups are independently chosen alkyl groups, as defined herein, having the indicated number of carbon atoms. The point of attachment of the alkylamino group is on the nitrogen. Examples of mono- and di-alkylamino groups include ethylamino, dimethylamino, and methyl-propyl-amino;

the term "substituted", as used herein, means that any one or more hydrogens on the designated atom or group is replaced with a selection from the indicated group, provided that the designated atom's normal valence is not exceeded. When the substituent is oxo (i.e., =O) then 2 hydrogens on the atom are replaced. When an oxo group substitutes aromatic moieties, the corresponding partially unsaturated ring replaces the aromatic ring. For example a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent. Unless otherwise specified substituents are named into the core structure. For example, it is to be understood that when aminoalkyl is listed as a possible substituent the point of attachment of this substituent to the core structure is in the alkyl portion. Suitable groups that may be present on a "substituted" or "optionally substituted" position include, but are not limited to, e.g., halogen; cyano; hydroxyl; nitro; azido; alkanoyl (such as a $C_2$-$C_6$ alkanoyl group); carboxamide; alkyl groups (including cycloalkyl groups) having 1 to about 8 carbon atoms, or 1 to about 6 carbon atoms; alkenyl and alkynyl groups including groups having one or more unsaturated linkages and from 2 to about 8, or 2 to about 6 carbon atoms; alkoxy groups having one or more oxygen linkages and from 1 to about 8, or from 1 to about 6 carbon atoms; aryloxy such as phenoxy; alkylthio groups including those having one or more thioether linkages and from 1 to about 8 carbon atoms, or from 1 to about 6 carbon atoms; alkylsulfinyl groups including those having one or more sulfinyl linkages and from 1 to about 8 carbon atoms, or from 1 to about 6 carbon atoms; alkylsulfonyl groups including those having one or more sulfonyl linkages and from 1 to about 8 carbon atoms, or from 1 to about 6 carbon atoms; aminoalkyl groups including groups having one or more N atoms and from 1 to about 8, or from 1 to about 6 carbon atoms; aryl having 6 or more carbons and one or more rings, (e.g., phenyl, biphenyl, naphthyl, or the like, each ring either substituted or unsubstituted aromatic); arylalkyl having 1 to 3 separate or fused rings and from 6 to about 18 ring carbon atoms, with benzyl being an exemplary arylalkyl group; arylalkoxy having 1 to 3 separate or fused rings and from 6 to about 18 ring carbon atoms, with benzyloxy being an exemplary arylalkoxy group; or a saturated, unsaturated, or aromatic heterocyclic group having 1 to 3 separate or fused rings with 3 to about 8 members per ring and one or more N, O or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such heterocyclic groups may be further substituted, e.g. with hydroxy, alkyl, alkoxy, halogen and amino. In certain embodiments "optionally substituted" includes one or more substituents independently chosen from halogen, hydroxyl, amino, cyano, —CHO, —COOH, —CONH$_2$, $C_1$-$C_6$alkyl, $C_2$-$C_6$alkenyl, $C_1$-$C_6$alkoxy, $C_2$-$C_6$alkanoyl, $C_1$-$C_6$alkylester, (mono- and di-$C_1$-$C_6$alkylamino)$C_0$-$C_2$alkyl, $C_1$-$C_2$haloalkyl, and $C_1$-$C_2$haloalkoxy;

in particular, compounds may be disclaimed wherein:

$R_6$ is $C_1$-$C_6$alkyl, allenyl, $C_2$-$C_6$alkenyl, $C_2$-$C_6$alkynyl, each of which optionally substituted;

$R_6$ is (aryl)$C_0$-$C_2$alkyl, a 5- to 6-membered monocyclic heteroaryl containing 1 to 3 heteroatoms independently chosen from N, O, and S, or 8- to 10-membered bicyclic heteroaryl containing 1 to 4 heteroatoms independently chosen from N, O, and S; each of which $R_6$ is optionally substituted;

$R_6$ is phenyl, pyridyl, naphthyl, or indolyl, each of which is optionally substituted with one or more substituents independently chosen from halogen, hydroxyl, $C_1$-$C_4$alkyl, $C_1$-$C_4$alkoxy, (mono- and di-$C_1$-$C_4$alkylamino)$C_0$-$C_2$alkyl, $C_1$-$C_2$haloalkyl, and $C_1$-$C_2$haloalkoxy;

$R_6$ is phenyl substituted with one or more substituents independently chosen from halogen, hydroxyl, amino, cyano, —CHO, —COOH, —CONH$_2$, $C_1$-$C_6$alkyl, $C_2$-$C_6$alkenyl, $C_1$-$C_6$alkoxy, $C_2$-$C_6$alkanoyl, $C_1$-$C_6$alkylester, (mono- and di-$C_1$-$C_6$alkylamino)$C_0$-$C_2$alkyl, $C_1$-$C_2$haloalkyl, and $C_1$-$C_2$haloalkoxy;

$R_6$ is unsubstituted phenyl;

$R_6$ is unsubstituted naphthyl;

in particular, compounds may be disclaimed wherein:

$R_7$ is hydrogen, halogen, $C_1$-$C_2$haloalkyl, or $C_1$-$C_2$haloalkoxy; or R7 is $C_1$-$C_6$alkyl, allenyl, $C_2$-$C_6$alkenyl, $C_2$-$C_6$alkynyl, $C_1$-$C_6$alkoxy, ($C_3$-$C_6$cycloalkyl)$C_0$-$C_4$alkyl, or (aryl)$C_0$-$C_2$alkyl; each of which is optionally substituted; and $R_8$ is hydrogen, halogen, $C_1$-$C_2$haloalkyl, or $C_1$-$C_2$haloalkoxy; or $R_8$ is $C_1$-$C_6$alkyl, allenyl, $C_2$-$C_6$alkenyl, $C_2$-$C_6$alkynyl, or $C_1$-$C_6$alkoxy, each of which is optionally substituted;

$R_7$ and $R_8$ are independently chosen from hydrogen, halogen, $C_1$-$C_4$alkyl, $C_1$-$C_4$alkoxy, $C_1$-$C_2$haloalkyl, and $C_1$-$C_2$haloalkoxy;

$R_7$ and $R_8$ are taken together to form a 3- to 6-membered cycloalkyl ring or 3- to 6-membered heterocycloalkyl ring containing one heteroatom chosen from N, O, and S; each of which is optionally substituted;

$R_7$ is $C_1$-$C_6$alkyl and $R_8$ is hydrogen, halogen, or $C_1$-$C_6$alkyl;

$R_7$ is methyl and $R_8$ is hydrogen;

in particular, compounds may be disclaimed wherein:

$R_9$ is $C_1$-$C_6$alkyl, ($C_3$-$C_7$cycloalkyl)$C_0$-$C_4$alkyl, or (phenyl)$C_0$-$C_4$alkyl, each of which is optionally substituted;

$R_9$ is $C_1$-$C_6$alkyl.

$R_9$ is ($C_3$-$C_7$cycloalkyl)$C_0$-$C_2$alkyl or (phenyl)$C_0$-$C_2$alkyl, each of which is optionally substituted with one or more substituents independently chosen from halogen, hydroxyl, $C_1$-$C_4$alkyl, $C_1$-$C_4$ alkoxy, (mono- and di-$C_1$-$C_6$alkylamino)$C_0$-$C_2$alkyl, $C_1$-$C_2$haloalkyl, and $C_1$-$C_2$haloalkoxy;

in particular, a group of compounds may be disclaimed wherein:

$R_6$ is phenyl, pyridyl, naphthyl, or indolyl, each of which is optionally substituted with one or more substituents independently chosen from halogen, hydroxyl, amino, cyano, —CHO, —COOH, —CONH$_2$, $C_1$-$C_6$alkyl, $C_2$-$C_6$alkenyl, $C_1$-$C_6$alkoxy, $C_2$-$C_6$alkanoyl, $C_1$-$C_6$alkylester, (mono- and di-$C_1$-$C_6$alkylamino)$C_0$-$C_2$alkyl, $C_1$-$C_2$haloalkyl, and $C_1$-$C_2$haloalkoxy; $R_7$ is hydrogen, halogen, $C_{1-6}$alkyl, $C_1$-$C_6$alkoxy, $C_1$-$C_2$haloalkyl, $C_1$-$C_2$haloalkoxy, ($C_3$-$C_6$cycloalkyl)$C_0$-$C_4$alkyl, or (aryl)$C_0$-$C_2$alkyl; and $R_8$ is hydrogen, halogen, $C_1$-$C_6$alkyl, $C_1$-$C_6$alkoxy, $C_1$-$C_2$haloalkyl, or $C_1$-$C_2$haloalkoxy; or, $R_7$ and $R_8$ are taken together to form a 3- to 6-membered cycloalkyl ring; $R_9$ is $C_1$-$C_6$alkyl, ($C_3$-$C_7$cycloalkyl)$C_0$-$C_4$alkyl, or (aryl)$C_0$-$C_4$alkyl, each of which is optionally substituted with one or more substituents independently chosen from halogen, hydroxyl, amino, cyano, —CHO, —COOH, —CONH$_2$, $C_1$-$C_6$alkyl, $C_2$-$C_6$alkenyl, $C_1$-$C_6$alkoxy, $C_2$-$C_6$alkanoyl, $C_1$-$C_6$alkylester, (mono- and di-$C_1$-$C_6$alkylamino)$C_0$-$C_2$alkyl, $C_1$-$C_2$haloalkyl, and $C_1$-$C_2$haloalkoxy;

in particular, a group of compounds may be disclaimed wherein:

$R_6$ is phenyl, pyridyl, naphthyl, or indolyl, each of which is optionally substituted with one or more substituents independently chosen from halogen, hydroxyl, $C_1$-$C_4$alkyl, $C_1$-$C_4$alkoxy, (mono- and di-$C_1$-$C_4$alkylamino)$C_0$-$C_2$alkyl, $C_1$-$C_2$haloalkyl, and $C_1$-$C_2$haloalkoxy; $R_7$ is hydrogen, halogen, $C_1$-$C_4$alkyl, $C_1$-$C_4$alkoxy, $C_1$-$C_2$haloalkyl, $C_1$-$C_2$haloalkoxy, ($C_3$-$C_6$cycloalkyl)$C_0$-$C_2$alkyl, or (phenyl)$C_0$-$C_2$alkyl; $R_8$ is hydrogen, halogen, $C_1$-$C_2$alkyl, or $C_1$-$C_2$alkoxy; $R_7$ and $R_8$ are taken together to form a 3- to 6-membered cycloalkyl ring; and $R_9$ is $C_1$-$C_6$alkyl, ($C_3$-$C_7$cycloalkyl)$C_0$-$C_2$alkyl, or (aryl)$C_0$-$C_2$alkyl, each of which is optionally substituted with one or more substituents independently chosen from halogen, hydroxyl, $C_1$-$C_4$alkyl, $C_1$-$C_4$alkoxy, (mono- and di-$C_1$-$C_6$alkylamino)$C_0$-$C_2$alkyl, $C_1$-$C_2$haloalkyl, and $C_1$-$C_2$haloalkoxy;

in particular, a group of compounds may be disclaimed wherein:

$R_6$ is phenyl, naphthyl, or indolyl; $R_7$ is hydrogen, halogen, or $C_1$-$C_4$alkyl; $R_8$ is hydrogen, halogen, $C_1$-$C_2$alkyl, or $C_1$-$C_2$alkoxy; and $R_9$ is $C_1$-$C_6$alkyl.

The compound of Formula VIII is also suitably not:

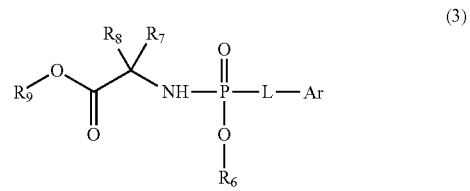

(3)

wherein Ar-LH is trichlorothiophenol, nitrothiophenol or bromothiophenol and $R^6$ is $C_1$-$C_6$alkyl, allenyl, $C_2$-$C_6$alkenyl, $C_2$-$C_6$alkynyl, (aryl)$C_0$-$C_2$alkyl, or 5- to 6-membered monocyclic heteroaryl containing 1 to 3 heteroatoms independently chosen from N, O, and S, or 8- to 10-membered bicyclic heteroaryl containing 1 to 4 heteroatoms independently chosen from N, O, and S; each of which $R_6$ is optionally substituted;

$R^7$ is hydrogen, halogen, $C_1$-$C_2$haloalkyl, or $C_1$-$C_2$haloalkoxy; or $R^7$ is $C_1$-$C_6$alkyl, allenyl, $C_2$-$C_6$alkenyl, $C_2$-$C_6$alkynyl, $C_1$-$C_6$alkoxy, ($C_3$-$C_6$cycloalkyl)$C_0$-$C_4$alkyl, or (aryl)$C_0$-$C_2$alkyl; each of which is optionally substituted; and $R^8$ is hydrogen, halogen, $C_1$-$C_2$haloalkyl, or $C_1$-$C_2$haloalkoxy;

or $R^8$ is $C_1$-$C_6$alkyl, allenyl, $C_2$-$C_6$alkenyl, $C_2$-$C_6$alkynyl, or $C_1$-$C_6$alkoxy, each of which is optionally substituted;

or, $R_7$ and $R_8$ are taken together to form a 3- to 6-membered cycloalkyl ring or 3- to 6-membered heterocycloalkyl ring containing one heteroatom chosen from N, O, and S; each of which is optionally substituted;

$R_9$ is $C_1$-$C_6$alkyl, allenyl, $C_2$-$C_6$alkenyl, $C_2$-$C_6$alkynyl, ($C_3$-$C_7$cycloalkyl)$C_0$-$C_4$carbhydryl, (aryl)$C_0$-$C_4$carbhydryl, (3- to 6-membered heterocycloalkyl)$C_0$-$C_4$carbhydryl, or (heteroaryl)$C_0$-$C_4$carbhydryl, each of which is optionally substituted;

wherein:

a dash ("-") that is not between two letters or symbols is used to indicate a point of attachment for a substituent. For example, —(C=O)NH$_2$ is attached through carbon of the keto (C=O) group;

"Alkyl" is a branched or straight chain saturated aliphatic hydrocarbon group, having the specified number of carbon atoms, generally from 1 to about 12 carbon atoms. The term $C_1$-$C_6$alkyl as used herein indicates an alkyl group having from 1, 2, 3, 4, 5, or 6 carbon atoms. Other embodiments include alkyl groups having from 1 to 8 carbon atoms, 1 to 4 carbon atoms or 1 or 2 carbon atoms, e.g. $C_1$-$C_8$alkyl, $C_1$-$C_4$alkyl, and $C_1$-$C_2$alkyl. When $C_0$-$C_n$ alkyl is used herein in conjunction with another group, for example, ($C_3$-$C_7$cycloalkyl)$C_0$-$C_4$ alkyl, the indicated group, in this case cycloalkyl, is either directly bound by a single covalent bond ($C_0$alkyl), or attached by an alkyl chain having the specified number of carbon atoms, in this case 1, 2, 3, or 4 carbon atoms. Examples of alkyl include, but are not limited to, methyl, ethyl, n-propyl, isopropyl, n-butyl, 3-methylbutyl, t-butyl, n-pentyl, and sec-pentyl;

"Alkenyl" is a branched or straight chain aliphatic hydrocarbon group having one or more double carbon-carbon bonds that may occur at any stable point along the chain, having the specified number of carbon atoms. Examples of alkenyl include, but are not limited to, ethenyl and propenyl;

"Alkynyl" is a branched or straight chain aliphatic hydrocarbon group having one or more triple carbon-carbon bonds that may occur at any stable point along the chain, having the specified number of carbon atoms. Examples of alkynyl include, but are not limited to, ethynyl and propynyl;

"Allenyl" is an alkenyl group having two consecutive double bonds, i.e., a group of formula —C═C═CH$_2$;

"Alkoxy" is an alkyl group as defined above with the indicated number of carbon atoms covalently bound to the group it substitutes by an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy;

"Alkanoyl" is an alkyl group as defined above with the indicated number of carbon atoms covalently bound to the group is substitutes through a carbonyl (C═O) bridge. The carbonyl carbon is included in the number of carbons, that is C$_2$alkanoyl is a CH$_3$(C═O)— group;

"Alkylester" is an alkyl group as defined herein covalently bound to the group it substitutes by an ester linkage. The ester linkage may be in either orientation, e.g., a group of the formula —O(C═O)alkyl or a group of the formula —(C═O)Oalkyl;

"Cycloalkyl" is a saturated hydrocarbon ring group, having the specified number of carbon atoms. Monocyclic cycloalkyl groups typically have from 3 to about 8 carbon ring atoms or from 3 to 7 (3, 4, 5, 6, or 7) carbon ring atoms. Cycloalkyl substituents may be pendant from a substituted nitrogen or carbon atom, or a substituted carbon atom that may have two substituents may have a cycloalkyl group, which is attached as a spiro group. Examples of cycloalkyl groups include cyclopropyl, cyclobutyl, cyclopentyl, and cyclohexyl;

"Haloalkyl" indicates both branched and straight-chain alkyl groups having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, and penta-fluoroethyl;

"Haloalkoxy" indicates a haloalkyl group as defined herein attached through an oxygen bridge (oxygen of an alcohol radical);

"Halo" or "halogen" indicates any of fluoro, chloro, bromo, and iodo;

"Aryl" indicates aromatic groups containing only carbon in the aromatic ring or rings. Typical aryl groups contain 1 to 3 separate, fused, or pendant rings and from 6 to about 18 ring atoms, without heteroatoms as ring members. When indicated, such aryl groups may be further substituted with carbon or non-carbon atoms or groups. Such substitution may include fusion to a 5 to 7-membered saturated cyclic group that optionally contains 1 or 2 heteroatoms independently chosen from N, O, and S, to form, for example, a 3,4-methylenedioxy-phenyl group. Aryl groups include, for example, phenyl, naphthyl, including 1-naphthyl and 2-naphthyl, and bi-phenyl;

"Heteroaryl" indicates a stable monocyclic aromatic ring having the indicated number of ring atoms which contains from 1 to 3, or in some embodiments from 1 to 2, heteroatoms chosen from N, O, and S, with remaining ring atoms being carbon, or a stable bicyclic or tricyclic system containing at least one 5- to 7-membered aromatic ring which contains from 1 to 3, or in some embodiments from 1 to 2, heteroatoms chosen from N, O, and S, with remaining ring atoms being carbon. Monocyclic heteroaryl groups typically have from 5 to 7 ring atoms. In some embodiments bicyclic heteroaryl groups are 9- to 10-membered heteroaryl groups, that is, groups containing 9 or 10 ring atoms in which one 5- to 7-member aromatic ring is fused to a second aromatic or non-aromatic ring. When the total number of S and O atoms in the heteroaryl group exceeds 1, these heteroatoms are not adjacent to one another. It is preferred that the total number of S and O atoms in the heteroaryl group is not more than 2. It is particularly preferred that the total number of S and O atoms in the aromatic heterocycle is not more than 1. Examples of heteroaryl groups include, but are not limited to, oxazolyl, pyranyl, pyrazinyl, pyrazolopyrimidinyl, pyrazolyl, pyridizinyl, pyridyl, pyrimidinyl, pyrrolyl, quinolinyl, tetrazolyl, thiazolyl, thienylpyrazolyl, thiophenyl, triazolyl, benzo[i] oxazolyl, benzofuranyl, benzothiazolyl, benzothiophenyl, benzoxadiazolyl, dihydrobenzodioxynyl, furanyl, imidazolyl, indolyl, and isoxazolyl. "Heteroaryloxy" is a heteroaryl group as described bound to the group it substituted via an oxygen bridge;

"Heterocycloalkyl" is a saturated ring group, having 1, 2, 3, or 4 heteroatoms independently chosen from N, S, and O, with remaining ring atoms being carbon. Monocyclic heterocycloalkyl groups typically have from 3 to about 8 ring atoms or from 4 to 6 ring atoms. Examples of heterocycloalkyl groups include morpholinyl, piperazinyl, piperidinyl, and pyrrolinyl;

"Carbhydryl" is a saturated or unsaturated aliphatic group containing the indicated number of carbon atoms, "carbhydryl" may be used in conjunction with other groups, such as aryl, as in "(aryl)carbhydryl.";

the term "mono- and/or di-alkylamino" indicates secondary or tertiary alkyl amino groups, wherein the alkyl groups are independently chosen alkyl groups, as defined herein, having the indicated number of carbon atoms. The point of attachment of the alkylamino group is on the nitrogen. Examples of mono- and di-alkylamino groups include ethylamino, dimethylamino, and methyl-propyl-amino;

the term "substituted", as used herein, means that any one or more hydrogens on the designated atom or group is replaced with a selection from the indicated group, provided that the designated atom's normal valence is not exceeded. When the substituent is oxo (i.e., ═O) then 2 hydrogens on the atom are replaced. When an oxo group substitutes aromatic moieties, the corresponding partially unsaturated ring replaces the aromatic ring. For example a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent. Unless otherwise specified substituents are named into the core structure. For example, it is to be understood that when aminoalkyl is listed as a possible substituent the point of attachment of this substituent to the core structure is in the alkyl portion. Suitable groups that may be present on a "substituted" or "optionally substituted" position include, but are not limited to, e.g., halogen; cyano; hydroxyl; nitro; azido; alkanoyl (such as a C$_2$-C$_6$ alkanoyl group); carboxamide; alkyl groups (including cycloalkyl groups) having 1 to about 8 carbon atoms, or 1 to about 6 carbon atoms; alkenyl and alkynyl groups including groups having one or more unsaturated linkages and from 2 to about 8, or 2 to about 6 carbon atoms; alkoxy groups having one or more oxygen linkages and from 1 to about 8, or from 1 to about 6 carbon atoms; aryloxy such as phenoxy; alkylthio groups including those having one or more thioether linkages and from 1 to about 8 carbon atoms, or from 1 to about 6 carbon atoms; alkylsulfinyl groups including those having one or more sulfinyl linkages and from 1 to about 8 carbon atoms, or from 1 to about 6 carbon atoms; alkylsulfonyl groups including those having one or more sulfonyl linkages and from 1 to about 8 carbon atoms, or from 1 to about 6 carbon atoms; aminoalkyl groups including groups having one or more N atoms and from 1 to about 8, or from 1 to about 6 carbon atoms; aryl having 6 or more carbons and one or more rings, (e.g., phenyl, biphenyl, naphthyl, or the like, each ring either substituted or unsubstituted aromatic); arylalkyl having 1 to 3 separate or fused rings and from 6 to about 18 ring carbon atoms, with benzyl being an exemplary arylalkyl group; arylalkoxy having 1 to 3 separate or fused rings and from 6 to about 18 ring carbon atoms, with benzyloxy being an exemplary arylalkoxy group; or a saturated, unsaturated, or aromatic heterocyclic group having 1 to 3 separate or fused rings with 3 to about 8 members per ring and one or more N, O or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such heterocyclic groups may be further substituted, e.g. with hydroxy, alkyl, alkoxy, halogen and amino. In certain embodiments "optionally substituted" includes one or more substituents independently chosen from halogen, hydroxyl, amino, cyano, —CHO, —COOH, —CONH$_2$, C$_1$-C$_6$alkyl, C$_2$-C$_6$alkenyl, C$_1$-C$_6$alkoxy, C$_2$-C$_6$alkanoyl, C$_1$-C$_6$alkylester, (mono- and di-C$_1$-C$_6$alkylamino)C$_0$-C$_2$alkyl, C$_1$-C$_2$haloalkyl, and C$_1$-C$_2$haloalkoxy;

in particular, compounds may be disclaimed wherein:

R$_6$ is C$_1$-C$_6$alkyl, allenyl, C$_2$-C$_6$alkenyl, C$_2$-C$_6$alkynyl, each of which optionally substituted;

R$_6$ is (aryl)C$_0$-C$_2$alkyl, a 5- to 6-membered monocyclic heteroaryl containing 1 to 3 heteroatoms independently chosen from N, O, and S, or 8- to 10-membered bicyclic heteroaryl containing 1 to 4 heteroatoms independently chosen from N, O, and S; each of which R$_6$ is optionally substituted;

R$_6$ is phenyl, pyridyl, naphthyl, or indolyl, each of which is optionally substituted with one or more substituents independently chosen from halogen, hydroxyl, C$_1$-C$_4$alkyl, C$_1$-C$_4$alkoxy, (mono- and di-C$_1$-C$_4$alkylamino)C$_0$-C$_2$alkyl, C$_1$-C$_2$haloalkyl, and C$_1$-C$_2$haloalkoxy;

R$_6$ is phenyl substituted with one or more substituents independently chosen from halogen, hydroxyl, amino, cyano, —CHO, —COOH, —CONH$_2$, C$_1$-C$_6$alkyl, C$_2$-C$_6$alkenyl, C$_1$-C$_6$alkoxy, C$_2$-C$_6$alkanoyl, C$_1$-C$_6$alkylester, (mono- and di-C$_1$-C$_6$alkylamino)C$_0$-C$_2$alkyl, C$_1$-C$_2$haloalkyl, and C$_1$-C$_2$haloalkoxy;

R$_6$ is unsubstituted phenyl;

R$_6$ is unsubstituted naphthyl;

in particular, compounds may be disclaimed wherein:

R$_7$ is hydrogen, halogen, C$_1$-C$_2$haloalkyl, or C$_1$-C$_2$haloalkoxy; or R7 is C$_1$-C$_6$alkyl, allenyl, C$_2$-C$_6$alkenyl, C$_2$-C$_6$alkynyl, C$_1$-C$_6$alkoxy, (C$_3$-C$_6$cycloalkyl)C$_0$-C$_4$alkyl, or (aryl)C$_0$-C$_2$alkyl; each of which is optionally substituted; and R$_8$ is hydrogen, halogen, C$_1$-C$_2$haloalkyl, or C$_1$-C$_2$haloalkoxy; or R$_8$ is C$_1$-C$_6$alkyl, allenyl, C$_2$-C$_6$alkenyl, C$_2$-C$_6$alkynyl, or C$_1$-C$_6$alkoxy, each of which is optionally substituted;

R$_7$ and R$_8$ are independently chosen from hydrogen, halogen, C$_1$-C$_4$alkyl, C$_1$-C$_4$alkoxy, C$_1$-C$_2$haloalkyl, and C$_1$-C$_2$haloalkoxy;

R$_7$ and R$_8$ are taken together to form a 3- to 6-membered cycloalkyl ring or 3- to 6-membered heterocycloalkyl ring containing one heteroatom chosen from N, O, and S; each of which is optionally substituted;

R$_7$ is C$_1$-C$_6$alkyl and R$_8$ is hydrogen, halogen, or C$_1$-C$_6$alkyl;

R$_7$ is methyl and R$_8$ is hydrogen;

in particular, compounds may be disclaimed wherein:

R$_9$ is C$_1$-C$_6$alkyl, (C$_3$-C$_7$cycloalkyl)C$_0$-C$_4$alkyl, or (phenyl)C$_0$-C$_4$alkyl, each of which is optionally substituted;

R$_9$ is C$_1$-C$_6$alkyl.

R$_9$ is (C$_3$-C$_7$cycloalkyl)C$_0$-C$_2$alkyl or (phenyl)C$_0$-C$_2$alkyl, each of which is optionally substituted with one or more substituents independently chosen from halogen, hydroxyl, C$_1$-C$_4$alkyl, C$_1$-C$_4$ alkoxy, (mono- and di-C$_1$-C$_6$alkylamino)C$_0$-C$_2$alkyl, C$_1$-C$_2$haloalkyl, and C$_1$-C$_2$haloalkoxy;

in particular, a group of compounds may be disclaimed wherein:

R$_6$ is phenyl, pyridyl, naphthyl, or indolyl, each of which is optionally substituted with one or more substituents independently chosen from halogen, hydroxyl, amino, cyano, —CHO, —COOH, —CONH$_2$, C$_1$-C$_6$alkyl, C$_2$-C$_6$alkenyl, C$_1$-C$_6$alkoxy, C$_2$-C$_6$alkanoyl, C$_1$-C$_6$alkylester, (mono- and di-C$_1$-C$_6$alkylamino)C$_0$-C$_2$alkyl, C$_1$-C$_2$haloalkyl, and C$_1$-C$_2$haloalkoxy; R$_7$ is hydrogen, halogen, C$_{1-6}$alkyl, C$_1$-C$_6$alkoxy, C$_1$-C$_2$haloalkyl, C$_1$-C$_2$haloalkoxy, (C$_3$-C$_6$cycloalkyl)C$_0$-C$_4$alkyl, or (aryl)C$_0$-C$_2$alkyl; and R$_8$ is hydrogen, halogen, C$_1$-C$_6$alkyl, C$_1$-C$_6$alkoxy, C$_1$-C$_2$haloalkyl, or C$_1$-C$_2$haloalkoxy; or, R$_7$ and R$_8$ are taken together to form a 3- to 6-membered cycloalkyl ring; R$_9$ is C$_1$-C$_6$alkyl, (C$_3$-C$_7$cycloalkyl)C$_0$-C$_4$alkyl, or (aryl)C$_0$-C$_4$alkyl, each of which is optionally substituted with one or more substituents independently chosen from halogen, hydroxyl, amino, cyano, —CHO, —COOH, —CONH$_2$, C$_1$-C$_6$alkyl, C$_2$-C$_6$alkenyl, C$_1$-C$_6$alkoxy, C$_2$-C$_6$alkanoyl, C$_1$-C$_6$alkylester, (mono- and di-C$_1$-C$_6$alkylamino)C$_0$-C$_2$alkyl, C$_1$-C$_2$haloalkyl, and C$_1$-C$_2$haloalkoxy;

in particular, a group of compounds may be disclaimed wherein:

R$_6$ is phenyl, pyridyl, naphthyl, or indolyl, each of which is optionally substituted with one or more substituents independently chosen from halogen, hydroxyl, C$_1$-C$_4$alkyl, C$_1$-C$_4$alkoxy, (mono- and di-C$_1$-C$_4$alkylamino)C$_0$-C$_2$alkyl, C$_1$-C$_2$haloalkyl, and C$_1$-C$_2$haloalkoxy; R$_7$ is hydrogen, halogen, C$_1$-C$_4$alkyl, C$_1$-C$_4$alkoxy, C$_1$-C$_2$haloalkyl, C$_1$-C$_2$haloalkoxy, (C$_3$-C$_6$cycloalkyl)C$_0$-C$_2$alkyl, or (phenyl)C$_0$-C$_2$alkyl; R$_8$ is hydrogen, halogen, C$_1$-C$_2$alkyl, or C$_1$-C$_2$alkoxy; R$_7$ and R$_8$ are taken together to form a 3- to 6-membered cycloalkyl ring; and R$_9$ is C$_1$-C$_6$alkyl, (C$_3$-C$_7$cycloalkyl)C$_0$-C$_2$alkyl, or (aryl)C$_0$-C$_2$alkyl, each of which is optionally substituted with one or more substituents independently chosen from halogen, hydroxyl, C$_1$-C$_4$alkyl, C$_1$-C$_4$alkoxy, (mono- and di-C$_1$-C$_6$alkylamino)C$_0$-C$_2$alkyl, C$_1$-C$_2$haloalkyl, and C$_1$-C$_2$haloalkoxy;

in particular, a group of compounds may be disclaimed wherein:

R$_6$ is phenyl, naphthyl, or indolyl; R$_7$ is hydrogen, halogen, or C$_1$-C$_4$alkyl; R$_8$ is hydrogen, halogen, C$_1$-C$_2$alkyl, or C$_1$-C$_2$alkoxy; and R$_9$ is C$_1$-C$_6$alkyl.

For example, the compound of Formula VIII or diastereomer of Formula III is suitably not:

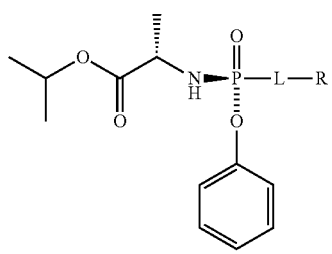

wherein L is S or O and R-LH is:

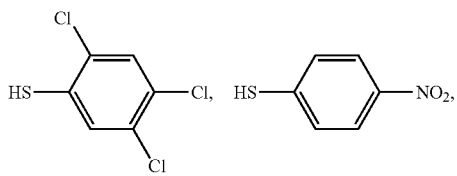

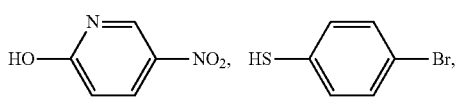

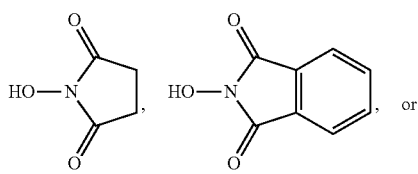

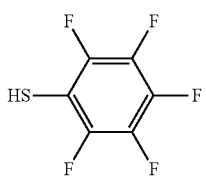, or

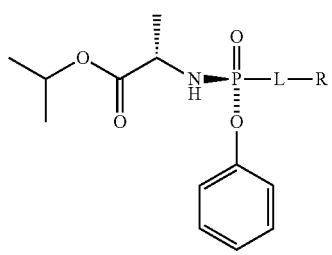

The compound of Formula VIII or diastereomer of Formula III is also suitably not:

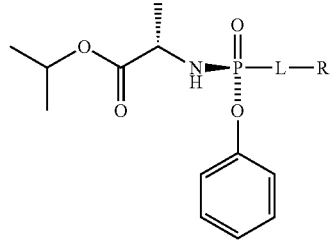

wherein R-LH is trichlorothiophenol, nitrothiophenol or bromothiophenol.

Alternatively, the compound of Formula VIII or diastereomer of Formula III is suitably not:

wherein L is S or O and R is an optionally substituted aryl, heteroaryl, or heterocycloalkyl group such as phenyl, pyrrole, pyridyl, pyridinyl, or indole;

wherein "Aryl" indicates aromatic groups containing only carbon in the aromatic ring or rings. Typical aryl groups contain 1 to 3 separate, fused, or pendant rings and from 6 to about 18 ring atoms, without heteroatoms as ring members. When indicated, such aryl groups may be further substituted with carbon or non-carbon atoms or groups. Such substitution may include fusion to a 5 to 7-membered saturated cyclic group that optionally contains 1 or 2 heteroatoms independently chosen from N, O, and S, to form, for example, a 3,4-methylenedioxy-phenyl group. Aryl groups include, for example, phenyl, naphthyl, including 1-naphthyl and 2-naphthyl, and bi-phenyl;

"Heteroaryl" indicates a stable monocyclic aromatic ring having the indicated number of ring atoms which contains from 1 to 3, or in some embodiments from 1 to 2, heteroatoms chosen from N, O, and S, with remaining ring atoms being carbon, or a stable bicyclic or tricyclic system containing at least one 5- to 7-membered aromatic ring which contains from 1 to 3, or in some embodiments from 1 to 2, heteroatoms chosen from N, O, and S, with remaining ring atoms being carbon. Monocyclic heteroaryl groups typically have from 5 to 7 ring atoms. In some embodiments bicyclic heteroaryl groups are 9- to 10-membered heteroaryl groups, that is, groups containing 9 or 10 ring atoms in which one 5- to 7-member aromatic ring is fused to a second aromatic or non-aromatic ring. When the total number of S and O atoms in the heteroaryl group exceeds 1, these heteroatoms are not adjacent to one another. It is preferred that the total number of S and O atoms in the heteroaryl group is not more than 2. It is particularly preferred that the total number of S and O atoms in the aromatic heterocycle is not more than 1. Examples of heteroaryl groups include, but are not limited to, oxazolyl, pyranyl, pyrazinyl, pyrazolopyrimidinyl, pyrazolyl, pyridizinyl, pyridyl, pyrimidinyl, pyrrolyl, quinolinyl, tetrazolyl, thiazolyl, thienylpyrazolyl, thiophenyl, triazolyl, benzo[i] oxazolyl, benzofuranyl, benzothiazolyl, benzothiophenyl, benzoxadiazolyl, dihydrobenzodioxynyl, furanyl, imidazolyl, indolyl, and isoxazolyl;

"Heterocycloalkyl" is a saturated ring group, having 1, 2, 3, or 4 heteroatoms independently chosen from N, S, and O, with remaining ring atoms being carbon. Monocyclic heterocycloalkyl groups typically have from 3 to about 8 ring atoms or from 4 to 6 ring atoms. Examples of heterocycloalkyl groups include morpholinyl, piperazinyl, piperidinyl, and pyrrolinyl;

the term "substituted", as used herein, means that any one or more hydrogens on the designated atom or group is replaced with a selection from the indicated group, provided that the designated atom's normal valence is not exceeded. When the substituent is oxo (i.e., =O) then 2 hydrogens on the atom are replaced. When an oxo group substitutes aromatic moieties, the corresponding partially unsaturated ring replaces the aromatic ring. For example a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent. Unless otherwise specified substituents are named into the core structure. For example, it is to be understood that when aminoalkyl is listed as a possible substituent the point of attachment of this substituent to the core structure is in the alkyl portion. Suitable groups that may be present on a "substituted" or "optionally substituted" position include, but are not limited to, e.g., halogen; cyano; hydroxyl; nitro; azido; alkanoyl (such as a $C_2$-$C_6$ alkanoyl group); carboxamide; alkyl groups (including cycloalkyl groups) having 1 to about 8 carbon atoms, or 1 to about 6 carbon atoms; alkenyl and alkynyl groups including groups having one or more unsaturated linkages and from 2 to about 8, or 2 to about 6 carbon atoms; alkoxy groups having one or more oxygen linkages and from 1 to about 8, or from 1 to about 6 carbon atoms; aryloxy such as phenoxy; alkylthio groups including those having one or more thioether linkages and from 1 to about 8 carbon atoms, or from 1 to about 6 carbon atoms; alkylsulfinyl groups including those having one or more sulfinyl linkages and from 1 to about 8 carbon atoms, or from 1 to about 6 carbon atoms; alkylsulfonyl groups including those having one or more sulfonyl linkages and from 1 to about 8 carbon atoms, or from 1 to about 6 carbon atoms; aminoalkyl groups including groups having one or more N atoms and from 1 to about 8, or from 1 to about 6 carbon atoms; aryl having 6 or more carbons and one or more rings, (e.g., phenyl, biphenyl, naphthyl, or the like, each ring either substituted or unsubstituted aromatic); arylalkyl having 1 to 3 separate or fused rings and from 6 to about 18 ring carbon atoms, with benzyl being an exemplary arylalkyl group; arylalkoxy having 1 to 3 separate or fused rings and from 6 to about 18 ring carbon atoms, with benzyloxy being an exemplary arylalkoxy group; or a saturated, unsaturated, or aromatic heterocyclic group having 1 to 3 separate or fused rings with 3 to about 8 members per ring and one or more N, O or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such heterocyclic groups may be further substituted, e.g. with hydroxy, alkyl, alkoxy, halogen and amino. In certain embodiments "optionally substituted" includes one or more substituents independently chosen from halogen, hydroxyl, amino, cyano, —CHO, —COOH, —CONH$_2$, $C_1$-$C_6$alkyl, $C_2$-$C_6$alkenyl, $C_1$-$C_6$alkoxy, $C_2$-$C_6$alkanoyl, $C_1$-$C_6$alkylester, (mono- and di-$C_1$-$C_6$alkylamino)$C_0$-$C_2$alkyl, $C_1$-$C_2$haloalkyl, and $C_1$-$C_2$haloalkoxy.

The compound of Formula VIII or diastereomer of Formula III is also suitably not:

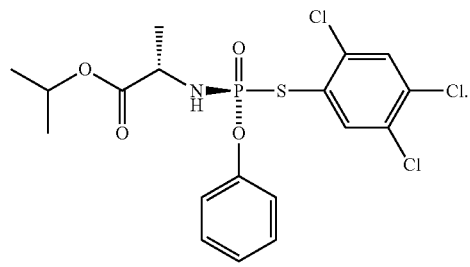

DETAILED DESCRIPTION OF THE EMBODIMENTS

Various embodiments of the invention will now be illustrated by the following examples. The Examples are just intended to further illustrate the invention and are by no means limiting the scope of the invention. The compound names were generated by ChemDraw Ultra software, Cambridgesoft, version 12.0.2.

Certain abbreviations and acronyms are used in describing the experimental details. Although most of these would be understood by one skilled in the art, Table 1 contains a list of many of these abbreviations and acronyms.

TABLE 1

| | List of abbreviations and acronyms. |
|---|---|
| Ac | acetyl |
| Bz | benzoyl |
| DCM | dichloromethane |
| DIBAL | Diisobutylaluminium hydride |
| DMAP | 4-dimethylaminopyridine |
| DME | 1,2-dimethoxyethane |
| DMSO | dimethylsulfoxide |
| DMF | dimethylform amide |
| dr | diastereomeric ratio |
| EtOAc | ethyl acetate |
| ES | electrospray ionization |
| ES+ | electrospray ionization positive mode |
| ES− | electrospray ionizationnegative mode |
| HMDS | hexamethyldisilazane |
| HPLC | High performance liquid chromatography |
| LDA | lithium diisopropylamide |
| mCPBA | meta-chloroperbenzoic acid |
| MeCN | acetonitrile |
| MeOH | methanol |
| m/z or m/e | mass to charge ratio |
| [MH]$^+$ | mass plus 1 |
| [MH]$^-$ | mass minus 1 |
| MsOH | methanesulfonic acid |
| Ms | methanesulfonyl |
| MS or ms | mass spectrum |
| NBS | N-bromosuccinimide |
| NCS | N-chlorosuccinimide |
| NFSI | N-fluorobenzenesulfonimide |
| NMR | nuclear magnetic resonance |
| rt | room temperature |
| TBAF | tetrabutylammonium fluoride |
| TMSCl | chlorotrimethylsilane |
| TMSBr | bromotrimethylsilane |
| TMSI | iodotrimethylsilane |
| TEA or Et$_3$N | triethylamine |
| TBA | tributylamine |
| TBAP | tributyl ammonium pyrophosphate |
| TBSCl | t-butyldimethylsilyl chloride |
| TEAB | triethylammonium bicarbonate |
| TFA | trifluoroacetic acid |
| TIPS | triisopropylsilyl |
| TIPS-Cl | triisopropylsilyl chloride |
| TLC | thin layer chromatography |
| Tr | triphenylmethyl |

TABLE 1-continued

List of abbreviations and acronyms.

| | |
|---|---|
| Tol | 4-methylbenzoyl |
| δ | parts per million down field from tetramethylsilane |

Example R1

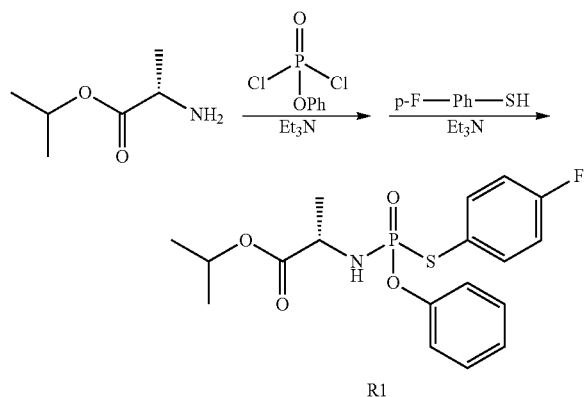

R1

(2S)-Isopropyl 2-((((4-fluorophenyl)thio)(phenoxy)phosphohoryl)amino)propanoate (R1)

Phenyl dichlorophosphate (1.30 g, 6.14 mmol) was added under nitrogen to a solution at −10° C. of (S)-isopropyl 2-aminopropanoate hydrochloride (1.03 g, 6.14 mmol) in DCM (10 mL) followed by dropwise addition of triethylamine (2 eq.) over 20 min. The mixture was stirred between −10° C. and 0° C. for 1 h, then cooled to −10° C. and a solution of 4-fluorothiophenol in DCM (2 mL) was added followed by dropwise addition of triethylamine (1.1 eq.) over 10-15 min. The reaction was stirred for 30 min, then solids were filtered off and the solids were washed with DCM (10 mL) and discarded. The solution was concentrated, the residue taken into ethyl acetate (15 mL) and remaining solids were removed by filtration and the solids were washed with ethyl acetate (5 mL). The solution was concentrated and the residue dried under vacuum which gave the title compound as a colourless oil (2.33 g, 95%). $^{31}$P-NMR showed a 1:1 mixture of P-diastereomers. The racemic reagent was used in coupling to the nucleoside.

Example R2

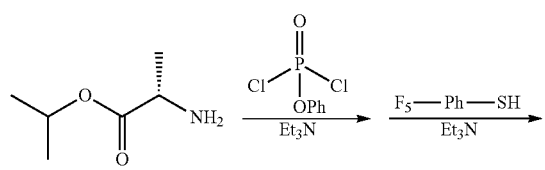

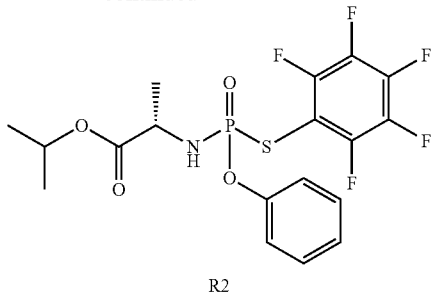

R2

(2S)-Isopropyl 2-((((perfluorophenyl)thio)(phenoxy)phosphoryl)amino)propanoate (R2)

Phenyl dichlorophosphate (2.60 g, 11.9 mmol) was added under N$_2$ to a solution at −10° C. of (S)-isopropyl 2-aminopropanoate hydrochloride (2.00 g, 11.9 mmol) in dry DCM (20 mL) followed by dropwise addition of Et$_3$N (2.1 Eq.) over 20 min. The thick white slurry was stirred at −10° C. for 45 min, then pentafluorothiophenol (2.46 g, 11.9 mmol) in dry DCM (4 mL) was added via syringe followed by dropwise addition of Et$_3$N (1.1 eq.) over 10 min. The reaction mixture was stirred at −10° C. for 30 min, then the precipitate was filtered off and the filtrated was diluted with methyl tert-butyl ether (40 mL). The organic layer was washed with HCl (0.1 M aq.), twice with KHCO$_3$ (sat. aq.), dried (MgSO$_4$) and concentrated under reduced pressure. The residue was purified by flash chromatography (hexane:EtOAc 5:1) which gave a diastereomeric mixture on the P-atom of the title compound; one pure fraction (900 mg, 16%, diastereomeric ratio 44:56) and one impure fraction (1.05 g, 19%, diastereomeric ratio: 85:15). MS (ES+) 470.00 [M+H]$^+$.

Crystallization:

The impure fraction was dissolved in hexanes and concentrated twice, then dissolved in hexanes (5 mL). Crystallization was induced by scratching and cooling in an ice-bath, then the slurry was left at room temperature for 72 h. The crystals were filtered off and washed with cold hexanes which gave a single diastereomer at the P-atom of the title compound as colourless needles (166 mg, 9%, dr>95:5 according to $^{19}$F- and $^{31}$P-NMR).

The mother liquor was concentrated and the crystallization was repeated using hexanes (5 mL) which gave further single diastereomer of the title compound (150 mg, 8%, dr>95:5 according to $^{19}$F- and $^{31}$P-NMR).

The purified 44:56-diastereomeric mixture from above (700 mg) was dissolved in hexanes (5 mL), cooled to 0° C. and seeded with crystals of single diastereomer (5 mg). The mixture was stored at 4° C. over night, then formed crystals were filtered off and washed with cold hexanes which gave further single diastereomer of the title compound as large colourless needles (120 mg, 6%, dr>95:5 according to $^{19}$F- and $^{31}$P-NMR).

Example R3

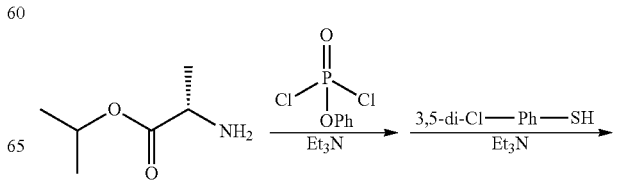

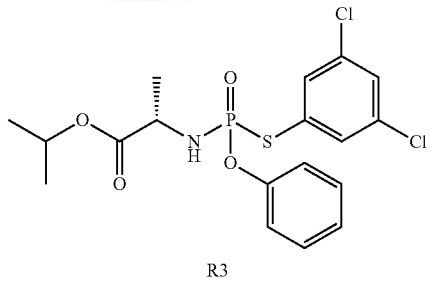

R3

((2S)-Isopropyl 2-((((3,5-dichlorophenyl)thio)(phenoxy)phosphoryl)amino)propanoate (R3)

Phenyl dichlorophosphate (3.78 g, 17.9 mmol) was added under nitrogen to a solution at −10° C. of (S)-isopropyl 2-aminopropanoate hydrochloride (1.03 g, 6.14 mmol) in DCM (36 mL) followed by dropwise addition of triethylamine (2.1 eq.) over 20 min. The mixture was stirred between −10° C. and 0° C. for 45 min. The temperature was lowered to −10° C. and a solution of 3,5-dichlorothiophenol in DCM (8 mL) was added followed by dropwise addition of triethylamine (1.1 eq.) over 10-15 min. The reaction was stirred for 30 min, then concentrated. The residue was dissolved in isopropyl acetate (60 mL) and solids were filtered off, washed with isopropyl acetate (2×10 mL) and discarded. The organic layer was washed with an aqueous solution of $KHCO_3$ (5%, 2×20 mL), dried ($Na_2SO_4$), filtered and concentrated. The afforded crude product was purified by column chromatography on silica eluted with 25% EtOAc in hexanes, which gave the title compound as a mixture of diastereomers at the P-atom (4.82 g, 60%).

Separation by Chiral SFC of Diastereomers (R3-1 & R3-2)

Compound R3 (19.6 g, 43.7 mmol) was subjected to chiral SFC using a YMC amylose SA column eluted with isopropylalcohol as mobile phase modifier, which gave the two isomers separated.

First eluting isomer, R3-1 (6.70 g, 34%), $^{31}$P NMR CDCl$_3$ δ 22.31

Second eluting isomer, R3-2 (7.30 g, 37%), $^{31}$P NMR CDCl$_3$ δ 21.90, 21.97

Crystallisation

Compound R3 (12 g, 14.2 mmol, 47:53 diastereomeric ratio at phosphorus) was dissolved in MTBE (20 mL) and hexane (120 mL) was added. Seeding material (R3-2) from the chiral SFC separation, (257 mg, diastereomeric purity 98.4%) was added and the solution was left at rt for 20 h, during which time crystals grew. The crystals were collected by filtration, washed with hexane (2×40 mL) and dried in vacuum which gave the pure diastereomer R3-2 (2.93 g).

$^{31}$P-NMR showed a diastereomeric purity at phosphorus of >99%.

The mother liquor was concentrated to dryness, yielding of a thick yellow oil (9.4 g) having a 64:36 diastereomeric ratio at phosphorus. The oil was re-dissolved in MTBE (10 mL) and hexane (90 mL), and the solution was seeded with (R3-2) from the chiral SFC separation, (211 mg, diastereomeric purity 98.4%).

The mixture was left at rt for 1 h, then at +4° C. for 5 h. Formed crystals were collected, washed with hexane (2×40 mL) and dried in vacuum which gave the pure diastereomer R3-2 (1.21 g).

$^{31}$P-NMR showed a diastereomeric purity at phosphorus of 98.6%.

Total yield for the two crops was of 65%.

Example R4

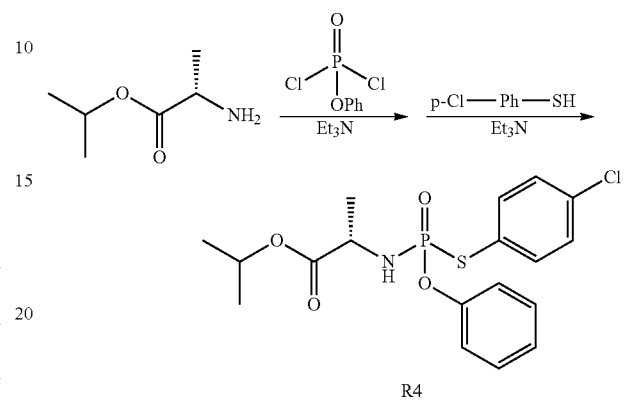

R4

(2S)-Isopropyl 2-((((4-chlorophenyl)thio)(phenoxy)phosphoryl)amino)propanoate (R4)

Phenyl dichlorophosphate (2.56 g, 12.1 mmol) was added under nitrogen to a solution at −10° C. of (S)-isopropyl 2-aminopropanoate hydrochloride (2.03 g, 12.1 mmol) in DCM (36 mL) followed by dropwise addition of triethylamine (2.1 eq.) over 20 min. The mixture was stirred between −10° C. and 0° C. for 45 min. The temperature was lowered to −10° C. and a solution of 4-dichlorothiophenol in DCM (4 mL) was added followed by dropwise addition of triethylamine (1.1 eq.) over 10-15 min. The reaction was stirred for 30 min, then concentrated. The residue was dissolved in tert-butyl methyl ether (40 mL) and solids were filtered off, washed with tert-butyl methyl ether (2×10 mL) and discarded. The organic combined layers were washed twice with saturated $KHCO_3$, dried ($Na_2SO_4$), filtered and concentrated. The afforded crude product was purified by column chromatography on silica eluted with 30% EtOAc in hexanes, which gave the title compound as a mixture of diastereomers at the P-atom (4.00 g, 80%). MS (ES−) 412.02 [M−H]$^−$.

Example C1

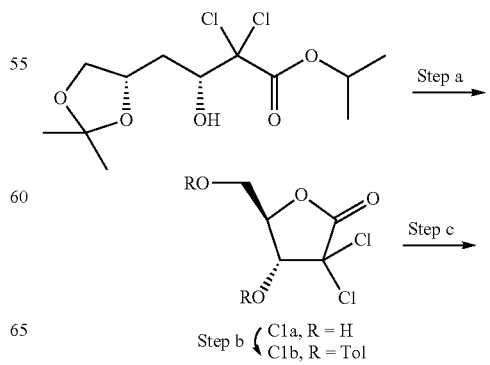

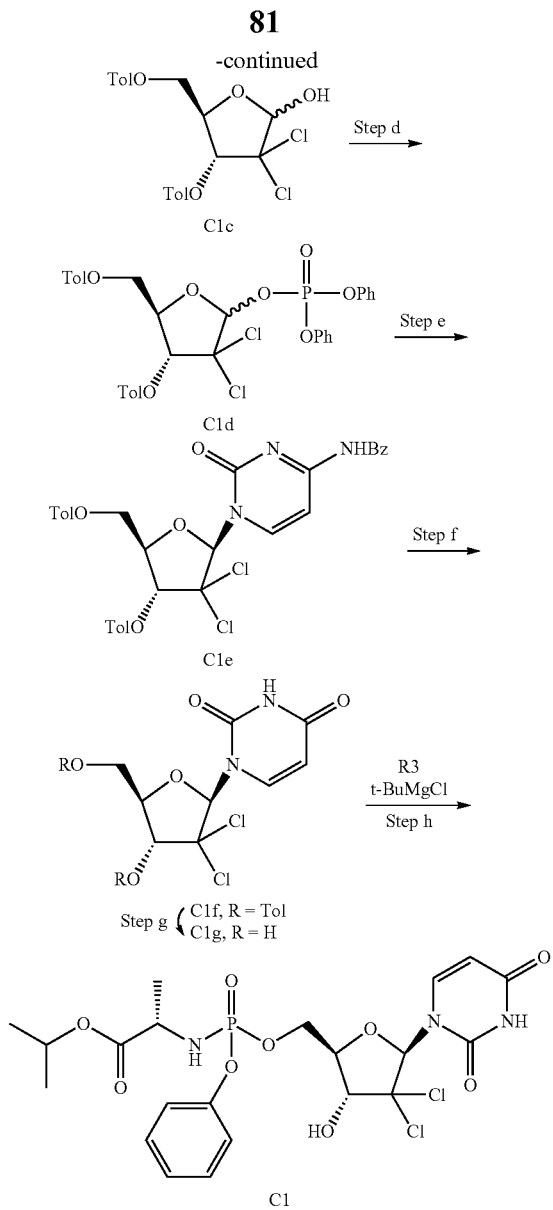

wise addition of p-toluoyl chloride (21.9 g, 136 mmol). The mixture was stirred at rt over night, then cooled to 0° C. and DMAP (332 mg, 2.71 mmol), Et$_3$N (1.65 g, 16.3 mmol) and p-toluoyl chloride were added. The mixture was stirred for 2 h at rt then the reaction was quenched with MeOH. Most of the THF was removed in vacuo and about of EtOAc (500 mL) was added. The organic phase was washed twice with 0.5M HCl, once with a saturated solution of sodium hydrogen carbonate and once with brine. The organic phase was dried (Na$_2$SO$_4$), filtered and concentrated under reduced pressure. The product was crystallized from isohexane (50 mL) and toluene (25 mL). The crystals were filtered of, washed with isohexane (50 mL) then toluene:isohexane 2/1, and dried in vacuo. The mother liquid was concentrated and purified by chromatography on a short silica column eluted with isohexane and 20% EtOAc. The product was crystallized from isohexane and dried in vacuo. Total yield: 20.7 g, 87%.

Step c) (2R,3R)-4,4-dichloro-5-hydroxy-2-(((4-methylbenzoyl)oxy)methyl)tetrahydrofuran-3-yl 4-methylbenzoate (C1c)

A 1M solution of lithium tri-tert-butoxyaluminohydride (52.1 mL, 52.1 mmol) was added drop wise at −25° C. to a solution of C1b (19.0 g, 43.4 mmol) was dissolved in dry THF (180 mL) the reaction was stirred for 15 min at −20° C. The cooling bath was removed and the reaction was allowed to come to 10° C. The reaction was quenched with saturated ammonium chloride solution (400 ml) and crashed ice. EtOAc (400 ml) was added and the mixture was stirred for 1 h. The organic phase was separated and the water phase was extracted four times with of EtOAc (4×100 ml). The combined organic phases were washed with 0.5M HCl (150 mL), brine (2×100 mL), dried (Na$_2$SO$_4$), filtered and concentrated. The afforded crude product was used in the next step without further purification Step d) (2R,3R)-4,4-Dichloro-5-((diphenoxyphosphoryl)oxy)-2-(((4-methylbenzoyl)oxy)methyl)-tetrahydrofuran-3-yl 4-methylbenzoate (C1d)

A solution of phosphoric acid diphenyl ester chloride in toluene (40 mL) was added drop wise at 10° C. to a solution of the crude product from previous step in a mixture of toluene (140 mL) and Et$_3$N (5.25 g, 51.9 mmol). The mixture was stirred at rt for 64 h, then cooled to 0° C., and a mixture of 1M HCl (50 mL) diluted with EtOAc (200 mL) was added. The phases were separated and the organic phase was washed with water, saturated sodium hydrogen carbonate solution and brine. The organic phase was dried (Na$_2$SO$_4$), filtered and concentrated. The product was crystallized from isopropanol/EtOAc and dried under vacuum which gave 11.8 g of the title compound. The mother liquid was concentrated and the residue crystallized from isopropanol dried under vacuum which gave further 7.5 g of the title compound. The mother liquid was concentrated and purified by silica gel chromatography eluted with isohexane and 5 to 10% EtOAc which gave further 8.5 g of the title compound. Total yield: 96%. MS (ES+) 688.1 [M+NH$_4$]+.

Step e) (2R,3R,5R)-5-(4-benzamido-2-oxopyrimidin-1(2H)-yl)-4,4-dichloro-2-(((4-methylbenzoyl)oxy)methyl)tetrahydrofuran-3-yl 4-methylbenzoate (C1e)

A suspension of N-benzoyl cytosine (1.92 g, 8.94 mmol) and ammonium sulfate (4.72 mg, 0.036 mmol) in HDMS Step a) (4R,5R)-3,3-Dichloro-4-hydroxy-5-(hydroxymethyl)dihydrofuran-2(3H)-one lactone formation (C1a)

A solution of (R)-isopropyl 2,2-dichloro-4-((S)-2,2-dimethyl-1,3-dioxolan-4-yl)-3-hydroxybutanoate (16.4 g, 54.3 mmol) prepared as described in J. Chem. Perkin Trans I, 1982, 2063-2066, in acetonitrile (150 mL), water (4.2 mL) and TFA was refluxed for 3 hours, then p-toluene sulfonic acid monohydrate (516 mg, 2.71 mmol) and toluene (60 mL) were added. The solvent was distilled off and new portions of toluene (3×60 mL) were added during the distillation, which lasted about three hours. The reaction solution was concentrated in vacuo and used crude in the next step.

Step b) (2R,3R)-4,4-Dichloro-2-(((4-methylbenzoyl)oxy)methyl)-5-oxotetrahydrofuran-3-yl 4-methylbenzoate (C1b)

Et$_3$N (16.5 g, 163 mmol) was added at 0° C. to a solution of the crude compound C1a in dry THF followed by drop (13.6 mL, 65.4 mmol) was boiled under argon for two hours, then cooled to rt and concentrated in vacuo. The residue was dissolved in chlorobenzene (100 mL) and a solution of C1d (3.00 g, 4.49 mmol) in chlorobenzene (70 mL) was added under argon. Tin (IV) tetrachloride was added drop wise at rt and the mixture was refluxed for 90 min. The reaction was cooled and poured into a saturated solution of ammonium chloride. The product was extracted four times with EtOAc and the combined organic phases were washed with brine, dried (Na$_2$SO$_4$), filtered and concentrated. The product was purified by silica gel chromatography with DCM and 2 to 4% methanol and then crystallized from ethanol. Yield 1.11 g, 35%

Step f) (2R,3R,5R)-4,4-Dichloro-5-(2,4-dioxo-3,4-dihydropyrimidin-1(2H)-yl)-2-(((4-methylbenzoyl)oxy)methyl)tetrahydrofuran-3-yl 4-methylbenzoate (C1f)

A suspension of C1e (1.06 g, 1.33 mmol) in 70% acetic acid was refluxed for 20 h, then concentrated onto silica and purified by silica gel column chromatography eluted with DCM and 0 to 20% ethyl acetate, which gave the title compound (537 mg, 76%). MS (ES+) 533.0 [M+H]+.

Step g) 1-((2R,4R,5R)-3,3-Dichloro-4-hydroxy-5-(hydroxymethyl)tetrahydrofuran-2-yl)pyrimidine-2,4 (1H,3H)-dione (C1g)

A suspension of C1f (2.78 g, 5.21 mmol) in 7M ammonia in methanol (110 mL) was stirred at rt for 96 h. The mixture was evaporated on silica gel and purified by column chromatography with DCM and 3 to 10% methanol and diethyl ether and 4% methanol. The product was dried in vacuo. Yield 558 mg, 36%. MS (ES+) 297.0 [M+H]$^+$.
$^1$H NMR (500 MHz, DMSO-d$_6$) δ 11.57 (s, 1H, 14), 8.06 (d, J=8.2 Hz, 1H, 12), 6.76 (d, J=6.3 Hz, 1H, 6), 6.41 (s, 1H, 7), 5.72 (dd, J=8.1, 1.4 Hz, 1H, 17), 5.47 (t, J=4.6, 4.6 Hz, 1H, 13), 4.35-4.27 (m, 1H, 2), 3.87-3.76 (m, 2H), 3.68-3.62 (m, 2H).
$^{13}$C NMR (126 MHz, DMSO-d$_6$) δ 162.60, 150.29, 138.96, 101.93, 93.47, 90.12, 81.38, 75.36, 66.23, 58.01, −0.00.

Step h) (2S)-Isopropyl 2-(((((2R,3R,5R)-4,4-dichloro-5-(2,4-dioxo-3,4-dihydropyrimidin-1(2H)-yl)-3-hydroxytetrahydrofuran-2-yl)methoxy)(phenoxy)phosphoryl)amino)propanoate (C1)

A flame dried two-necked flask was loaded with sugar C1f (100 mg, 0.337 mmol) and the system placed under nitrogen. THF (2 mL) was added and the suspension was gently heated to obtain a clear solution. The solution was cooled to −10° C. and a solution of tert-butylmagnesium chloride in THF was added dropwise. DMPU (0.9 mL) was added and the mixture was stirred at room temperature for 10 min. A solution of reagent R3 (181 mg, 0.404 mmol) in THF (1 mL) was added and the resulting mixture was stirred at room temperature overnight. The reaction was quenched with 0.5M hydrochloric acid (1.5 mL) and diluted with ethyl acetate (10 mL). The organic layer was dried (Na$_2$SO$_4$), filtered and concentrated. The product was isolated using C-18 preparative HPLC without separating the two phosphorus diastereomers which gave the title compound as a 3:1 mixture of P-diastereomers (42 mg, 22%).

Example C2

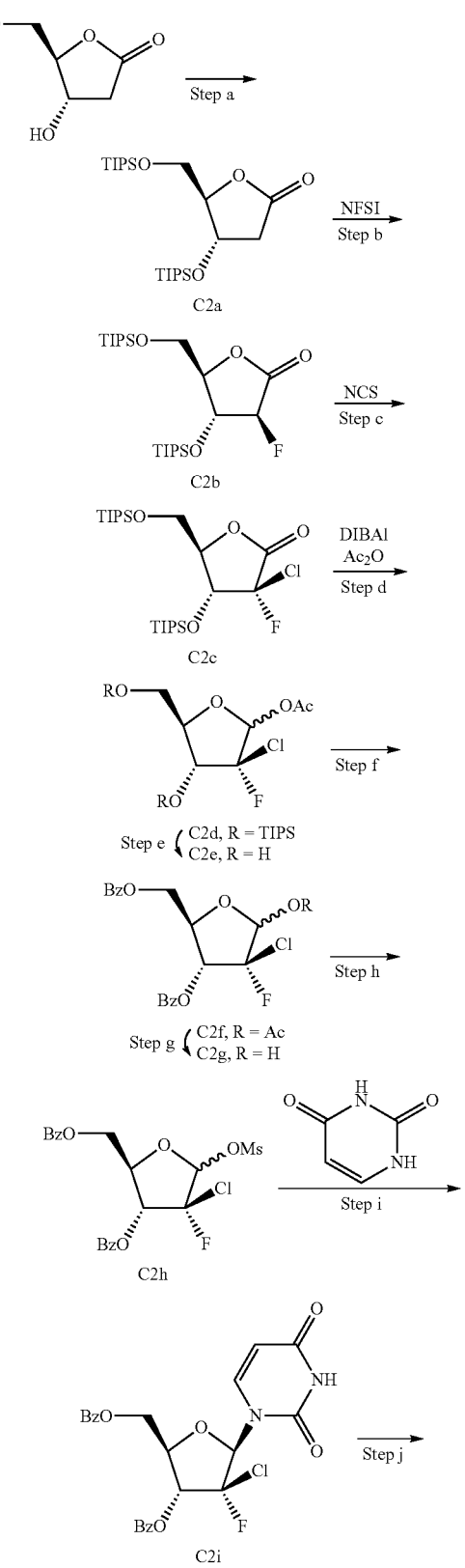

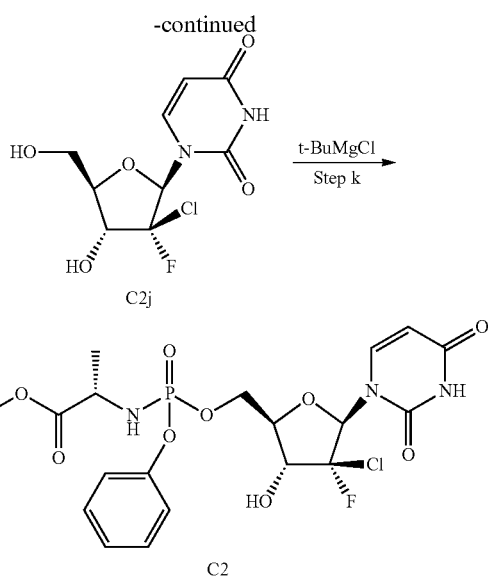

Step a) (4S,5R)-4-((Triisopropylsilyl)oxy)-5-(((triisopropylsilyl)oxy)methyl)dihydrofuran-2(3H)-one (C2a)

TIPS-chloride (16.4 g, 85 mmol) was added drop wise to an ice cooled stirred solution of (4S,5R)-4-hydroxy-5-(hydroxymethyl)dihydrofuran-2(3H)-one (3.30 g, 25.0 mmol) and imidazole (10.2 g, 150 mmol) in DMF (35 mL). The mixture was stirred for 1 h at 0° C. then at rt for 40 h. The reaction was quenched with water and the mixture extracted three times with EtOAc. The organic phase was dried (Na₂SO₄), filtered and concentrated, and the product was isolated by silica gel column chromatography eluted with a gradient of isohexane and 0 to 10% EtOAc. Mixed fractions were purified again by silica gel column chromatography eluted with toluene, which gave the title compound (11.1 g, 94%).

Step b) (3S,4R,5R)-3-Fluoro-4-((triisopropylsilyl)oxy)-5-(((triisopropylsilyl)oxy)methyl)-dihydrofuran-2(3H)-one (C2b)

A 1M solution of lithium bis(trimethylsilyl) amide (2.18 g, 13.0 mmol) was added dropwise during 10 min to a solution at −70° C. of compound C2a (4.45 g, 10.0 mmol) and NFSI (4.73 g, 15.0 mmol) in dry THF (50 mL). The mixture was stirred for 90 min at −70° C., then added to a saturated solution of ammonium chloride and cracked ice. The mixture was extracted three times with EtOAc, the organic phase was dried (Na₂SO₄), filtered and concentrated, and the product was isolated by silica gel chromatography eluted with a gradient of isohexane and 0 to 5% EtOAc. Yield 4.63 g, 67%.

Step c) (3S,4R,5R)-3-Chloro-3-fluoro-4-((triisopropylsilyl)oxy)-5-(((triisopropylsilyl)oxy)methyl)-dihydrofuran-2(3H)-one (C2c)

A 1M solution of lithium bis(trimethylsilyl) amide was added drop wise during 10 min to a solution at −70° C. of C2b (3.08 g, 6.65 mmol) and N-chlorosuccinimide (1.07 g, 7.99 mmol) in dry THF (25 mL). The mixture was stirred for 90 min at −70° C., then added to a saturated solution of ammonium chloride and cracked ice. The mixture was extracted three times with EtOAc, the organic phase was dried (Na₂SO₄), filtered and concentrated, and the product was isolated by silica gel chromatography eluted with a gradient of isohexane and 0 to 5% EtOAc. Yield 2.40 g, 73%.

Step d) (3S,4R,5R)-3-Chloro-3-fluoro-4-((triisopropylsilyl)oxy)-5-(((triisopropylsilyl)oxy)methyl)-tetrahydrofuran-2-yl acetate (C2d)

A 1M solution of Li(O-t-Bu)₃AlH in THF (39 mL, 39 mmol) was added dropwise under argon at −35° C. to solution of compound C2c (16.3 g, 32.8 mmol) in THF (120 mL). The mixture was stirred for 1 h at −35° C., then at rt for 1 h. The mixture was cooled to −25° C., DMAP (4.00 g, 32.8 mmol) was added and the mixture was stirred for 15 minutes, then acetic anhydride (33.5 g, 328 mmol) was added drop wise and the mixture was stirred 2 h. The mixture was allowed to come to 0° C. and EtOAc (200 mL) and water (200 mL) were added. The phases were separated and the water phase was extracted with EtOAc (×2). The combined organic phases were washed with water (×2) and with brine (×1). The organic phase was dried (Na₂SO₄), filtered and concentrated under reduced pressure. The residue was co-evaporated twice with toluene and the product was purified by chromatography on silica gel with eluted with isohexane and 2 to 6% EtOAc, which gave the title compound (17.1 g, 96%).

Step e) (3S,4R,5R)-3-Chloro-3-fluoro-4-hydroxy-5-(hydroxymethyl)tetrahydrofuran-2-yl acetate (C2e)

Triethylamine tri hydrofluoride (20.5 g, 126 mmol) was added to a stirred solution of compound C2d (17.0 g, 31.4 mmol) in acetonitrile (115 mL) and THF (23 mL). The mixture was stirred for 72 h at rt, 20 h at 50° C. and then at rt overnight. The solution was concentrated on silica (60 g) and purified by silica gel chromatography eluted with a gradient of isohexane and EtOAc, which gave the title compound (68.0 g, 85%).

Step f) (2R,3R,4S)-5-Acetoxy-2-((benzoyloxy)methyl)-4-chloro-4-fluorotetrahydrofuran-3-yl benzoate (C2f)

Triethylamine (10.8 g, 107 mmol) was added to a stirred solution of compound C2e (6.80 g, 26.8 mmol) under ice cooling followed by drop wise addition of benzoyl chloride (9.41 g, 66.9 mmol).

The mixture was allowed to attain rt and stirred overnight. EtOH (5 mL) was added and the mixture was stirred for 30 minutes, then concentrated in vacuo. Water was added and the mixture was extracted with EtOAc (×3). The organic phase was washed with water and brine, dried (Na₂SO₄), filtered and concentrated under reduced pressure. The product was purified by silica gel chromatography eluted with a gradient of isohexane and EtOAc, which gave the title compound (10.1 g, 86%).

Step g) ((2R,3R,4S)-3-(Benzoyloxy)-4-chloro-4-fluoro-5-hydroxytetrahydrofuran-2-yl)methyl benzoate (C2g)

Ethanolamine (1.55 g, 25.4 mmol) was added to a stirred solution of compound C2f (10.1 g, 23.0 mmol) in EtOAc (100 mL) and DMSO (50 mL). The mixture was stirred at rt for 72 h, then diluted with diethyl ether (300 mL) and EtOAc (300 mL) and washed with water (×4). The combined water phases were extracted with EtOAc then the EtOAc phase was washed with brine (×2). The combined organic phases were dried (Na$_2$SO$_4$), filtered and concentrated under reduced pressure. The product was purified by silica gel chromatography eluted with a gradient of DCM with and EtOAc, which gave the title compound (7.50 g, 82%).

Step h) ((2R,3R,4S)-3-(Benzoyloxy)-4-chloro-4-fluoro-5-((methylsulfonyl)oxy)tetrahydrofuran-2-yl) methyl benzoate (C2h)

Et$_3$N (3.54 mL, 25.4 mmol) was added at −15° C. under N$_2$ to a solution of compound C2g (8.36 g, 21.2 mmol) in dry DCM (100 mL) followed by addition of MsCl (1.97 mL, 25.4 mmol). The reaction mixture was stirred at −15° C. for 2 h, then poured into HCl (80 mL, 1M, aq.). The phases were separated and the aqueous layer was extracted with DCM. The combined organic extracts were washed with NH$_4$Cl (sat. aq.) dried (MgSO$_4$) and concentrated under reduced pressure to give the title compound (9.86 g, 98%) as a clear oil.

Step i) ((2R,3R,4S,5R)-3-(Benzoyloxy)-4-chloro-5-(2,4-dioxo-3,4-dihydropyrimidin-1(2H)-yl)-4-fluoro-tetrahydrofuran-2-yl)methyl benzoate (C2i)

Uracil (3.09 g, 27.5 mmol) and ammonium sulfate (48.5 mg, 0.367 mmol) was heated to reflux under N$_2$ in HMDS (49.3 mL, 236 mmol) for 16 h. The reaction mixture was cooled to rt, concentrated under reduced pressure and dried in vacuo. The residue in dry DCE (50 mL) was added under N$_2$ to a solution of compound C2h (8.68 g, 18.4 mmol) in dry DCE (75 mL). TMSOTf (6.12 g, 27.5 mmol) was slowly added under N$_2$ to the solution. After the addition, the reaction mixture was heated to 80° C. for 5 h and then at 65° C. for 16 h.

The reaction mixture was cooled to rt, quenched with NaHCO$_3$ (sat. aq.), filtered and extracted twice with DCM. The combined organic extracts were dried (MgSO$_4$) and concentrated under reduced pressure. EtOAc and DCM was added and the formed precipitate was collected by filtration which gave the pure β-isomer (660 mg, 7.4%). The filtrate was evaporated onto silica and purified by flash chromatography (hex:EtOAc 2:1–1:1), which gave the title compound as a mixture with the α-isomer, α:β>5:95 (942 mg, 11%).

Step j) 1-((2R,3S,4R,5R)-3-Chloro-3-fluoro-4-hydroxy-5-(hydroxymethyl)tetrahydrofuran-2-yl)pyrimidine-2,4(1H,3H)-dione (C2j)

Compound C2i (670 mg, 1.37 mmol) was suspended in NH$_3$ (7N in MeOH). After 30 min, EtOH (5 mL) was added and the suspension was stirred at rt. After an additional hour, the suspension went into solution and then reaction mixture was stirred at rt for 15 h. The solvents were evaporated under reduced pressure and the afforded residue was purified by flash chromatography (DCM:MeOH 10:1) which gave the title compound (380 mg, 99%) as a white solid. LC-MS ES− 279.31 [M−H]$^-$.
$^1$H NMR (500 MHz, DMSO) δ 10.39 (s, 1H), 7.87 (d, J=8.1 Hz, 1H), 6.74 (s, 1H), 6.22 (d, J=16.1 Hz, 1H, 7), 5.73 (d, J=8.1 Hz, 1H), 5.52 (s, 1H), 4.21 (dd, J=19.6, 9.2 Hz, 1H), 3.87–3.77 (m, 2H), 3.64 (dd, J=12.7, 2.8 Hz, 1H).

$^{13}$C NMR (126 MHz, DMSO) δ 162.76, 150.26, 139.06, 115.71, 113.71, 102.28, 86.98, 86.69, 81.01, 73.28, 73.14, 58.19.

Step k) ((2S)-Isopropyl 2-((((3,5-dichlorophenyl) thio)(phenoxy)phosphoryl)amino)propanoate (C2)

A flame dried two-necked flask was loaded with sugar C1i (100 mg, 0.337 mmol) and the system placed under nitrogen. THF (2 mL) was added and the suspension was gently heated to obtain a clear solution. The solution was cooled to −10° C. and a solution of tert-butylmagnesium chloride in THF was added dropwise. DMPU (0.9 mL) was added and the mixture was stirred at room temperature for 10 min. A solution of reagent R3 (181 mg, 0.404 mmol) in THF (1 mL) was added and the resulting mixture was stirred at room temperature overnight. The reaction was quenched with 0.5M hydrochloric acid (1.5 mL) and diluted with ethyl acetate (10 mL). The organic layer was dried (Na$_2$SO$_4$), filtered and concentrated. The product was isolated using C-18 preparative HPLC without separating the two phosphorus diastereomers which gave the title compound as a 3:1 mixture of P-diastereomers (42 mg, 22%).

Example C$_3$, Large Scale Peparaion of Compound C2

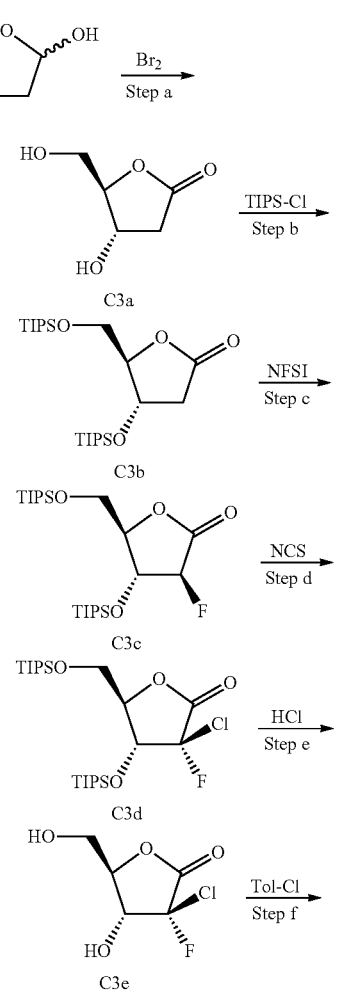

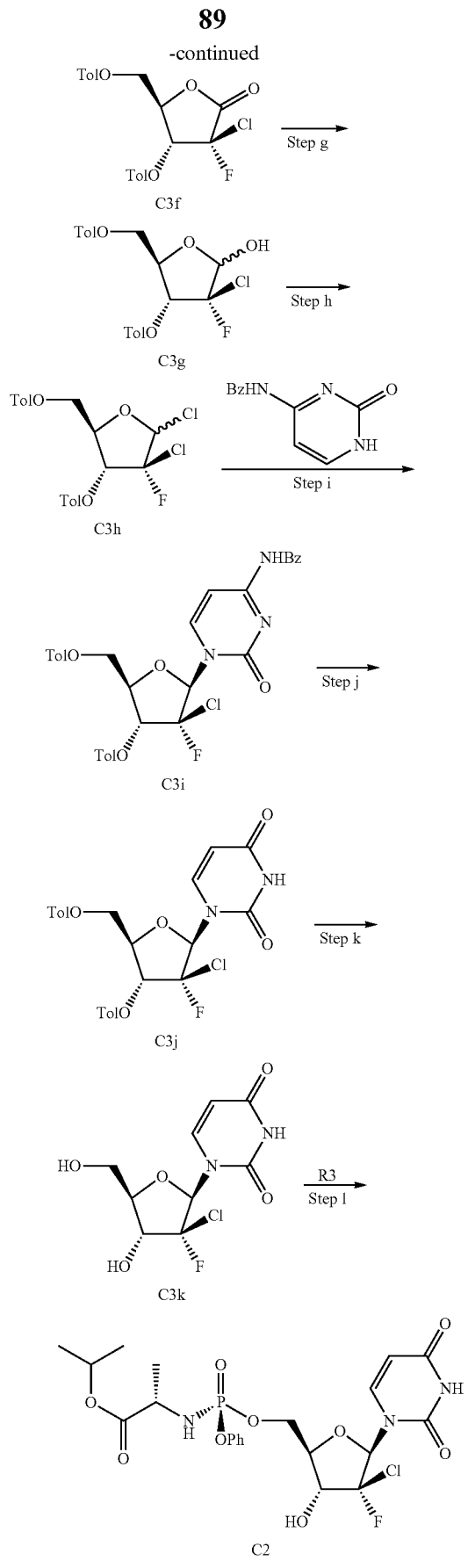

Step a) (4S,5R)-4-Hydroxy-5-(hydroxymethyl)dihydrofuran-2(3H)-one ($C_3a$)

Deoxy-D-ribose (400.0 g, 2.98 mol) was dissolved in water (1.6 kg) under nitrogen and the solution cooled to 3-7° C. Bromine (800 g, 10.0 mol, 3.36 eq.) was added at 3-7° C. while stirring over a period of approximately 2 hours and the stirring was continued at 3-7° C. for approximately 1 hour. The reaction mixture was gently warmed to 20-25° C. and then stirred for approximately 20 hours.

The reaction mixture was cooled to −5 to −7° C. and a solution of sodium hydroxide (27.65%, 720 g, 1.67 eq.) was added while keeping the reaction temperature at −3 to −7° C. The temperature was then adjusted to 0-5° C. and aqueous sodium hydroxide (9%, 470 g, 1.06 mol, 0.35 eq. was added at 0-5° C. to obtain a final pH=1.40.

The water was distilled off at reduced pressure using a scrubber (cooled, 14% sodium hydroxide, 0.9 L), finally at p<5 mbar and 50° C. In order to remove residual water from the product, 2-propanol was added portion wise to the residue followed by azeotropic distillation at reduced pressure. The final water content was determined by KF titration to be less than 1%. 2-Propanol (400 mL) was added to the residue and the mixture followed by filtration. The filter cake was washed with 2-propanol (1 L). The solvent was distilled off at reduced pressure. Toluene (400 mL) was added and distillation was resumed in order to remove residual 2-propanol and possibly more water. A residue of 474.6 g (120% yield) was obtained.

Step b) (4S,5R)-4-((Triisopropylsilyl)oxy)-5-(((triisopropylsilyl)oxy)methyl)dihydrofuran-2(3H)-one ($C_3b$)

Compound $C_3a$ (470.9 g, 2.97 mol) was dissolved in DMF (1.2 L) and cooled to 10-15° C. Imidazole (707.0 g, 10.4 mol, 3.5 eq.) was added and the temperature of the mixture was adjusted to 3-7° C. TIPS-CI (1145 g, 5.94 mol, 2.0 eq.) was added with cooling to 3-7° C. over a period of 2 hours. The reaction mixture was stirred at 3-7° C. for another ½ h, then gently warmed to 20-25° C. and stirred for 20 h. The progress of the reaction was monitored as follows: A sample of the reaction mixture was diluted 10 times with dry DMF, N;O-bis(trimethylsilyl)trifluoroacetamide (0.25 mL) was added to 0.5 mL of the sample in DMF and analyzed by GC. If the reaction was not complete the necessary amount of TIPS-CI was calculated and added and the stirring continued for another 20 hours.

When the reaction was completed, methanol (50 mL) was added and the mixture was stirred for ½-1 hour at 20-25° C. Water (1.2 kg) was added and the temperature of the mixture was adjusted to 15-25° C. pH was adjusted to pH 2.0-2.5 by careful addition of 36% hydrochloric acid (491 g, 4.7 mol). Toluene (0.9 kg) was added and the phases were separated. The organic phase was washed twice with 5% aqueous sodium chloride (1 kg). the aqueous phases were washed with toluene (0.9 kg). The organic phases were combined and dried with sodium sulfate (150 g) for minimum 1 hour. The suspension was filtered on a column prepared from silica Gel 60 (210 g) and toluene and the column was washed with toluene (1.1 kg). The combined filtrate was concentrated to dryness at reduced pressure at 50° C. which gave the title compound (1338 g, 84.4% from crude C2a). Purity (GC): 93.9%.

Step c) (3S,4R,5R)-3-fluoro-4-((triisopropylsilyl) oxy)-5-(((triisopropylsilyl)oxy)methyl)-dihydrofuran-2(3H)-one (C₃c)

Compound C₃b (450.0 g, 1.01 mol,) and NFSI (348.0 g, 1.10 mol) were dissolved in Me-THF (2.2 L) under argon. The solution was cooled to below −75° C. and lithium bis(trimethylsilyl)amide (20.2% in THF, 1.190 kg, 1.42 eq.) was added over a period of 3-4 hours. The progress of the reaction was monitored by GC, and when deemed completed, methylsulfide (6 g, 0.1 mol) was added to quench residual NFSI and the stirring continued for another 20-30 minutes.

The reaction mixture was transferred into aqueous 12.5% ammonium chloride (1.7 kg) and the mixture was warmed to room temperature. The aqueous layer (Aq. 1) was separated and the organic phase was washed with purified water (1 L). The aqueous wash (Aq. 2) was separated and the organic phase was secured. Aq. 1 was washed with heptanes (0.6 kg). The aqueous phase was separated and then discarded. Aq. 2 was added to the organic phase and the mixture was stirred for 1 minute. The aqueous phase was separated and discarded. The two organic phases were combined and concentrated at reduced pressure at 50° C. Heptanes (0.7 kg) was added to the residue and the resulting suspension was filtered. The filter cake was washed with heptanes (0.2 kg), the combined filtrate was concentrated at reduced pressure at 50° C., which gave 506 g crude product. The crude product was dissolved in a mixture of heptanes and toluene (0.5 L, 3:1) and purified by column chromatography on silica gel (silica gel 60, 2.5 kg and heptanes/toluene 3:1 v/v). The column was eluted with heptanes/toluene (3:1, 5.0 L), heptanes/toluene (2:1, 2.5 L), heptanes/toluene (3:1, 2.5 L) and toluene (7.5 L). Fractions of ~1 L were collected and fractions holding pure compound 2c were combined and concentrated and fractions holding mixtures of compound 2c and di-fluoro compound were combined and re-purified.

The above procedure was repeated twice, starting with 450 g and 525 g of compound 2b. Total yield of the title compound was 877.1 g (59.2%)+104.1 g (7.0%) from reworked material. Purity (GC): 92.4%.

Step d) (3S,4R,5R)-3-Chloro-3-fluoro-4-((triisopropylsilyl)oxy)-5-(((triisopropylsilyl)oxy)methyl)-dihydrofuran-2(3H)-one (C₃d)

Compound C₃c (400.0 g, 0.86 mol) and NCS (138.0 g, 1.04 mol, 1.2 eq.) were stirred in THF (2.0 L) under argon at ~20° C. The suspension was cooled to below −70° C. and then lithium bis(trimethylsilyl)amide (20.2% in THF, 1.150 kg, 1.6 eq.) was added over a period of 1-1.5 hours. The reaction was monitored by GC and when deemed completed, the mixture was transferred into a 12.5% aqueous solution of ammonium chloride (1.5 kg). The mixture was warmed to room temperature. The stirring was stopped and the aqueous layer was separated, washed with heptanes (0.8 L) and then discarded.

The mother organic phase was concentrated to dryness at reduced pressure at 55° C. and then added to the heptane wash. The thus combined organic phases were washed with 5% aqueous sodium chloride. The phases were separated and the aqueous phase washed with heptanes (0.2 L), then discarded. The organic phase was concentrated at reduced pressure which gave 440 g of crude product.

The procedure was repeated starting with 426.5 g of compound 2c which gave 473 g of crude product.

The combined crude products were dissolved in a mixture of heptanes and toluene (1.0 L, 2:1) and purified on a silica gel column prepared from silica gel 60 (2.25 kg) and heptanes/toluene 2:1 v/v. The column was eluted with: heptanes/toluene (2:1, 15 L). Fractions of 1 L were collected and pure fractions of compound 2d were combined and concentrated at reduced pressure which gave the title compound (667.3 g, 75.1%).

Step e) (3S,4R,5R)-3-Chloro-3-fluoro-4-hydroxy-5-(hydroxymethyl)dihydrofuran-2(3H)-one (C₃e)

Compound C₃d (613.0 g, 1.11 mol) was added to a 3 L glass reactor filled with nitrogen and methanol (1.2 L) and. To the stirred emulsion was added 37% hydrochloric acid (368.0 g, 3.73 mol, 3.4 eq.) and the mixture was heated to gentle reflux (73° C.). The mixture was kept at reflux for 20 hours then cooled to 15-20° C. and extracted with heptanes (4×600 mL). The residual methanolic solution was concentrated to dryness at reduced pressure using a water bath of 80-90° C., finally at p<35 mbar. Dioxane (600 mL) was added and distilled again as above, which gave the title compound (200.7 g, 98%).

Step f (2R,3R,4S)-4-chloro-4-fluoro-2-(((4-methylbenzoyl)oxy)methyl)-5-oxotetrahydrofuran-3-yl 4-methylbenzoate (C₃f)

A solution of compound C₃e (200.7 g, 1.11 mol) in dioxane (1.4 L) in a 3 L glass reactor filled with nitrogen and equipped with mechanical stirring, thermometer and an addition funnel was heated to 40 to 45° C. on a water bath. p-Toluoyl chloride (360.5 g, 2.33 mol, 2.1 eq.) was added whereafter triethylamine (258.3 g, 2.55 mol, 2.3 eq.) was added during 35 minutes so as to keep the reaction temperature below 70° C. The resulting suspension was then stirred at 65° C. for 2 hours, then cooled to 15° C. and filtered. The 800 mL filter cake was washed with dioxane (800 mL, 15° C.), leaving a white filter cake which was discarded. The filtrate was concentrated at reduced pressure, finally at 35 mbar using a water bath of 65° C. 2-Propanol (1.50 L) was added to the residual oil (510 g) so as to keep the temperature of the solution at 40-45° C. The solution was seeded and carefully allowed to cool to room temperature. During the cooling process samples of 0.25 mL were taken and mixed with 0.25 mL of water for pH measurements. Triethylamine (15 g) was added until pH 2.5-3.5 was obtained. Once room temperature was reached (one hour), the crystal suspension was cooled to 10±1° C. and kept at this temperature for 15 hours. The title product was isolated by filtration, washed with 2-propanol (600 mL, 5-10° C.) and then dried at 30-50° C. in an air vented oven. Yield: 374.2 g, 80%. Purity (HPLC): 99.4%. Melting point: 88.0-89.5C00 (1° C./min) crystal form change and then melts at 97-98° C.

Step a) (2R,3R,4S)-4-Chloro-4-fluoro-5-hydroxy-2-(((4-methylbenzoyl)oxy)methyl)-tetrahydrofuran-3-yl 4-methylbenzoate (C₃a)

A 3 L reaction flask set up with mechanical stirrer, thermometer and an addition funnel was filled with nitrogen. The flask was charged with ethyl acetate (1000 g) and cooled to 10° C. Lithium tri-tert-butoxyaluminium hydride (30% solution in THF, 35 g, 0.05 eq.) was added. Stirring at 10° C. was continued for 5-10 minutes and then compound C₃f (370.0 g, 0.88 mol) was added.

Further lithium tri-tert-butoxyaluminium hydride (30% solution in THF, 933.8 g, 1.10 mol, 1.25 eq.) was added over a period of 70 minutes while keeping the reaction temperature at 10° C. The reaction was quenched by pouring the reaction mixture onto a quench mixture (1.45 kg (10% NaCl-10% NH$_4$Cl in 3M HCl)) keeping the temperature at 10-15° C. The resulting suspension was warmed to 20-25° C. The aqueous was separated and discarded and the organic phase was washed with acidic water (1.0 L+10 mL of 3M HCl) followed by a wash with 25% sodium chloride (250 mL). The organic phase was concentrated to dryness, finally at p<35 mbar and 45° C. The residue was re-dissolved in toluene (0.45 kg) and the solution was again concentrated, at p<35 mbar and 45° C., which gave the title compound as an oil containing a little solid sodium chloride (412.6 g, 111%). Purity (HPLC) 97.5%.

Step h) (2R,3R,4S)-4,5-dichloro-4-fluoro-2-(((4-methylbenzoyl)oxy)methyl)tetrahydrofuran-3-yl 4-methylbenzoate (C$_3$h)

A 2000 mL reaction flask set up for mechanical stirring, temperature measurement and condenser was filled with nitrogen and charged with toluene (740 mL), compound C$_3$g (411.5 g, 0.88 mol) and thionyl chloride (174.0 g, 1.46 mol, 1.66 equivalents). The reaction flask was placed on a water bath, pre-heated to 50° C. and DMF (0.50 mL) was added. The top of the condenser was connected a cooled scrubber (700 g of 27.65% sodium hydroxide) and a steady flow of nitrogen was applied. The reaction started shortly after the DMF was added and it was followed by HPLC. After approximately three hours, the gas evolution has decreased and the temperature was increased to 60-65° C. Heating at 60-65° C. was continued for further 4.5 hours after which time the sulfite esters had vanished. The solvent and residual thionyl chloride was distilled off (500 mL) at reduced pressure using a water bath of 60-65° C. Toluene (650 mL) was added to the residual oil and the mixture was cooled to 5° C. Water (650 mL) was added and the pH was adjusted to 2.0-3.0 by addition of 3M sodium hydroxide (40 mL) at a temperature below 10° C. The temperature was adjusted to 20-22° C. and the aqueous phase was separated. The organic phase was washed with 25% sodium chloride (250 mL). The aqueous phases were back washed with toluene (250 mL). The combined organic phase was dried with magnesium sulfate (25 g) and filtered. Evaporation of the solvent (finally at p<35 mbar and 60° C.) provided the title compound as a light brown oil (378.5 g, 97% yield). Chlorobenzene (200 g) was added to the residue and the mixture was concentrated using the above conditions. The residue was again dissolved in chlorobenzene (200.0 g) and the mixture concentrated.

Step i) (2R,3R,4S,5R)-5-(4-Benzamido-2-oxo-3,4-dihydropyrimidin-1(2H)-yl)-4-chloro-4-fluoro-2-(((4-methylbenzoyl)oxy)methyl)tetrahydrofuran-3-yl 4-methylbenzoate (C3i)

A 500 mL round bottom flask was charged with N-benzoylcytosine (36.6 g, 170 mmol, 1.5 eq.), chlorobenzene (165 g, 150 mL) and ammonium sulfate (0.45 g, 3.4 mmol, 0.03 eq.), to this suspension was added HMDS (29.3 g, 181.3 mmol, 1.6 eq.). The suspension was heated to reflux. When the reaction mixture became a clear solution, it was refluxed for additional 1 h and then concentrated by distillation in vacuo at 60° C. (distillate: 150 mL). Chlorobenzene (125 mL) was added to the residue.

Residual toluene in Compound C$_3$h (50 g, 113.3 mmol) was removed by distillation in vacuo from chlorobenzene. The residue from this co-evaporation was dissolved in 1,2-dichloroethane (200 mL), and this solution was charged to the solution of silylated nucleoside in chlorobenzene. Tin(IV)chloride (59.0 g, 226.6 mmol, 2 eq.) was added and the mixture was heated to reflux under nitrogen. The reaction mixture was stirred at reflux for 65 h. The reaction mixture was cooled to 5° C., and ethyl acetate (99.8 g, 10 eq.) was added while keeping the temperature at 10-12° C. Total weight of mixture: 601.7 g. A quarter of this mixture (150.4 g, in theory 28.3 mmol) was charged to a 250 mL 3 necked round bottom flask, cooled to 5° C., and dichloromethane (147.5 g, 4×vol. of EtOAc) was added together with Celite (6.25 g). A warm (approx. 60° C.) 50% NaOH solution (17.6 g, 7.76 eq.) was added to the mixture in such a rate that the temperature was kept at 5-12° C. The mixture was stirred for 20 min at 10° C., then the temperature was adjusted to 25° C. and the mixture was stirred at this temperature for 30 min. The suspension was filtered on a pad of Celite (12.5 g) and the filter cake was washed with dichloromethane (190 mL). The combined filtrate and washings were concentrated to dryness by distillation in vacuo at 60° C. Dichloromethane (86 mL) was added to the residue then toluene (62 mL). The content of dichloromethane was removed by distillation in vacuo at 50° C. The resulting suspension was stirred at room temperature for 17 h whereafter the crude title compound was isolated by filtration. The filter cake was washed with toluene (25 mL) and the wet product was dried in an air ventilated dryer at 40° C., which gave title compound as a solid (5.56 g, 31.7%).

Step j) (2R,3R,4S,5R)-4-Chloro-5-(2,4-dioxo-3,4-dihydropyrimidin-1(2H)-yl)-4-fluoro-2-(((4-methylbenzoyl)oxy)methyl)tetrahydrofuran-3-yl 4-methylbenzoate (C$_3$j)

Compound C$_3$i (15.2 g 24.5 mmol) was suspended in 65% AcOH/water (152 mL, v/v), and the suspension was heated to reflux for 20 h. The reaction mixture was allowed to cool to room temperature, then water (53 mL) was added and the mixture was stirred at room temperature for 1.5 h. The suspension was filtrated and the filter cake washed with water (2×25 mL). The wet filter cake was dried in an air ventilated dryer at 40° C. for 20 h, which gave the title compound as a solid (10.8 g, 85%).

Step k) 1-((2R,3S,4R,5R)-3-Chloro-3-fluoro-4-hydroxy-5-(hydroxymethyl)tetrahydrofuran-2-yl)pyrimidine-2,4(1H,3H)-dione (C$_3$k)

Compound C$_3$j (8.0 g, 15.5 mmol) was suspended in MeOH (80 mL), n-propylamine (9.1 g, 154.8 mmol, 10 eq.) was added and the mixture was heated to 30° C. and stirred at this temperature for 24 h. The solvents were removed by distillation in vacuo at 40° C. The residue was taken up in water (20 mL), the aqueous phase was washed with DCM (3×40 mL) and the combined organic phases were washed with water (5 mL). The two aqueous phases were combined, and pH adjusted to 1.0 with 3 M HCl (approx. 7 mL). The acidic aqueous phase was extracted with Me-THF (4×40 mL), and the combined organic phases were concentrated to dryness by distillation in vacuo at 40° C. Isopropyl acetate (80 mL) was added to the residue, and the turbid mixture was concentrated in vacuo at 60° C. Isopropyl acetate (40 mL) was added and the distillation in vacuo was continued. Isopropyl acetate (10 mL) was added to the resulting thick suspension. The suspension was cooled to room temperature and stirred for 30 min. Crude title compound was collected by filtration, and the filter cake was washed with isopropyl acetate (2×4 mL). The afforded crude was dissolved in Me-THF (35 mL), isopropyl acetate (70 mL) was added and the mixture was concentrated by distillation in vacuo at 60° C. (distillate: 70 mL). Additional isopropyl acetate (30 mL) was added, and the distillation was continued (distillate: 30 mL). The suspension was cooled to room temperature, stirred at for 45 min and then filtered. The filter cake was washed with isopropyl acetate (2×4 mL) then dried in vacuo at room temperature. The title compound was isolated in 70% yield (3.0 g). Purity (HPLC) 98.5%.

Step 1) (S)-Isopropyl 2-(((S)-(((2R,3R,4S,5R)-4-chloro-5-(2,4-dioxo-3,4-dihydropyrimidin-1(2H)-yl)-4-fluoro-3-hydroxytetrahydrofuran-2-yl)methoxy)(phenoxy)phosphoryl)amino)propanoate A dried two-neck flask was loaded with compound $C_3k$ (500 mg, 1.78 mmol) and the system was placed under nitrogen. THF (12 mL) was added and the resulting solution was cooled to −10° C. A solution of tert-butylmagnesium chloride (437 mg, 3.74 mmol) in THF(26 mL) was added dropwise over a period of 20 min and the resulting off-white slurry was stirred cold for 30 min. A solution of R3 (998 mg, 2.23 mmol) in THF (9 mL) and DMPU (2.0 mL) was slowly added to the cold stirred suspension over a period of 45 min and the mixture stirred at +4° C. overnight. The reaction was quenched cold with 1M HCl (4.6 mL), diluted with toluene (20 mL) and stirred at room temperature for 10 min. The phases were separated and the water phase extracted with THF/toluene: 1/1(10 mL). The combined organic phases were washed with 1M HCl in half-brine (2×8 mL), followed by 5 wt % potassium bicarbonate in half-brine (2×8 mL) and finally half-brine (12 mL). The organic phase was filtered, the filtrate was concentrated to dryness and the crude dried in vacuum. The afforded syrup was purified by flash chromatography using a gradient of MeOH in DCM, 0% to 1.5% to 3% to 6%.

The isolated white solid was a 8:1 mixture of phosphorus stereoisomers according to $^{31}$P-NMR. The nmr spectra of the major isomer were consistent with nmr spectra obtained from the same compound prepared with the corresponding pentafluorophenyl phosphorylating agent of known stereochemistry, thus confirming the stereochemistry at the phosphorus atom to be S.

MS (ES+) 549.98 [M+H]+, ES−547.9 [M−H]−.

$^1$H NMR (500 MHz, DMSO) δ 1.15 (d, 6H), 1.23 (d, 3H), 3.80 (tq, 1H), 4.04 (m, 1H), 4.31 (m, 3H), 4.86 (hept, 1H), 5.63 (dd, 1H), 6.09 (dd, 1H), 6.24 (d, 1H), 6.66 (d, 1H), 7.21 (m, 3H), 7.38 (m, 2H), 7.58 (d, 1H), 11.63 (m, 1H).

$^{13}$C NMR (126 MHz, DMSO) δ 19.64 (d), 21.26, 21.30, 49.67, 64.32, 67.89, 74.42 (d), 78.81, 87.60 (m), 102.27, 113.96 (d), 119.96 (d), 124.52, 129.56, 139.91, 150.01, 150.53 (d), 162.52, 172.45 (d).

$^{31}$P NMR (162 MHz, DMSO) δ 3.76.

$^{19}$F NMR (376 MHz, DMSO) δ −119.05.

Example C4

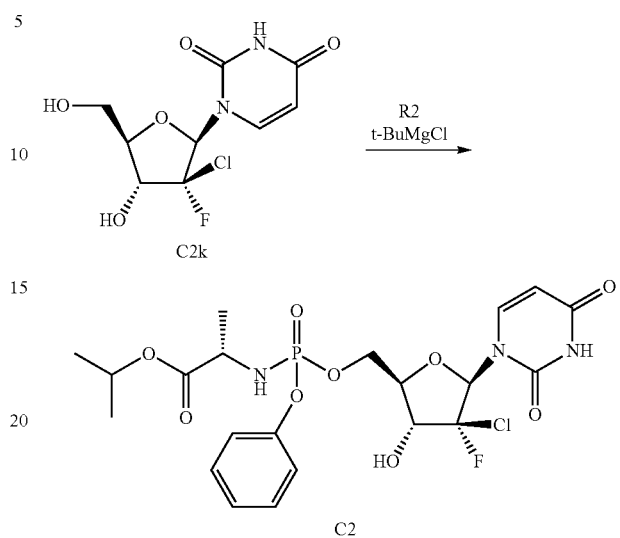

(2S)-isopropyl 2-(((((2R,3R,4S,5R)-4-chloro-5-(2,4-dioxo-3,4-dihydropyrimidin-1(2H)-yl)-4-fluoro-3-hydroxytetrahydrofuran-2-yl)methoxy)(phenoxy)phosphoryl)amino)propanoate (C2)

t-BuMgCl (87.5 mg, 0.75 mmol) was added dropwise at 0° C. under $N_2$ over 10 min to a solution of nucleoside C2k (100 mg, 0.36 mmol) in dry THF (1.0 mL) and dry DMPU (0.6 mL). The white suspension was stirred at the indicated temperature for 5 min and then at RT for 20 min. The white suspension was then cooled to 0° C., then a solution of R2 (200 mg, 0.43 mmol) in dry THF (1.0 mL) was added dropwise over 75 min at 0° C. via a syringe pump under $N_2$. The reaction mixture was stirred at the indicated temperature for 17 h and then quenched with HCl (2 M aq., 0.5 mL). The mixture was diluted with toluene (4 mL) and washed with 1 M HCl (2×2 mL), water (2 mL), $Na_2CO_3$ (5×2 mL) water (2×2 mL), brine (2 mL). The aqueous phase was extracted twice with EtOAc. The combined organic extracts were washed with water and brine, dried ($MgSO_4$) and concentrated under reduced pressure which gave the title compound (169 mg) as an amorphous white solid. $^{31}$P-NMR analysis of the afforded crude compound showed a 4.6:1 mixture of phosphorous isomers.

Example C5

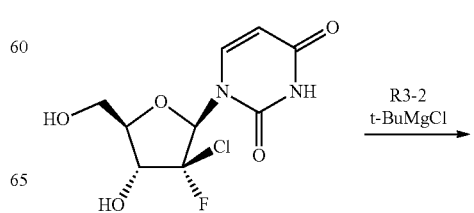

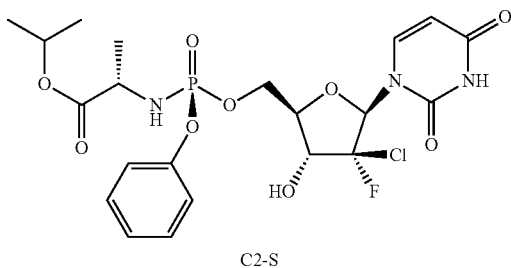

C2-S (S)-Isopropyl 2-(((S)-(((2R,3R,4S,5R)-4-chloro-5-(2,4-dioxo-3,4-dihydropyrimidin-1(2H)-yl)-4-fluoro-3-hydroxytetrahydrofuran-2-yl)methoxy)(phenoxy)phosphoryl)amino)propanoate (C2-S)

t-BuMgCl (175 mg, 1.50 mmol) was added dropwise at rt under $N_2$ to a solution of 1-((2R,3S,4R,5R)-3-chloro-3-fluoro-4-hydroxy-5-(hydroxymethyl)tetrahydrofuran-2-yl)pyrimidine-2,4(1H,3H)-dione (200 mg, 0.713 mmol) in dry THF (4.8 ml). The suspension was stirred at rt for 30 min and was then cooled to −10−−15° C., then a solution of the phosphorylating agent R3-2 (399 mg, 0.891 mmol) in dry THF/DMPU (4.0+0.82 ml) was added dropwise via a syringe at −10−−15° C. over 15 min under $N_2$. The reaction mixture was stirred at −10° C. for 15 min, then at 6° C. for 24 h. LC-MS after 19 h showed 86.4% conversion, 76.6% product and product:bis-phosphorylation 89:11 in a very clean reaction.

The reaction was quenched with 1M HCl (1.8 ml) and diluted with toluene (8 ml). The mixture was stirred at rt for 20 min, then the layers were separated and the organic layer was washed with HCl (1M in 50% brine, 2×3.2 ml). The combined acidic aqueous layers were extracted with THF:toluene (1:1, 4 ml). The combined organic layers were washed with $KHCO_3$ (5 w %, 3×3.2 mL), half-brine (4.8 ml), dried ($MgSO_4$) and concentrated under reduced pressure. LC-MS after work-up showed product:bis-phosphorylation 88:12, and almost complete removal of remaining nucleoside and thiophenol by-products. The afforded crude product was purified by flash chromatography (0-1.5-3-6% MeOH in DCM) which gave the title compound (256 mg, 65%) as a white foam. MS (ES+) 550.10 [M+H]$^+$, (ES−) 548.07 [M−H]$^−$. $^{31}$P-NMR δ 3.4 ppm.

The invention claimed is:

1. A method for preparing a compound of Formula Ia or Ib:

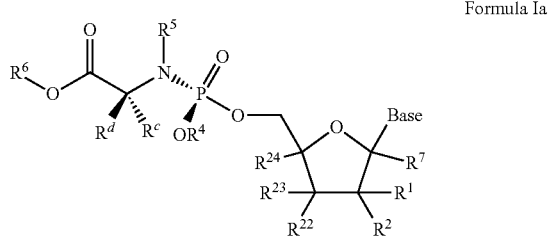

Formula Ia

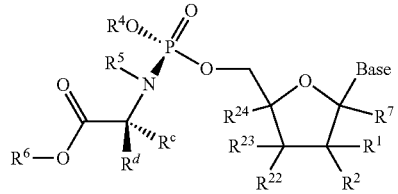

Formula Ib or a pharmaceutically acceptable salt or acid thereof;

wherein:

each $R^1$, $R^2$, $R^7$, $R^{22}$, $R^{23}$ or $R^{24}$ is independently H, $OR^{11}$, $NR^{11}R^{12}$, $C(O)NR^{11}R^{12}$, —$OC(O)NR^{11}R^{12}$, $C(O)OR^{11}$, $OC(O)OR^{11}$, $S(O)_nR^a$, $S(O)_2NR^{11}R^{12}$, $N_3$, CN, halogen, ($C_1$-$C_8$)alkyl, ($C_3$-$C_8$)carbocyclyl, ($C_4$-$C_8$)carbocyclyl alkyl, ($C_2$-$C_8$)alkenyl, ($C_2$-$C_8$)alkynyl or aryl($C_1$-$C_8$)alkyl; or any two $R^1$, $R^2$, $R^7$, $R^{22}$, $R^{23}$ or $R^{24}$ on adjacent carbon atoms when taken together are —O(CO)O— or —O($CR^{11}R^{12}$)O— or when taken together with the ring carbon atoms to which they are attached form a double bond;

each Base is independently a naturally occurring or modified purine or pyrimidine base linked to the furanose ring through a carbon or nitrogen atom;

each n is independently 0, 1, or 2;

each $R^a$ or $R^6$ is independently ($C_1$-$C_8$)alkyl, ($C_2$-$C_8$)alkenyl, ($C_2$-$C_8$)alkynyl, ($C_3$-$C_8$)carbocyclyl, ($C_4$-$C_8$)carbocyclylalkyl, aryl($C_1$-$C_8$)alkyl, heterocyclyl($C_1$-$C_8$)alkyl, ($C_6$-$C_{20}$)aryl, ($C_2$-$C_{20}$)heterocyclyl or heteroaryl;

each $R^c$ or $R^d$ is independently H, ($C_1$-$C_8$)alkyl, ($C_2$-$C_8$)alkenyl, ($C_2$-$C_8$)alkynyl, ($C_3$-$C_8$)carbocyclyl, ($C_4$-$C_8$)carbocyclylalkyl, aryl($C_1$-$C_8$)alkyl, heterocyclyl($C_1$-$C_8$)alkyl, ($C_6$-$C_{20}$)aryl, heterocyclyl or heteroaryl;

each $R^4$ is phenyl;

each $R^5$ is independently H, ($C_1$-$C_8$)alkyl, ($C_2$-$C_8$)alkenyl, ($C_2$-$C_8$)alkynyl, ($C_3$-$C_8$)carbocyclyl, ($C_4$-$C_8$)carbocyclylalkyl, aryl($C_1$-$C_8$)alkyl, heterocyclyl($C_1$-$C_8$)alkyl, ($C_6$-$C_{20}$)aryl, heterocyclyl or heteroaryl;

each $R^{11}$ or $R^{12}$ is independently H, ($C_1$-$C_8$)alkyl, ($C_2$-$C_8$)alkenyl, ($C_2$-$C_8$)alkynyl, ($C_3$-$C_8$)carbocyclyl, ($C_4$-$C_8$)carbocyclylalkyl, aryl($C_1$-$C_8$)alkyl, heterocyclyl($C_1$-$C_8$)alkyl, ($C_6$-$C_{20}$)aryl, heterocyclyl, heteroaryl, —C(=O)($C_1$-$C_8$)alkyl, —S(O)$_n$($C_1$-$C_8$)alkyl, or $R^{11}$ and $R^{12}$ taken together with a nitrogen to which they are both attached form a 3 to 7 membered heterocyclic ring wherein any one carbon atom of said heterocyclic ring can optionally be replaced with —O—, —S(O),- or —$NR^a$—; and wherein each ($C_1$-$C_8$)alkyl, ($C_2$-$C_8$)alkenyl, ($C_2$-$C_8$)alkynyl, ($C_3$-$C_8$)carbocyclyl, ($C_4$-$C_8$)carbocyclylalkyl, aryl ($C_1$-$C_8$)alkyl, heterocyclyl($C_1$-$C_8$)alkyl, ($C_6$-$C_{20}$)aryl, heterocyclyl or heteroaryl of each $R^c$, $R^d$, $R^1$, $R^2$, $R^{22}$, $R^{23}$, $R^{24}$, $R^5$, $R^6$, $R^7$, $R^{11}$ or $R^{12}$ or the phenyl of $R^4$ is, independently, optionally substituted with one or more halo, hydroxy, CN, $N_3$, $N(R^a)_2$, $NH(R^a)$, $NH_2$, $NO_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $C(O)R^a$, $OC(O)R^a$, $S(O)_nR^a$ $S(O)_2N(R^a)_2$, $S(O)_2NH(R^a)$, $S(O)_2NH_2$, $OR^a$ or $R^a$;

said method comprising:
(a) providing a compound of Formula II

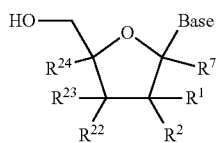

Formula II and
(b) treating the compound of Formula II with a compound of Formula IIIa and a base

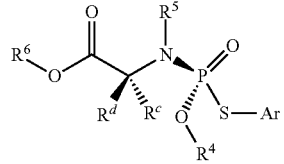

Formula IIIa thereby forming a compound of Formula Ia, or
(c) treating the compound of Formula II with a compound of Formula IIIb and a base

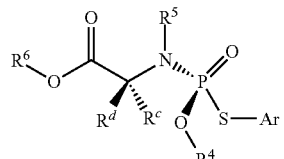

Formula IIIb thereby forming a compound of Formula Ib;
wherein:
each Ar is 3,5-dichlorophenyl.

2. The method of claim 1, wherein $R^1$ is $CH_3$ or Cl, and $R^2$ is F or Cl.

3. The method of claim 1, wherein each $R^5$, $R^{23}$ and $R^{24}$ is H.

4. The method of claim 1, wherein one of $R^c$ or $R^d$ is H and the other of $R^c$ or $R^d$ is optionally substituted ($C_1$-$C_8$) alkyl.

5. The method of claim 1, wherein $R^6$ is optionally substituted ($C_1$-$C_8$)alkyl or optionally substituted ($C_3$-$C_8$) cycloalkyl.

6. The method of claim 1, wherein the compound of formula IIIa or IIIb is selected from the group consisting of

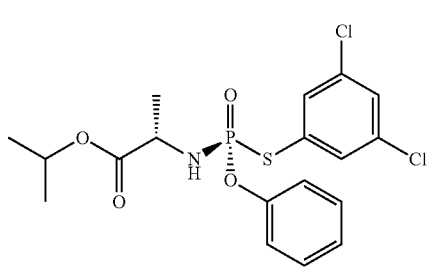

-continued

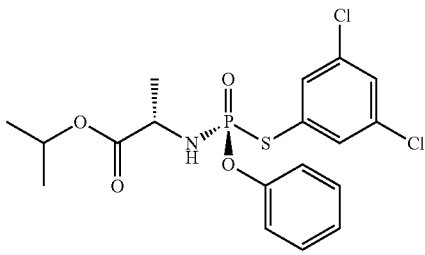

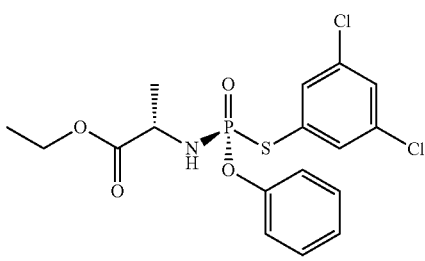

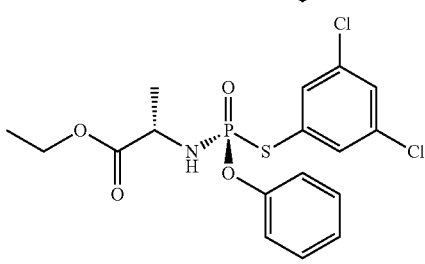

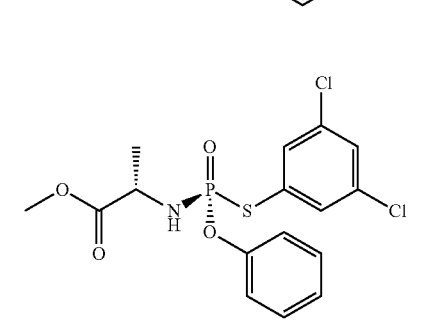

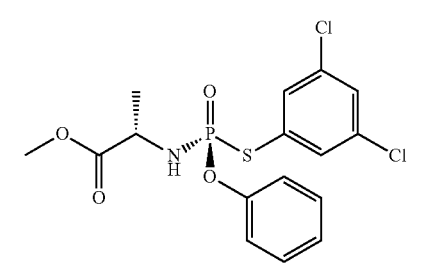

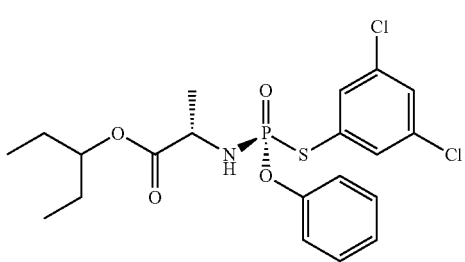

101

-continued

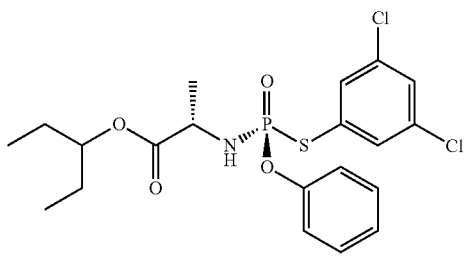

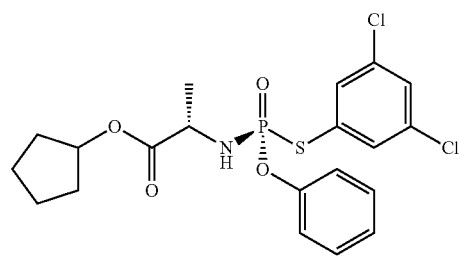

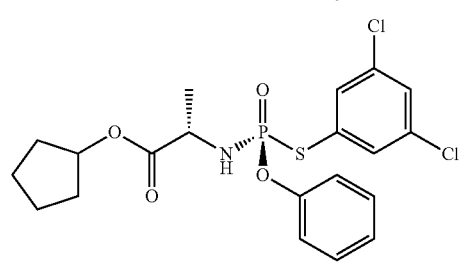

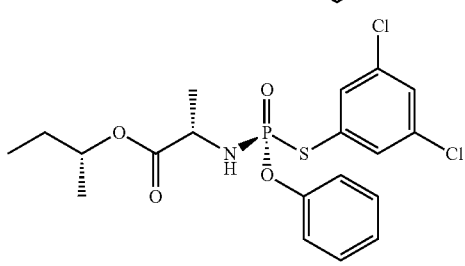

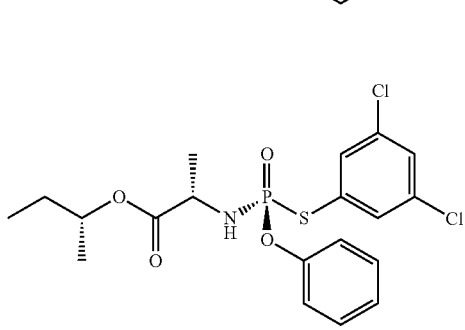

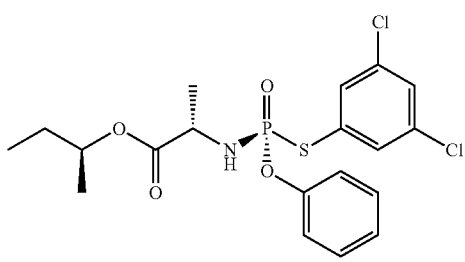

102

-continued

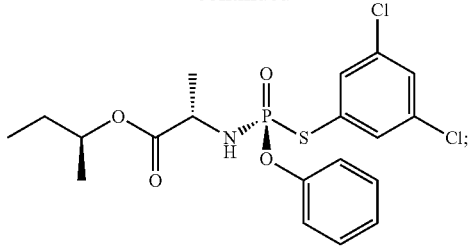

or salts or hydrates thereof.

7. A compound of the formula VIII

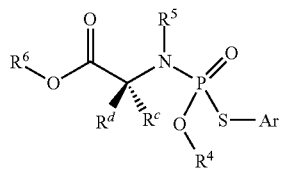

Formula VIII wherein:
each $R^a$, or $R^6$ is independently $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, heterocyclyl or heteroaryl;
each $R^c$ or $R^d$ is independently H, $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, heterocyclyl or heteroaryl;
each $R^4$ is optionally substituted phenyl;
each $R^5$ is independently H, $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, heterocyclyl or heteroaryl;
wherein each $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, heterocyclyl or heteroaryl of each $R^c$, $R^d$, $R^5$ or $R^6$ or the phenyl of $R^4$ is, independently, optionally substituted with one or more halo, hydroxy, CN, $N_3$, $N(R^a)_2$, $NH(R^a)$, $NH_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $S(O)_nR^a$, $S(O)_2N(R^a)_2$, $S(O)_2NH(R^a)$, $S(O)_2NH_2$, $OR^a$ or $R^a$; and
each Ar is 3,5-dichlorophenyl:
or a salt, hydrate or N-oxide thereof.

8. A diastereomer of the compound of claim 7 with the stereochemistry depicted in Formula IIIa:

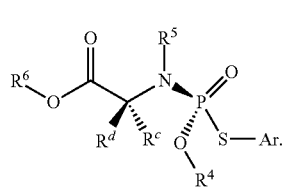

Formula IIIa

9. A diastereomer of the compound of claim 7 with the stereochemistry depicted in Formula IIIb:

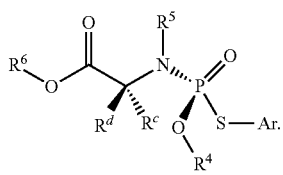

Formula IIIb

10. The diastereomer or compound of any one of claim 7, wherein $R^5$ is H.

11. The diastereomer or compound of claim 7, wherein $R^5$ is H and one of $R^c$ or $R^d$ is H.

12. The diastereomer or compound of claim 7, wherein $R^6$ is optionally substituted $(C_1-C_8)$alkyl or optionally substituted $(C_3-C_8)$cycloalkyl.

13. The diastereomer or compound of claim 12, wherein $R^6$ is methyl, ethyl, 1-methylbutyl, 2-ethylbutyl, cyclopentyl or preferably isopropyl.

14. The diastereomer or compound of claim 7, wherein $R^4$ is phenyl.

15. The diastereomer or compound of claim 7, wherein one of $R^c$ and $R^d$ is H and the other one is $CH_3$.

16. The diastereomer or compound of claim 15, wherein the stereochemistry at the chiral center to which $R^c$ and $R^d$ are directly attached is S.

17. The diastereomer or compound of claim 7, wherein:
$R^4$ is phenyl;
$R^5$ is H;
$R^6$ is methyl, ethyl, 1-methylbutyl, 2-ethylbutyl, cyclopentyl or preferably isopropyl;
one of $R^c$ and $R^d$ is H and the other one is $CH_3$;
Ar is 3,5-dichlorophenyl.

18. The method of claim 1, wherein the compound of formula Ia is

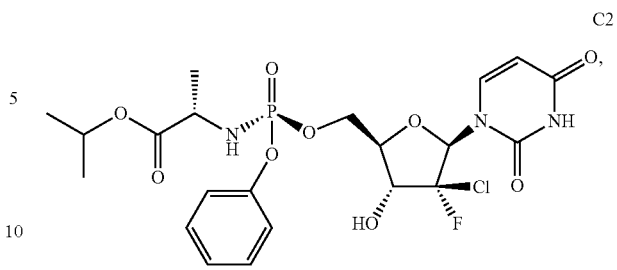

the compound of formula II is

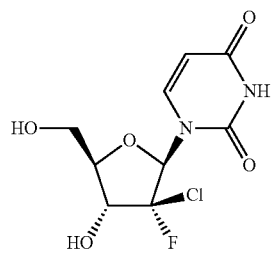

and the compound of formula IIIb is

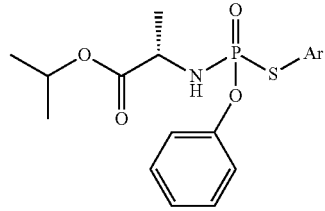

wherein Ar is 3,5-dichlorophenyl.

* * * * *